US012227560B2

(12) United States Patent
Carter et al.

(10) Patent No.: US 12,227,560 B2
(45) Date of Patent: Feb. 18, 2025

(54) ANTI-CHIKV ANTIBODIES AND USES THEREOF

(71) Applicant: SANOFI, Paris (FR)

(72) Inventors: Kara Carter, Bridgewater, NJ (US); Cendrine Lemoine, Paris (FR); Marie Mandron, Paris (FR); Sunghae Park, Bridgewater, NJ (US); Huawei Qiu, Bridgewater, NJ (US); Jonathan Rothblatt, Bridgewater, NJ (US)

(73) Assignee: SANOFI, Paris (FR)

( * ) Notice: Subject to any disclaimer, the term of this patent is extended or adjusted under 35 U.S.C. 154(b) by 17 days.

(21) Appl. No.: 17/672,871

(22) Filed: Feb. 16, 2022

(65) Prior Publication Data

US 2022/0275063 A1 Sep. 1, 2022

Related U.S. Application Data

(62) Division of application No. 15/787,647, filed on Oct. 18, 2017, now Pat. No. 11,286,295.

(30) Foreign Application Priority Data

Oct. 20, 2016 (EP) .................................... 16306374

(51) Int. Cl.
*C07K 16/10* (2006.01)
*A61P 31/14* (2006.01)
*A61K 39/00* (2006.01)

(52) U.S. Cl.
CPC .......... *C07K 16/1081* (2013.01); *A61P 31/14* (2018.01); *A61K 2039/505* (2013.01); *C07K 2317/21* (2013.01); *C07K 2317/52* (2013.01); *C07K 2317/524* (2013.01); *C07K 2317/526* (2013.01); *C07K 2317/565* (2013.01); *C07K 2317/72* (2013.01); *C07K 2317/732* (2013.01); *C07K 2317/76* (2013.01); *C07K 2317/92* (2013.01); *C07K 2317/94* (2013.01); *Y02A 50/30* (2018.01)

(58) Field of Classification Search
CPC ................................................. C07K 16/1081
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 4,861,719 | A | 8/1989 | Miller |
| 5,202,238 | A | 4/1993 | Fell et al. |
| 5,204,244 | A | 4/1993 | Fell et al. |
| 5,278,056 | A | 1/1994 | Bank et al. |
| 5,500,362 | A | 3/1996 | Robinson et al. |
| 5,585,089 | A | 12/1996 | Queen et al. |
| 5,821,337 | A | 10/1998 | Carter et al. |
| 5,859,205 | A | 1/1999 | Adair et al. |
| 5,882,877 | A | 3/1999 | Gregory et al. |
| 6,013,516 | A | 1/2000 | Verma et al. |
| 6,127,175 | A | 10/2000 | Vigne et al. |
| 6,464,998 | B1 | 10/2002 | Beuzard et al. |
| 6,737,056 | B1 | 5/2004 | Presta et al. |
| 7,244,430 | B2 | 7/2007 | Throsby et al. |
| 7,371,826 | B2 | 5/2008 | Presta et al. |
| 7,670,600 | B2 | 3/2010 | Dall Acqua et al. |
| 7,785,791 | B2 | 8/2010 | Presta et al. |
| 8,088,376 | B2 | 1/2012 | Chamberlain |
| 8,323,962 | B2 | 12/2012 | Dall Acqua et al. |
| 8,394,925 | B2 | 3/2013 | Chamberlain et al. |
| 8,449,887 | B2 | 5/2013 | Brehin et al. |
| 8,546,543 | B2 | 10/2013 | Lazar et al. |
| 8,852,609 | B2 | 10/2014 | Weiner et al. |
| 9,441,032 | B2 | 9/2016 | Warter et al. |
| 9,442,114 | B2 | 9/2016 | Despres et al. |
| 9,902,765 | B2 | 2/2018 | Doranz et al. |
| 9,994,629 | B2 | 6/2018 | Weiner et al. |
| 2003/0096977 | A1 | 5/2003 | Koike et al. |
| 2009/0041770 | A1 | 2/2009 | Chamberlain et al. |
| 2013/0189279 | A1 | 7/2013 | Warter et al. |

(Continued)

FOREIGN PATENT DOCUMENTS

| | | | |
|---|---|---|---|
| CA | 2982491 | A1 | 10/2016 |
| CN | 102746404 | A | 10/2012 |

(Continued)

OTHER PUBLICATIONS

Sela-Culang, I., et al., Oct. 2013, The structural basis of antibody-antigen recognition, Front. Immunol. 4(Article 302), pp. 1-13.*

(Continued)

*Primary Examiner* — Jeffrey S Parkin
(74) *Attorney, Agent, or Firm* — MH2 Technology Law Group, LLP

(57) ABSTRACT

The present invention concerns antibodies and antigen-binding fragments of antibodies which specifically bind to and neutralize Chikungunya virus (CHIKV) and which are engineered to develop therapeutics in order to treat CHIKV disease or prevent CHIKV infection. The invention also relates to pharmaceutical compositions comprising antibodies of the invention and the use of the antibodies for the prevention and treatment of CHIKV disease.

22 Claims, 20 Drawing Sheets

Specification includes a Sequence Listing.

(56) References Cited

U.S. PATENT DOCUMENTS

| | | | |
|---|---|---|---|
| 2015/0099863 A1 | 4/2015 | Chamberlain et al. |
| 2015/0191533 A1 | 7/2015 | Chamberlain et al. |
| 2016/0145323 A1 | 5/2016 | Doranz et al. |
| 2018/0079802 A1 | 3/2018 | Crowe et al. |

FOREIGN PATENT DOCUMENTS

| | | | |
|---|---|---|---|
| EP | 0173494 A2 | 3/1986 |
| EP | 2050764 A1 | 4/2009 |
| EP | 2808343 A1 | 12/2014 |
| EP | 2235059 B1 | 2/2015 |
| EP | 2444423 B1 | 3/2015 |
| EP | 2001900 B1 | 4/2015 |
| EP | 2197912 B1 | 8/2015 |
| EP | 3021868 A1 | 5/2016 |
| EP | 2374816 B1 | 9/2016 |
| EP | 3529271 A1 | 8/2019 |
| ES | 2588738 T3 | 11/2016 |
| JP | 2008-519860 A | 6/2008 |
| JP | 2014-524748 A | 9/2014 |
| WO | WO 1987/002671 A1 | 5/1987 |
| WO | WO 1987/005330 A1 | 9/1987 |
| WO | WO 1994/019478 A1 | 9/1994 |
| WO | WO 1995/014785 A1 | 6/1995 |
| WO | WO 1996/022378 A1 | 7/1996 |
| WO | WO 1997/010354 A1 | 3/1997 |
| WO | WO 1998/045322 A2 | 10/1998 |
| WO | WO 2012/106578 A1 | 8/2012 |
| WO | WO 2013/011076 A2 | 1/2013 |
| WO | WO 2015/010125 A1 | 1/2015 |
| WO | WO 2016/168417 A2 | 10/2016 |
| WO | WO 2018/073387 A1 | 4/2018 |

OTHER PUBLICATIONS

Nikoloudis, D., et al., Jul. 2014, A complete, multi-level conformational clustering of antibody complementarity-determining regions, PeerJ 2:e456; DOI 10.7717/peerj.456, pp. 1-40.*

Baskar et al. (1996) "The enhancer domain of the human cytomegalovirus major immediate-early promoter determines cell type-specific expression in transgenic mice," J. Virology. 70:3207-3214.

Brady et al. (1984) "New cosmid vectors developed for eukaryotic DNA cloning," Gene. 27(2):223-232.

Burt (2012) "Chikungunya: a re-emerging virus," Lancet. 379:662-671.

Caron et al. (1992) "Engineered humanized dimeric forms of IgG are more effective antibodies," J. Exp. Med. 176(4):1191-1195.

Dondelinger et al., "Understanding the Significance and Implications of Antibody Numbering and Antigen-Binding Surface/Residue Definition", Frontiers in Immunology, Oct. 2018, 9(2278): 1-15.

Edge et al. (1981) "Deglycosylation of glycoproteins by trifluoromethanesulfonic acid," Anal. Biochem. 118(1):131-137.

Fox et al. (Nov. 6, 2015) "Broadly Neutralizing Alphavirus Antibodies Bind an Epitope on E2 and Inhibit Entry and Egress," Cell. 163:1095-1107.

Genbank Database [Online] (Dec. 14, 2011) "Chikungunya virus strain SL15649, complete genome," Accession No. GU189061.1. National Center for Biotechnology Information. Accessible on the Internet at URL: https://www.ncbi.nlm.nih.gov/nuccore/270311617, 5 pgs. [Last Accessed Dec. 26, 2017].

Genbank Database [Online] (Dec. 28, 2010) "Chikungunya virus strain IbH35, complete genome," Accession No. HM045786.1. National Center for Biotechnology Information. Accessible on the Internet at URL: https://www.ncbi.nlm.nih.gov/nuccore/HM045786.1, 5 pgs. [Last Accessed Dec. 26, 2017].

Genbank Database [Online] (Dec. 28, 2010) "Chikungunya virus strain RSU1, complete genome," Accession No. HM045797.1. National Center for Biotechnology Information. Accessible on the Internet at URL: https://www.ncbi.nlm.nih.gov/nuccore/296124515, 5 pgs. [Last Accessed Dec. 26, 2017].

Genbank Database [Online] (Jan. 14, 2003) "Chikungunya virus strain S27-African prototype, complete genome," Accession No. AF369024.2. National Center for Biotechnology Information. Accessible on the Internet at URL: https://www.ncbi.nlm.nih.gov/nuccore/AF369024.2, 5 pgs. [Last Accessed Dec. 26, 2017].

Genbank Database [Online] (Jun. 27, 2012) "Chikungunya virus, complete genome," Accession No. NC_004162.2. National Center for Biotechnology Information. Accessible on the Internet at URL: https://www.ncbi.nlm.nih.gov/nuccore/NC_004162.2, 6 pgs. [Last Accessed Dec. 26, 2017].

Genbank Database [Online] (Oct. 24, 2006) "Chikungunya virus strain LR2006_OPY1, complete genome," Accession No. DQ443544.2. National Center for Biotechnology Information. Accessible on the Internet at URL: https://www.ncbi.nlm.nih.gov/nuccore/DQ443544.2, 5 pgs. [Last Accessed Dec. 26, 2017].

Genbank Database [Online] (Sep. 11, 2014) "Chikungunya virus strain 99659, complete genome," Accession No. KJ451624. National Center for Biotechnology Information. Accessible on the Internet at URL: https://www.ncbi.nlm.nih.gov/nuccore/KJ451624, 5 pgs. [Last Accessed Dec. 26, 2017].

Gillies et al. (1983) "A tissue-specific transcription enhancer element is located in the major intron of a rearranged immunoglobulin heavy chain gene," Cell. 33:717-728.

Goh et al., "Neutralizing monoclonal antibodies to the E2 protein of chikungunya virus protects against disease in a mouse model", Clinical Immunology, Dec. 2013, 149(3): 487-497.

Harmsen et al. (2007) "Properties, production, and applications of camelid single-domain antibody fragments," Appl. Microbiol. Biotechnol. 77(1):13-22.

International Search Report and Written Opinion for PCT International Patent Application No. PCT/EP2017/076792 mailed Jan. 24, 2018.

Irani et al., "Molecular properties of human IgG subclasses and their implications for designing therapeutic monoclonal antibodies against infectious diseases", Molecular Immunology, Oct. 2015, 67: 171-182.

Ko et al., "Enhanced neonatal Fc receptor function improves protection against primate SHIV Infection", Nature, Oct. 2014, 514: 642-647.

Kuwana et al. (1987) "Expression of chimeric receptor composed of immunoglobulin-derived V regions and T-cell receptor-derived C regions," Biochem. Biophys. Res. Commun. 149:960-968.

Lefranc et al. (2003) "IMGT unique numbering for immunoglobulin and T cell receptor variable domains and Ig superfamily V-like domains," Dev. Comp. Immunol. 27(1):55-77.

Liu et al., "Fine mapping of the antigen-antibody interaction of scFv215, a recombinant antibody inhibiting RNA polymerase II from *Drosophila melanogaster*", J. Mol. Recog., 1999, 12: 103-111.

Mason et al. (1985) "Transcription cell type specificity is conferred by an immunoglobulin VH gene promoter that includes a functional consensus sequence," Cell. 41:479-487.

Miyaji et al. (1990) "Efficient expression of human beta-interferon in Namalwa KJM-1 cells adapted to serum-free medium by a dhfr gene coamplification method," Cytotechnology. 4:173-180.

Miyaji et al. (1990) "Expression of human beta-interferon in Namalwa KJM-1 which was adapted to serum-free medium," Cytotechnology. 3(2):133-140.

Mizukami et al. (1987) "A new SV40-based vector developed for cDNA expression in animal cells," J. Biochem. 101(5):1307-1310.

Morrison et al. (1984) "Transfer and expression of immunoglobulin genes," Annu. Rev. Immunol. 2:239-256.

Needleman et al. (1970) "A general method applicable to the search for similarities in the amino acid sequence of two proteins," J. Mol. Biol. 48:443-53.

Nikoloudis et al., "A complete, multi-level conformational clustering of antibody complementarity-determining regions", Peer J., Jul. 2014, e456: 1-40.

O'Hare et al. (1981) "Transformation of mouse fibroblasts to methotrexate resistance by a recombinant plasmid expressing a prokaryotic dihydrofolate reductase," Proc. Natl. Acad. Sci. USA. 78(3):1527-1531.

(56) References Cited

OTHER PUBLICATIONS

Osol et al. (1975) Remington's Pharmaceutical Sciences. 15th Ed. Mack Publishing Co., Easton, Pennsylvania. pp. 1035-1038, 1570-1580.
Pal et al. (Apr. 18, 2013) "Development of a highly protective combination monoclonal antibody therapy against Chikungunya virus," PLoS Pathog. 9(4):e1003312. pp. 1-16.
Powers et al. (2007) "Changing patterns of chikungunya virus: re-emergence of a zoonotic arbovirus," J. Gen. Virol. 88:2363-2377.
Rezza et al. (2007) "Infection with chikungunya virus in Italy: an outbreak in a temperate region," Lancet. 370:1840-1846.
Schuffenecker et al. (2006) "Genome microevolution of chikungunya viruses causing the Indian Ocean outbreak," PLoS Med. 3:e263. pp. 1-13.
Sela-Culang et al., "The structural basis of antibody-antigen recognition", Front. Immunol. Oct. 2013, 4(302): 1-13.
Shitara et al. (1994) "A new vector for the high level expression of chimeric antibodies in myeloma cells," J. Immunol. Methods. 167(1-2):271-8.
Shopes (1992) "A genetically engineered human IgG mutant with enhanced cytolytic activity," J. Immunol. 148(9):2918-2922.
Smith et al. (2015) "Isolation and Characterization of Broad and Ultrapotent Human Monoclonal Antibodies with Therapeutic Activity against Chikungunya Virus," Cell Host & Microbe. 18:86-95.
Sojar et al. (1987) "A chemical method for the deglycosylation of proteins," Arch. Biochem. Biophys. 259(1):52-57.
Strohl (2009) "Optimization of Fc-mediated effector functions of monoclonal antibodies," Current Opinion in Biotechnology. 20:685-691.
Thotakura et al. (1987) "Enzymatic deglycosylation of glycoproteins," Methods Enzymol. 138:350-359.
Tsetsarkin et al. (2007) "A single mutation in chikungunya virus affects vector specificity and epidemic potential," PLoS Pathog. 3:e201. pp. 1-12.
Uniprot Database [Online] (Last modified Jul. 27, 2011) "UniProtKB-Q8JUX5 (POLS_CHIKS)," Accession No. Q8JUX5. UniProt Consortium. Accessible on the Internet at URL: http://www.uniprot.org/uniprot/Q8JUX5, 12 pgs. [Last Accessed Dec. 26, 2017].
Urlaub et al. (1980) "Isolation of Chinese hamster cell mutants deficient in dihydrofolate reductase activity," Proc. Natl. Acad. Sci. USA. 77(7):4216-4220.
Vidarsson et al. (2014) "IgG Subclasses and Allotypes: From Structure to Effector Functions," Frontiers in Immunology, vol. 5, Oct. 20, 2014 (Oct. 20, 2014), 17 pp.
Voss et al. (2010) "Glycoprotein organization of Chikungunya virus particles revealed by X-ray crystallography," Nature. 468:709-712.
Warter et al. (2011) "Chikungunya Virus Envelope-Specific Human Monoclonal Antibodies with Broad Neutralization Potency," The Journal of Immunology, vol. 186, No. 5, pp. 3258-3264.
Winkler et al., "Changing the antigen binding specifically by single point mutations of an anti-p24 (HIV-1) antibody", J. Immunol., 2000, 165: 4505-4514.
Wu et al. (Jun. 2, 2013) "Chikungunya virus with E1-A226V mutation causing two outbreaks in 2010, Guangdong, China," Virol. J. 10:174.
Xiang et al., "Light-chain framework region residue Tyr71 of chimeric B72.3 antibody plays an important role in influencing the TAG72 antigen binding", Prot. Engineer., 1999, 12(5): 417-421.
Zalevsky et al. (2010) "Enhanced antibody half-life improves in vivo activity," Nature Biotechnology, 28(2):157-159.
U.S. Appl. No. 15/787,647 2018/0127487 U.S. Pat. No. 11,286,295, filed Oct. 20, 2016 May 10, 2018 Mar. 29, 2022, Kara Carter, Anti-CHIKV Monoclonal Antibodies Directed Against The E2 Structural Protein.
Brown et al, Tolerance to Single, but Not Multiple, Amino Acid Replacements in Antibody VH CDR2, J. Immunol., 1996, 156: 3285-329.

* cited by examiner

SEQ ID NO: 55

```
IgG1_Fc_region_YTE_SEQ_ID_NO:62    CPPCPAPELLGGPSVFLFPPKPKDTLYITREPEVTCVVVDVSHEDPEVKFNWYVDGVEVH
IgG1_Fc_region_QL_SEQ_ID_NO:61     CPPCPAPELLGGPSVFLFPPKPKDQLMISRTPEVTCVVVDVSHEDPEVKFNWYVDGVEVH
IgG1_Fc_region_AAA_SEQ_ID_NO:60    CPPCPAPELLGGPSVFLFPPKPKDTLMISRTPEVTCVVVDVSHEDPEVKFNWYVDGVEVH
IgG1_Fc_region_SEQ_ID_NO:17        CPPCPAPELLGGPSVFLFPPKPKDTLMISRTPEVTCVVVDVSHEDPEVKFNWYVDGVEVH
IgG1_Fc_region_A_SEQ_ID_NO:59      CPPCPAPELLGGPSVFLFPPKPKDTLMISRTPEVTCVVVDVSHEDPEVKFNWYVDGVEVH
IgG1_Fc_region_LS_SEQ_ID_NO:63     CPPCPAPELLGGPSVFLFPPKPKDTLMISRTPEVTCVVVDVSHEDPEVKFNWYVDGVEVH
                                   ************************ * *:* *****************************

IgG1_Fc_region_YTE_SEQ_ID_NO:62    NAKTKPREEQYNSTYRVVSVLTVLHQDWLNGKEYKCKVSNKALPAPIEKTISKAKGQPRE
IgG1_Fc_region_QL_SEQ_ID_NO:61     NAKTKPREEQYNSTYRVVSVLTVLHQDWLNGKEYKCKVSNKALPAPIEKTISKAKGQPRE
IgG1_Fc_region_AAA_SEQ_ID_NO:60    NAKTKPREEQYNSTYRVVSVLAVLHQDWLNGKEYKCKVSNKALPAPIEKTISKAKGQPRE
IgG1_Fc_region_SEQ_ID_NO:17        NAKTKPREEQYNSTYRVVSVLTVLHQDWLNGKEYKCKVSNKALPAPIEKTISKAKGQPRE
IgG1_Fc_region_A_SEQ_ID_NO:59      NAKTKPREEQYNSTYRVVSVLTVLHQDWLNGKEYKCKVSNKALPAPIEKTISKAKGQPRE
IgG1_Fc_region_LS_SEQ_ID_NO:63     NAKTKPREEQYNSTYRVVSVLTVLHQDWLNGKEYKCKVSNKALPAPIEKTISKAKGQPRE
                                   *********************:**************************************

IgG1_Fc_region_YTE_SEQ_ID_NO:62    PQVYTLPPSRDELTKNQVSLTCLVKGFYPSDIAVEWESNGQPENNYKTTPPVLDSDGSFF
IgG1_Fc_region_QL_SEQ_ID_NO:61     PQVYTLPPSRDELTKNQVSLTCLVKGFYPSDIAVEWESNGQPENNYKTTPPVLDSDGSFF
IgG1_Fc_region_AAA_SEQ_ID_NO:60    PQVYTLPPSRDELTKNQVSLTCLVKGFYPSDIAVAWESNGQPENNYKTTPPVLDSDGSFF
IgG1_Fc_region_SEQ_ID_NO:17        PQVYTLPPSRDELTKNQVSLTCLVKGFYPSDIAVEWESNGQPENNYKTTPPVLDSDGSFF
IgG1_Fc_region_A_SEQ_ID_NO:59      PQVYTLPPSRDELTKNQVSLTCLVKGFYPSDIAVEWESNGQPENNYKTTPPVLDSDGSFF
IgG1_Fc_region_LS_SEQ_ID_NO:63     PQVYTLPPSRDELTKNQVSLTCLVKGFYPSDIAVEWESNGQPENNYKTTPPVLDSDGSFF
                                   ********************************** *************************

IgG1_Fc_region_YTE_SEQ_ID_NO:62    LYSKLTVDKSRWQQGNVFSCSVMHEALHNHYTQKSLSLSPG
IgG1_Fc_region_QL_SEQ_ID_NO:61     LYSKLTVDKSRWQQGNVFSCSVLHEALHNHYTQKSLSLSPG
IgG1_Fc_region_AAA_SEQ_ID_NO:60    LYSKLTVDKSRWQQGNVFSCSVMHEALHAHYTQKSLSLSPG
IgG1_Fc_region_SEQ_ID_NO:17        LYSKLTVDKSRWQQGNVFSCSVMHEALHNHYTQKSLSLSPG
IgG1_Fc_region_A_SEQ_ID_NO:59      LYSKLTVDKSRWQQGNVFSCSVMHEALHAHYTQKSLSLSPG
IgG1_Fc_region_LS_SEQ_ID_NO:63     LYSKLTVDKSRWQQGNVFSCSVLHEALHSHYTQKSLSLSPG
                                   **********************:***** ************
```

Figure 2

ANTI-CHIKV ANTIBODIES AND USES THEREOF

CROSS-REFERENCE TO RELATED APPLICATION

This application is a division of U.S. patent application Ser. No. 15/787,647, filed Oct. 18, 2017, which claims the benefit of European Patent Application No. 16306374.6, filed Oct. 20, 2016, the entire contents of which are hereby incorporated herein by reference.

THE NAMES OF THE PARTIES TO A JOINT RESEARCH AGREEMENT

Sanofi Aventis Recherche & Développement, a Sanofi subsidiary, and Vanderbilt University are the parties to a Joint Research Agreement. The claimed invention was made as a result of activities undertaken within the scope of the Joint Research Agreement.

TECHNICAL FIELD

The present invention concerns antibodies and antigen-binding fragments of antibodies which specifically bind to and neutralize Chikungunya virus (CHIKV) and which are engineered to develop prophylactic and therapeutic solutions for preventing and treating CHIKV disease. The invention also relates to pharmaceutical compositions comprising CHIKV neutralizing antibodies and the use of the antibodies for the prevention and treatment of CHIKV disease.

BACKGROUND

CHIKV is a reemerging mosquito-borne pathogen. CHIKV is endemic in Africa, India and Southeast Asia but also occurs in unpredictable and large outbreaks with high attack rates beyond these regions, infecting millions of people (Powers A M, Logue C H, 2007, J. Gen. Virol. 88:2363-2377). A mutation in the CHIKV envelope glycoprotein 1 (E1) enabled viral transmission through Aedes albopictus mosquitoes, in addition to Aedes aegypti mosquitoes and resulted in 2005 in widespread and severe epidemics in La Reunion, India and Indonesia, with subsequent traveler-initiated outbreaks occurring in Italy, France and China (Tsetsarkin K A et al 2007, PLoS Pathog. 3: e201; Schuffenecker I et al 2006, PLoS Med. 3: e263; Wu D, Zhang Y et al 2013, Virol. J. 10:174; Rezza G et al 2007, Lancet 370:1840-1846; Burt F J 2012, Lancet 379:662-671). Due to the extended geographic range of Aedes albopictus mosquitoes, the virus is expected to spread to new areas and Europe and the Americas are now at risk of CHIKV outbreaks.

CHIKV is an enveloped positive strand RNA virus of the alphavirus genus of the Togaviridae family. It is a member of the Semliki Forest virus complex and is closely related to Ross River virus and O'nyong'nyong virus (ONNV); because it is transmitted by arthropods, namely mosquitoes, it can also be referred to as an arbovirus (ARthropod-Borne virus).

CHIKV enters cells via receptor-mediated internalization and a low pH-triggered type II membrane fusion event in early endosomes. CHIKV disease is characterized by acute, post-acute and chronic polyarthritis/polyarthralgia phases, the latter of which is usually symmetric and often incapacitating and can last for months or years. Other symptoms, such as fever, rash, myalgia and/or fatigue are also present during the acute phase. Recent epidemic was also associated with atypical and severe clinical forms of CHIKV disease and some fatalities, which appeared to be restricted to the very young and elderly patients with comorbidities.

There are currently no specific prophylactic or therapeutic treatments for CHIKV disease. CHIKV is treated symptomatically, usually with bed rest, fluids and medicines to relieve symptoms of fever and aching such as simple analgesics and/or non-sterodial anti-inflammatory drugs (NSAID). Although vaccine candidate against CHIKV were first proposed 45 years ago, many vaccine candidates tested to date have ever failed to induce protective antibodies or demonstrated significant safety issues.

There is still a need for treatments showing increased therapeutic efficacies against CHIKV, including the use of specific monoclonal antibodies targeting CHIKV. There is a need in the art for CHIKV neutralizing antibodies suitable for prophylactic and therapeutic uses. In particular, such antibodies need to properly neutralize different strains of the CHIK virus with a high target binding affinity, to exhibit appropriate pharmacokinetic parameters, to display appropriate half-life upon administration, and to allow efficient manufacturing at large scale, while retaining their binding to FcγRIIIa that is associated with effector functions.

SUMMARY OF THE INVENTION

As disclosed in the present invention, inventors of the present application were able to select and to engineer specific CHIKV neutralizing antibodies improved in their exposure-related pharmacokinetics and maintaining their binding to FcγRIIIa that is associated with effector functions, making them compatible with a development of therapeutics to prevent and treat CHIKV disease and addressing the need in the art for effective therapies against CHIKV.

Antibodies of the invention have a high binding affinity (within the nanomolar range) toward different CHIKV strains. Hence, they display broad and ultrapotent neutralizing activities against different CHIKV strains. Furthermore, antibodies of the present invention have improved binding to human FcRn receptor while retaining FcγRIIIa binding making them compatible with an increased half-life while maintaining their binding to FcγRIIIa that is associated with effector functions.

In a first aspect, the present invention relates to an isolated monoclonal antibody that binds to CHIKV and that comprises three Heavy Chain Complementary Determining Regions (CDRHs) and three Light Chain Complementary Determining Regions (CDRLs), wherein:

i. said CDRHs have amino acid sequences of SEQ ID NO: 5, 6 and 7, and said CDRLs have amino acid sequences of SEQ ID NO: 8, GNT and 10, or ii. said CDRHs have amino acid sequences of SEQ ID NO: 11, 12 and 13, and said CDRLs have amino acid sequences of SEQ ID NO: 14, GTS and 16, or iii. said CDRHs and CDRLHs have amino acid sequences differing from the sequences of i. or ii. by one or two amino acid substitutions;

and wherein said antibody further comprises a Fc region comprising at least one residue selected from the group consisting of:

iv. an alanine at position 434, or v. an alanine at positions 307, 380 and 434, respectively, or vi. a glutamine at position 250 and a leucine at position 428, respectively, or vii. a leucine at position 428 and a serine at position 434, respectively, or viii. a tyrosine at position 252, a threonine at position 254 and a glutamic acid at position 256, respectively, wherein said amino acid positions are given according to the EU index.

In one embodiment, the isolated monoclonal antibody binds to CHIKV and comprises three Heavy Chain Complementary Determining Regions (CDRHs) and three Light Chain Complementary Determining Regions (CDRLs), wherein:

i. said CDRHs have amino acid sequences of SEQ ID NO: 5, 6 and 7, and said CDRLs have amino acid sequences of SEQ ID NO: 8, GNT and 10, or ii. said CDRHs have amino acid sequences of SEQ ID NO: 11, 12 and 13, and said CDRLs have amino acid sequences of SEQ ID NO: 14, GTS and 16, or iii. said CDRHs and CDRLHs have amino acid sequences differing from the sequences of i. or ii. by one or two amino acid substitutions;

and wherein said antibody further comprises a Fc region comprising at least one residue selected from the group consisting of:

iv. an alanine at position 434, or v. an alanine at positions 307, 380 and 434, respectively, or vi. a glutamine at position 250 and a leucine at position 428, respectively, or vii. a leucine at position 428 and a serine at position 434, respectively, or viii. a tyrosine at position 252, a threonine at position 254 and a glutamic acid at position 256, respectively, wherein said amino acid positions are given according to the EU index;

and wherein the antibody has one or more of the following properties:

ix. binds a CHIKV pE2-E1 target with a binding dissociation equilibrium constant ($K_D$) of less than about 10 nM;

x. binds human FcRn with a $K_D$ of less than about 200 nM;

xi. binds human FcγRIII with a $K_D$ of less than about 600 nM.

In another embodiment, the monoclonal antibody comprises three Heavy Chain Complementary Determining Regions (CDRHs) having amino acid sequences of SEQ ID NO: 5, 6 and 7, respectively, or amino acid sequences differing from those sequences by one or two amino acid substitutions, and said antibody comprises three Light Chain Complementary Determining Regions (CDRLs) having amino acid sequences of SEQ ID NO: 8, GNT and 10, respectively, or amino acid sequences differing from those sequences by one or two amino acid substitutions.

In another embodiment, the monoclonal antibody comprises:

A CDRH1 consisting of sequence SEQ ID NO: 5;

A CDRH2 consisting of sequence SEQ ID NO: 6;

A CDRH3 consisting of sequence SEQ ID NO: 7;

A CDRL1 consisting of sequence SEQ ID NO: 8;

A CDRL2 consisting of sequence GNT;

A CDRL3 consisting of sequence SEQ ID NO: 10.

In a further embodiment, the monoclonal antibody comprises three Heavy Chain Complementary Determining Regions (CDRHs) having amino acid sequences of SEQ ID NO: 11, 12 and 13, respectively, or amino acid sequences differing from those sequences by one or two amino acid substitutions, and said antibody comprises three Light Chain Complementary Determining Regions (CDRLs) having amino acid sequences of SEQ ID NO: 14, GTS and 16, respectively, or amino acid sequences differing from those sequences by one or two amino acid substitutions.

In another embodiment, the monoclonal antibody comprises:

A CDRH1 consisting of sequence SEQ ID NO: 11;

A CDRH2 consisting of sequence SEQ ID NO: 12;

A CDRH3 consisting of sequence SEQ ID NO: 13;

A CDRL1 consisting of sequence SEQ ID NO: 14;

A CDRL2 consisting of GTS;

A CDRL3 consisting of sequence SEQ ID NO: 16.

In another embodiment, the monoclonal antibody comprises a Fc region that comprises residues selected from the group consisting of:

i. a leucine at position 428 and a serine at position 434, or ii. a tyrosine at position 252, a threonine at position 254 and a glutamic acid at position 256, respectively, wherein said amino acid positions are given according to the EU index.

In a further embodiment, the monoclonal antibody comprises a Fc region wherein said Fc region comprises a leucine at position 428 and a serine at position 434 wherein said amino acid positions are given according to the EU index.

In another embodiment, the monoclonal antibody comprises a kappa light chain or lambda light chain.

In another embodiment, the monoclonal antibody has a Fc region that comprises or consists of a sequence having at least 80% identity with SEQ ID NO: 59, 60, 61, 62 and 63.

In another embodiment, the monoclonal antibody has a variable region of its heavy chain that comprises or consists of a sequence having at least 80% identity with sequence ID NO: 1.

In another embodiment, the monoclonal antibody has a variable region of its light chain that comprises or consists of a sequence having at least 80% identity with sequence ID NO: 2.

In another embodiment, the monoclonal antibody has a heavy chain that comprises or consists of a sequence having at least 80% identity with sequence ID NO: 31.

In another embodiment, the monoclonal antibody has a light chain that comprises or consists of a sequence having at least 80% identity with sequence ID NO: 20.

In a second aspect, the isolated monoclonal antibody binds to CHIKV, or an antigen-binding fragment thereof, wherein said antibody or antigen-binding fragment thereof comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and wherein said antibody or antigen-binding fragment thereof further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, and/or ii. the amino acid at position 12 of SEQ ID NO: 33 is not N; and/or iii. the amino acid at position 13 of SEQ ID NO: 33 is not G.

In one embodiment, the monoclonal antibody or antigen-binding fragment thereof comprises:

A CDRH1 consisting of sequence SEQ ID NO: 11;

A CDRH2 consisting of sequence SEQ ID NO: 12;
A CDRH3 consisting of sequence SEQ ID NO: 33;
A CDRL1 consisting of sequence SEQ ID NO: 14;
A CDRL2 consisting of GTS;
A CDRL3 consisting of sequence SEQ ID NO: 16, and wherein:

i. the amino acid at position 8 of SEQ ID NO: 33 is not M, and/or
ii. the amino acid at position 12 of SEQ ID NO: 33 is not N; and/or
iii. the amino acid at position 13 of SEQ ID NO: 33 is not G.

In another embodiment, the monoclonal antibody or antigen-binding fragment thereof comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and said antibody or antigen-binding fragment thereof further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, or
ii. the amino acid at position 12 of SEQ ID NO: 33 is not N; or
iii. the amino acid at position 13 of SEQ ID NO: 33 is not G.

In another embodiment, the isolated monoclonal antibody or antigen-binding fragment thereof comprises three Heavy Chain Complementary Determining Regions (CDRHs) having amino acid sequences of SEQ ID NO: 11, 12 and 33, respectively and said antibody or antigen-binding fragment thereof further comprises three Light Chain Complementary Determining Regions (CDRLs) having amino acid sequences of SEQ ID NO: 14, GTS and 16, respectively, and wherein:

i. the amino acid at position 8 of SEQ ID NO: 33 is not M, or
ii. the amino acid at position 12 of SEQ ID NO: 33 is not N; or
iii. the amino acid at position 13 of SEQ ID NO: 33 is not G.

In another embodiment, the monoclonal antibody or antigen-binding fragment thereof comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and said antibody or antigen-binding fragment thereof further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, or
ii. the amino acid at position 12 of SEQ ID NO: 33 is not N; or
iii. the amino acid at position 13 of SEQ ID NO: 33 is not G, and wherein the antibody has one or more of the following properties:

iv. binds a CHIKV pE2-E1 target with a binding dissociation equilibrium constant ($K_D$) of less than about 10 nM;
v. binds human FcRn with a $K_D$ of less than about 200 nM;
vi. binds human FcγRIII with a $K_D$ of less than about 600 nM.

In another embodiment, the monoclonal antibody comprises an amino acid at position 8 of SEQ ID NO: 33 selected from the group consisting of I, L, V, Q and N.

In another embodiment, the monoclonal antibody comprises:

A CDRH1 consisting of sequence SEQ ID NO: 11;
A CDRH2 consisting of sequence SEQ ID NO: 12;
A CDRH3 consisting of sequence SEQ ID NO: 34;
A CDRL1 consisting of sequence SEQ ID NO: 14;
A CDRL2 consisting of GTS;
A CDRL3 consisting of sequence SEQ ID NO: 16.

In another embodiment, the monoclonal antibody comprises an amino acid at position 12 of SEQ ID NO: 33 selected from the group consisting of Q, E, S, T and D.

In a further embodiment, the monoclonal antibody comprises:

A CDRH1 consisting of sequence SEQ ID NO: 11;
A CDRH2 consisting of sequence SEQ ID NO: 12;
A CDRH3 consisting of sequence SEQ ID NO: 35;
A CDRL1 consisting of sequence SEQ ID NO: 14;
A CDRL2 consisting of GTS;
A CDRL3 consisting of sequence SEQ ID NO: 16.

In another embodiment, the monoclonal antibody comprises an amino acid at position 13 of SEQ ID NO: 33 selected from the group consisting of A, S and T.

In a further embodiment, the monoclonal antibody comprises:

A CDRH1 consisting of sequence SEQ ID NO: 11;
A CDRH2 consisting of sequence SEQ ID NO: 12;
A CDRH3 consisting of sequence SEQ ID NO: 36;
A CDRL1 consisting of sequence SEQ ID NO: 14;
A CDRL2 consisting of GTS;
A CDRL3 consisting of sequence SEQ ID NO: 16.

In another embodiment, the monoclonal antibody has a variable region of its heavy chain that comprises or consists of a sequence having at least 80% identity with sequence ID NO: 57.

In another embodiment, the monoclonal antibody has a variable region of its light chain that comprises or consists of a sequence having at least 80% identity with sequence ID NO: 4.

In another embodiment, the monoclonal antibody has its heavy chain that comprises or consists of a sequence having at least 80% identity with sequence ID NO: 47.

In another embodiment, the monoclonal antibody has a light chain that comprises or consists of a sequence having at least 80% identity with sequence ID NO: 38.

In another aspect of this second aspect, the monoclonal antibody further comprises a Fc region that comprises residues selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In another embodiment, the monoclonal antibody has a Fc region that comprises residues selected from the group consisting of:

i. a leucine at position 428 and a serine at position 434 or ii. a tyrosine at position 252, a threonine at position 254 and a glutamic acid at position 256, wherein said amino acid positions are given according to the EU index.

In another embodiment, the monoclonal antibody has a Fc region that comprises a leucine at position 428 and a serine at position 434 wherein said amino acid positions are given according to the EU index.

In another embodiment of this aspect of the invention, the monoclonal antibody comprises a kappa light chain or a lambda light chain.

In another embodiment, the monoclonal antibody has a Fc region comprising or consisting of a sequence having at least 80% identity with SEQ ID NO: 59, 60, 61, 62 and 63.

In another embodiment, the monoclonal antibody has a variable region of its heavy chain that comprises or consists of a sequence having at least 80% identity with sequence ID NO: 57.

In another embodiment, the monoclonal antibody has a variable region of its light chain that comprises or consists of a sequence having at least 80% identity with sequence ID NO: 4.

In another embodiment, the monoclonal antibody has a heavy chain that comprises or consists of a sequence having at least 80% identity with sequence ID NO: 53.

In another embodiment, the monoclonal antibody has a light chain that comprises or consists of a sequence having at least 80% identity with sequence ID NO: 38.

In a fourth aspect, the invention relates to the monoclonal antibody for use as a medicament.

In another embodiment, the monoclonal is for use in the treatment of CHIKV-associated arthralgia.

In another embodiment, the monoclonal antibody is for use in the prevention of CHIKV infection.

In a fifth aspect, the invention relates to a pharmaceutical composition that comprises the monoclonal antibody and at least one excipient.

In a sixth aspect, the invention relates to a cell line producing the monoclonal antibody.

In a seventh aspect, is a method of producing the monoclonal antibody, wherein said method comprises the steps of (i) culturing a cell line according to the sixth aspect; (ii) purifying the produced monoclonal antibody; and optionally (iii) formulating said monoclonal antibody into a pharmaceutical composition.

In an eighth aspect, the invention relates to a polynucleotide comprising a sequence encoding an antibody or an antigen-binding fragment thereof as featured herein. In one embodiment, the polynucleotide encodes a polypeptide having at least 80% identity with one of the sequences SEQ ID NO: 18, 21, 22, 24, 26, 28, 30, 32, 39, 40, 42, 44, 46, 48, 50, 52 and 54. In one embodiment, the polynucleotide is characterized in that it has a sequence having at least 80% identity with one of the sequences SEQ ID NO: 18, 21, 22, 24, 26, 28, 30, 32, 39, 40, 42, 44, 46, 48, 50, 52 and 54.

In a ninth aspect, the invention relates to a kit comprising at least one antibody as featured herein. In one embodiment, said kit optionally comprises packaging material.

BRIEF DESCRIPTION OF THE FIGURES

FIG. 2: IgG1 Fc region sequence alignment: SEQ ID NO: 17; SEQ ID NO: 59; SEQ ID NO: 60; SEQ ID NO: 61; SEQ ID NO: 62 and SEQ ID NO: 63.

DETAILED DESCRIPTION OF THE INVENTION

Definitions

Figure 1:
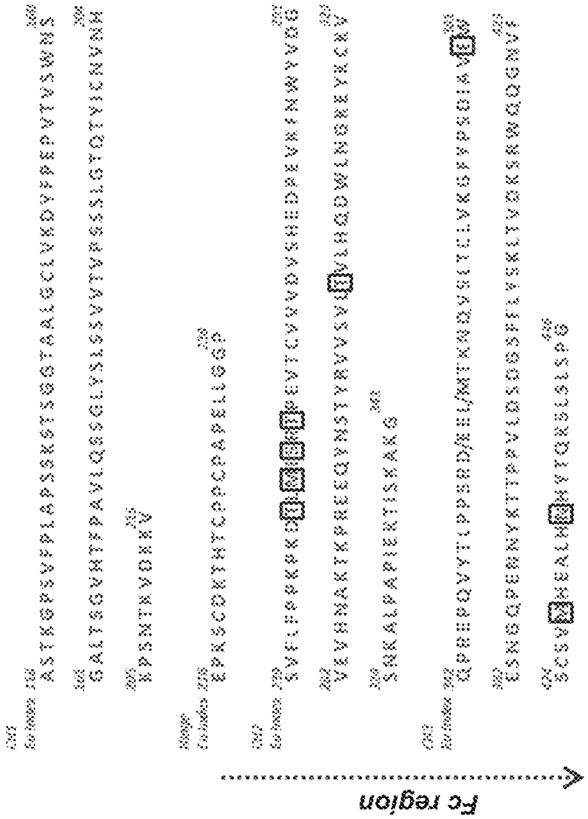
FIG. 1: Human IgG1 heavy chain amino acid sequence of CH1, hinge, CH2 and CH3 regions; part of the hinge and CH2 and CH3 regions constitute the Fc region. Numbering of the amino acid residues is according to the EU index as set forth in Kabat (Kabat et al., Sequences of Proteins of Immunological Interest, 5th, Ed. Public Health Service, National Institutes of Health, Bethesda, Md. (1991). Substituted residues of the Fc region featured in the invention are squared.

An "antibody" may be a natural or conventional antibody in which two heavy chains are linked to each other by disulfide bonds and each heavy chain is linked to a light chain by a disulfide bond. In mammals, antibodies are classified into five main classes or isotypes, IgA, IgD, IgE, IgG and IgM. They are classed according to the heavy chain they contain, alpha, delta, epsilon, gamma or mu, respectively. These differ in the sequence and number of constant domains, hinge structure and the valency of the antibody. There are two types of light chain, lambda (l) and kappa (k) with kappa light chains being the more common of the two. Although these are relatively dissimilar in protein sequence they share a similar structure and function.

The five main heavy chain classes (or isotypes) determine the functional activity of an antibody molecule: IgM, IgD, IgG, IgA and IgE. Each chain contains distinct sequence domains. IgG is the most abundant antibody in norm human serum, accounting for 70-85% of the total immunoglobulin pool. It is monomeric with a molecular weight of approximately 150 kDa, is the major antibody of the secondary immune response and has the longest half-life of the five immunoglobulin classes. IgG consists of four human subclasses (IgG1, IgG2, IgG3 and IgG4) each containing a different heavy chain. They are highly homologous and differ mainly in the hinge region and the extent to which they activate the host immune system. IgG1 and IgG4 contain two inter-chain disulphide bonds in the hinge region, IgG2 has 4 and IgG3 has 11.

The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. "Complementarity Determining Regions or CDRs" refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L (for Light Chain Complementary Determining Regions) or CDRL1, CDRL2, CDRL3 and CDR1-H, CDR2-H, CDR3-H (for Heavy Chain Complementary Determining Regions) or CDRH1, CDRH2, CDRH3, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

In one embodiment, CDR/FR definition in an immunoglobulin light or heavy chain is to be determined based on IMGT definition (Lefranc, M. P. et al., 2003, Dev Comp Immunol. 27 (1): 55-77; imgt.org). CDR sequences featured in the invention are given according to IMGT's nomenclature.

As used herein, the term "antibody" refers to conventional or full-length antibodies (i.e. antibodies comprising two heavy chains and two light chains), to single domain antibodies, and to fragments of conventional and of single domain antibodies. As used herein, the term "antibody" includes but is not limited to chimeric antibodies, humanized antibodies, human antibodies, and multispecific antibodies (such as e.g. bispecific and trispecific antibodies). The term "antibody" refers both to an antibody comprising the signal peptide (or pro-peptide, if any), and to the mature form obtained upon secretion and proteolytic processing of the chain(s).

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1): 13-22).

As used herein, an "isolated antibody" refers to an antibody that is mainly free of other antibodies having different antigenic specificities; for example, an isolated antibody that binds to CHIKV, or a fragment thereof, or an antigen-binding fragment thereof, is mainly free of antibodies that specifically bind antigens other than CHIKV.

A "blocking antibody" or a "neutralizing antibody", or an "antibody that neutralizes CHIKV activity", or an "antibody that exhibits/displays neutralizing activity against CHIKV", or a "CHIKV neutralizing antibody" or an "anti-CHIKV antibody" as used herein, refers to an antibody whose binding to CHIKV results in inhibition of at least one biological activity of CHIKV. For example, an antibody may neutralize a CHIKV strain by blocking CHIKV attachment to the cells and thereby preventing infection of said cells by CHIKV.

The term "monoclonal antibody" or "mAb" as used herein, refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

The term “chimeric antibody” refers to an engineered antibody which in its broadest sense contains one or more regions from one antibody and one or more regions from one or more other antibody(ies). In particular, a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin The term “humanised antibody” refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

“Fragments” of (conventional) antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of a conventional antibody may also be a single domain antibody, such as a heavy chain antibody or VHH.

The term “Fab” denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term “F(ab')2” refers to an antibody fragment having a molecular weight of about 100,000 and antigen binding activity, which is slightly larger than the Fab bound via a disulfide bond of the hinge region, among fragments obtained by treating IgG with a protease, pepsin.

The term “Fab” refers to an antibody fragment having a molecular weight of about 50,000 and antigen binding activity, which is obtained by cutting a disulfide bond of the hinge region of the F(ab')2.

“Fc region” or “Fc domain” is defined as the carboxyl terminal of the antibodies heavy chains and contains protein sequences common to all immunoglobulins as well as determinants unique to the individual different classes of immunoglobulins. As an example, human IgG1 heavy chain comprises CH1, hinge, CH2 and CH3 regions; part of the hinge and CH2 and CH3 regions constitute the Fc region. As shown in FIG. 1, numbering of the amino acid residues of the Fc region for the purpose of the invention is according the EU index as set forth in Kabat (Kabat et al., Sequences of Proteins of Immunological Interest, 5th, Ed. Public Health Service, National Institutes of Health, Bethesda, Md. (1991). Consequently, the expression “wherein the/said amino acid positions are given according to the EU index” refers to this numbering of the Fc region as set forth above in Kabat et al, 1991 and as shown in FIG. 1.

Domains of this Fc region are central in determining the biological functions of the immunoglobulin and these biological functions are termed “effector functions”. These Fc domain-mediated activities are mediated via immunological effector cells, including B lymphocytes, natural killer cells, macrophages, basophils, neutrophils and mast cells, or various complement components. These effector functions involve activation of receptors on the surface of said effector cells, through the binding of the Fc domain of an antibody to the said receptor (or “Fc receptor”) or to complement component(s). The antibody-dependent cellular cytotoxicity (ADCC), the antibody-dependent cellular phagocytosis (ADCP) and complement-dependent cytotoxicity (CDC) activities belong to these effector functions and involve the binding of the Fc domain to Fc-receptors such as FcγRI (CD64), FcγRII, FcγRIII of the effector cells or complement components such as C1q. Of the various human immunoglobulin classes, human IgG1 and IgG3 mediate ADCC more effectively than IgG2 and IgG4. The term “Fc receptor” includes but is not limited to FcγRI (CD64), FcγRIIA and FcγRIIB (CD32), FcγRIIIA (CD16a) and FcγRIIIB (CD16b), Fcα receptor (FcαRI or CD89) and Fcε receptor (FcεRI and FcεRII (CD23). Several amino acid substitutions have been reported in the literature to lead to the decrease of effector functions in different human IgG isotypes (see Table 2 in Strohl 2009, Current Opinion in Biotechnology 20:685-691).

A single chain Fv (“scFv”) polypeptide is a covalently linked VH::VL heterodimer which is usually expressed from a gene fusion including VH and VL encoding genes linked by a peptide-encoding linker. A human scFv fragment can include CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)2. “dsFv” is a VH::VL heterodimer stabilised by a disulphide bond. “(dsFv)2” denotes two dsFv coupled by a peptide linker.

The term “bispecific antibody” or “BsAb” denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term “multispecific antibody” denotes an antibody which combines the antigen-binding sites of two or more antibodies within a single molecule.

The term “diabodies” refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The term “hybridoma” denotes a cell, which is obtained by subjecting a B cell prepared by immunizing a non-human mammal with an antigen to cell fusion with a myeloma cell derived from a mouse or the like which produces a desired monoclonal antibody having an antigen specificity.

As used herein, “specifically binds” or “binds specifically to” or “binds to” or the like, means that an antibody or antigen-binding fragment thereof forms a complex with an antigen that is relatively stable under physiological conditions. Specific binding can be characterized by an equilibrium dissociation constant ($K_D$) of at least about $1\times10^{-8}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been characterized, for example, by their specific binding to CHIKV and/or CHIKV antigen using surface plasmon resonance, e.g., BIACORE™.

As used herein, "CHIKV antigen" designates specific natural antigens of the antibodies described herein, i.e. protein E2 of CHIKV. It also encompasses recombinant proteins that comprise the CHIKV envelope proteins E1 and the specific antigen E2 of CHIKV, used for example in surface plasmon resonance binding experiments to measure binding affinities of anti-CHIKV antibodies in vitro, as described herein in materials and methods and designated under "pE2-E1 protein" or "pE2-E1 target" or "p62-E1" or "his-tagged CHIKV E2" or "CHIKV target pE2-E1" or "CHIKV pE2-E1 antigen".

As used herein, "acidic environment" means an environment less than pH 7; it is understood that binding experiments done at pH 6 for example leads to binding data in an acidic environment.

A sequence "at least 80% identical to a reference sequence" is a sequence having, on its entire length, 80%, or more, in particular 85%, 90%, 91%, 92%, 93%, 94%, 95%, 96%, 97%, 98% or 99% sequence identity with the entire length of the reference sequence.

A percentage of "sequence identity" may be determined by comparing the two sequences, optimally aligned over a comparison window, wherein the portion of the polynucleotide or polypeptide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison is conducted by global pairwise alignment, e.g. using the algorithm of Needleman and Wunsch J. Mol. Biol. 48: 443 (1970). The percentage of sequence identity can be readily determined for instance using the program Needle, with the BLOSUM62 matrix, and the following parameters gap-open=10, gap-extend=0.5.

A "conservative amino acid substitution" is one in which an amino acid residue is substituted by another amino acid residue having a side chain R group with similar chemical properties (e.g., charge or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acids substitution groups are: valine-leucine-isoleucine, phenylalanine-tyrosine-tryptophane, lysine-arginine, alanine-valine, glutamate-aspartate, and asparagine-glutamine.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to bind to CHIKV and/or CHIKV antigen. Such antigen-binding portions typically comprise the CDRs of the antibody.

"Antibody-dependent cell-mediated cytotoxicity" or "ADCC" refers to a form of cytotoxicity in which secreted antibodies bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. In other words, ADCC is a mechanism of cell-mediated immunity whereby effector cells of the immune system, mainly Natural Killer cells, actively lyse a target cell that has been bound by specific antibodies. ADCC is one of the mechanisms by which antibodies as part of the humoral immune response, can limit and contain infections. To assess ADCC activity of a molecule of interest, an in vitro ADCC assay, such as that described in U.S. Pat. No. 5,500,362 or 5,821,337 was also contemplated.

The expression "amino acid sequence(s) differing from sequences of X or Y by one or two amino acid substitution(s)" means that said sequence differs from sequences X or Y by at most two amino acid substitutions, i.e. differs by only one or two amino acid substitutions.

For example, the expression "a sequence X differing from sequence Y by the amino acid substitution Z and optionally one or two additional amino acid substitution(s)" means that said sequence X differs from sequence Y by:

only the amino acid substitution Z, or the amino acid substitution Z and one or two amino acid substitutions that are (is) different from amino acid substitution Z.

The expression "SEQ ID NO: X with one amino acid substitution at position Y" means a sequence differing from SEQ ID NO: X by one amino acid substitution at position Y of SEQ ID NO: X.

As used herein, "CHIKV" means Chikungunya virus which is an enveloped positive strand RNA virus of the alphavirus genus of the Togaviridae family as described above in the introduction part. Within CHIKV is also encompassed the different representative infectious strains ("CHIKV strains" including but not limited to the East/Central/south African (ECSA) genotype such as LR2006 OPY1 [LR] strain, as an example, having a sequence shown under NCBI Accession Number: DQ443544.2, dated 24 Oct. 2006; the West African genotype such as NI 64 IbH35 strain as another example having a sequence shown under NCBI Accession Number: HM045786.1, dated 28 Dec. 2010 and the Asian genotype such as RSU1 strain as another example having a sequence shown under NCBI Accession Number: HM045797.1, dated 28 Dec. 2010 and 99659 [2014 Carribean] strains for example having a sequence shown under NCBI Accession Number: KJ451624, dated 11 Sep. 2014. Other strains belonging to the different genotypes have been identified such as S27 strain as another example having a sequence shown under NCBI Accession Number:

AF369024.2, dated 14 Jan. 2014 and under UniProtKB/Swiss-Prot reference: Q8JUX5, dated 16 Sep. 2015 as well as SL15649 as another example having a sequence shown under NCBI Accession Number: GU189061, dated 14 Dec. 2011. Other examples of referenced CHIKV strains are available within the Virus Pathogen Database, with respect to their genomes at: viprbrc.org/brc/vipr_genome_search.spg?method=doQuickTextSearch&decorator=toga&pageTo=1&selectionContext=1476362322448, or with respect to associated proteins at: viprbrc.org/brc/vipr_protein_search.spg?method=doQuickTextSearch&decorator-toga&pageTo=1&selectionContext=1476362669763.

Similar to the genome of other alphaviruses, the CHIKV genome encodes two envelope glycoproteins, E2 and E1, which are derived from a larger polyprotein precursor (capsid/E3/E2/6K/E1; as shown under NCBI Accession Number: NC_004162.2, dated 27 Jun. 2012) and are embedded in the viral membrane. The mature virion is comprised of three major structural proteins: a nucleocapsid protein and two glycoproteins, E1 and E2, where E2 functions in attachment to cells and E1 participates in virus fusion. A third glycoprotein, E3, is associated with mature virions in some alphaviruses, but no others, while 6K protein, a membrane-associated peptide created by cleavage of the polyprotein precursor to release E2 and E1, is incorporated into particles at a low level. The organization of the alphavirus surface glycoproteins in particles has been defined using cryo-electron microscopy (Cryo-EM), while the atomic structure of CHIKV glycoprotein was recently solved by X-ray crystallography both for mature particles and for immature precursor polyprotein. 240 copies each of three glycoproteins (E3/E2/E1) come together to form 80 spikes on the mature virus that constitute an icosahedral protein shell surrounding the viral membrane. (Voss J E et al 2010, Nature 468:709-712). The folding, transport to the surface and function of these glycoproteins relies on their correct interactions with each other. E1 consists of three b-sheet domains, termed I, II and III; E2 contains three immunoglobulin-like domains (A, B and C, with A being at the N-terminus). In the complex, domain B lies at the membrane distal end and contacts E3, domain C is closest to the viral membrane and domain A is in the center (Fox J M et al 2015, Cell 163:1095-1107 and WO 2015010125). Sequences and informations for the CHIKV E1, E2 and E3 proteins are provided in PDB entries No. 2xFB and 2xFC (last updated: 24 Nov. 2010), PDB entries No. 3N40, 3N41, 3N42, 3N43 and 3N44 (last updated: 1 Dec. 2010), respectively, as non-limited examples.

Antibodies Featured in the Invention

For therapeutic purposes, it is desirable to generate mAbs that are better suited to the pharmaceutical properties required of them by improving, in particular, their binding to the antigen(s) they target, their stability, pharmacokinetics and pharmacodynamics as well as their functions.

As a first object, anti-CHIKV antibodies are based on fully-human parent antibodies, respectively mAb1 and mAb2, which have a high binding affinity (within the nanomolar range) toward different CHIKV strains and particularly to their respective protein E2. Hence, they display broad and ultrapotent neutralizing activities against various CHIKV strains.

MAb1 comprises:

a variable domain of heavy chain consisting of sequence: QVQLVQSGAEVKKPGASVKVSCKASGYSFTSY-GISWVRQAPGQGLEWMGWISTYK GYTQYAQNFQGRVTITTDTPAT-TVYMELRSLRSDDTAVYYCARVL-SETGYFYYYYY GMDVWGQGTLVTVSS (SEQ ID NO: 1) wherein CDRs are shown in bold character, respectively, CDRH1 (GYSFTSYG, SEQ ID NO: 5), CDRH2 (ISTYKGYT, SEQ ID NO: 6) and CDRH3 (ARVLSETGYFYYYYYGMDV, SEQ ID NO: 7). Framework regions encompass CDRH1, CDRH2 and CDRH3;

a variable domain of light chain consisting of sequence: QAVVTQPPSVSGAPGQRVTISCTGSSSNIGA-DYNVHWYQLLPGTAPKLLIYGNTNR PSGVPDRFSGSKSGTSASLAITGLQAEDEAD-YYCQSYDSSLSASVFGGGTKLTVL (SEQ ID NO: 2) wherein CDRs are shown in bold character, respectively, CDRL1 (SSNIGADYN, SEQ ID NO: 8), CDRL2 (GNT) and CDRL3 (QSYDSSLSASV, SEQ ID NO: 10). Framework regions encompass CDRL1, CDRL2 and CDRL3;

Mab2 comprises:

a variable domain of heavy chain consisting of sequence: QVQLVQSGAEVKKPGASVKVSCKVSGYILSK-LSVHWVRQAPGKGLEWMGGSERE DGETVYAQKFQGRISLTEDTSI-ETAYMELSSLSSEDTAVYYCATGGFWSMIGG-NGV DYWGQGTLVTVSS (SEQ ID NO: 3) wherein CDRs are shown in bold character, respectively, CDRH1 (GYILSKLS, SEQ ID NO: 11), CDRH2 (SEREDGET, SEQ ID NO: 12) and CDRH3 (ATGGFWSMIGGNGVDY, SEQ ID NO: 13). Framework regions encompass CDRH1, CDRH2 and CDRH3;

a variable domain of light chain consisting of sequence: QAVVTQSPSSLPASVGDRVTIT-CRASQDIRNNLGWYQQKPGKAPER-LIYGTSNLQS GVPSRFSGSGSGTEFTLTISSLQPEDFATYY-CLQHNSYPPTFGRGTKVEIK (SEQ ID NO: 4) wherein CDRs are shown in bold character, respectively, CDRL1 (QDIRNN, SEQ ID NO: 14), CDRL2 (GTS) and CDRL3 (LQHNSYPPT, SEQ ID NO: 16). Framework regions encompass CDRL1, CDRL2 and CDRL3.

In a first aspect, the present invention provides variant antibodies of mAb1 and mAb2 that bind to CHIKV and that have improved binding to FcRn receptor in an acidic environment because they comprise at least one amino acid substitution in their Fc domain. Such mutations result in an increase in serum half-life of such variant antibodies when administered to a patient. Non-limiting examples of such substitutions include modifications at position 250 (e.g. E or Q); 250 and 428 (e.g. L or F); 252 (e.g. L/Y/F/W or T), 254 (e.g. S or T) and 256 (e.g. S/R/Q/E/D or T); or a modification at position 428 and/or 433 (e.g. H/L/R/S/P/Q or K) and/or 434 (e.g. A, W, H, F or Y); or a modification at position 250 and/or 428; or a modification at position 307 or 308 (e.g. 308F, V308F) and 434, wherein said amino acid positions are given using the EU index Numbering (FIG. 1).

The inventors identified, as shown in FIG. 4 and example 2, that the binding to human and mouse FcRn receptors at pH 6 was increased when substitutions selected from the group below were introduced within mAb1 or mAb2 antibodies Fc region:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or v. a tyrosine at position 252, a threonine at position 254 and a glutamic acid at position 256.

Furthermore, the inventors showed, as described in example 3 and FIG. 5, that the binding of mAb1 and mAb2 to their CHIKV target pE2-E1 was not affected by the substitutions as mentioned above, when introduced into their Fc region and which increase the binding to human and mouse FcRn. As shown in example 2 and FIG. 4, substitutions of mAb1 or mAb2 Fc region show the strongest human and mouse FcRn binding when, either a tyrosine at position 252, a threonine at position 254 and a glutamic acid at position 256 respectively or a leucine at position 428 and a serine at position 434, respectively, are introduced in their respective Fc region.

As known in the art, Fc region is essential in determining the biological functions of the immunoglobulins, termed "effector functions". ADCC is one of the mechanisms, part of the cell-mediated immunity by which effector cells of the immune system (mainly Natural Killer cells) lyse a target cell that has been bound by specific antibodies. Therefore, ADCC is one of the mechanisms that can limit and contain infections. Cell-mediated activities involve the binding of the Fc domain to Fc-receptors such as FcγRI (CD64), FcγRII, FcγRIII of the effector cells.

As featured herein, wherein monoclonal antibodies are highly specific of CHIKV strains and are dedicated to treatment therapeutic purposes, their potential to activate ADCC is an important parameter to measure as ADCC seems to participate to the activity of anti-CHIKV antibodies in the control of the infection. As shown in example 4 and FIG. 6, the inventors have shown that the binding of mAb1 and mAb2 to FcγRIIIa was retained when substitutions selected from the group below were introduced into their respective Fc region:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively.

On the contrary, FcγRIIIa binding was reduced when mAb1 and mAb2 were substituted with a tyrosine at position 252, a threonine at position 254 and a glutamic acid at position 256 respectively.

Therefore, the inventors identified antibodies with improved binding to human FcRn receptor while retaining FcγRIIIa binding, making the antibodies of the present invention compatible with an increased half-life while maintaining their effector functions.

Hence, in a first aspect, the invention relates to an isolated monoclonal antibody that binds to CHIKV and that comprises three Heavy Chain Complementary Determining Regions (CDRHs) and three Light Chain Complementary Determining Regions (CDRLs), wherein:

i. said CDRHs have amino acid sequences of SEQ ID NO: 5, 6 and 7, and said CDRLs have amino acid sequences of SEQ ID NO: 8, GNT and 10, or
ii. said CDRHs have amino acid sequences of SEQ ID NO: 11, 12 and 13, and said CDRLs have amino acid sequences of SEQ ID NO: 14, GTS and 16, or
iii. said CDRHs and CDRLHs have amino acid sequences differing from the sequences of i. or ii. by one or two amino acid substitutions;

and wherein said antibody further comprises a Fc region comprising at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

Fc regions including such substitutions are shown on FIGS. 1 and 2 (SEQ ID NO: 17; SEQ ID NO: 59 to 63).

In one embodiment, an anti-CHIKV antibody comprises a Fc region comprising at least an alanine at position 434. In another embodiment, an anti-CHIKV antibody comprises a Fc region comprising an alanine at positions 307, 380 and 434. In another embodiment, an anti-CHIKV antibody comprises a Fc region comprising a glutamine at position 250 and a leucine at position 428. In another embodiment, an anti-CHIKV antibody comprises a Fc region comprising a leucine at position 428 and a serine at position 434. In another embodiment, an anti-CHIKV antibody comprises a Fc region comprising a tyrosine at position 252, a threonine at position 254 and a glutamic acid at position 256, The antibodies featured in the invention are derived from mAb1 or mAb2 and comprise three Heavy Chain Complementary Determining Regions (CDRHs) and three Light Chain Complementary Determining Regions (CDRLs), respectively, having:

i. amino acid sequences of SEQ ID NO: 5, 6 and 7, and amino acid sequences of SEQ ID NO: 8, GNT and 10, respectively, or
ii. amino acid sequences of SEQ ID NO: 11, 12 and 13, and amino acid sequences of SEQ ID NO: 14, GTS and 16, respectively, or
iii. amino acid sequences differing from sequences of i. or ii. by one or two amino acid substitutions;

In a further embodiment, the antibodies comprise CDRs with amino acid sequences differing by one or two amino acid substitutions from sequences of SEQ ID NO: 5, 6 and 7, and amino acid sequences of SEQ ID NO: 8, GNT and 10, respectively, or by one or two amino acid substitutions from sequences of SEQ ID NO: 11, 12 and 13, and of SEQ ID NO: 14, GTS and 16, respectively An amino acid substitution according to the invention may be a conservative or a non-conservative amino acid substitution. Examples of conservative substitutions are shown in the Table 1 below.

TABLE 1

| Conservative substitutions | Type of Amino Acid |
|---|---|
| Ala, Val, Leu, Ile, Met, Phe, Trp, Tyr | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

In another embodiment, the antibody comprises three Heavy Chain Complementary Determining Regions (CDRHs) having amino acid sequences of SEQ ID NO: 5, 6 and 7, respectively, or amino acid sequences differing from those sequences by one or two amino acid substitutions and wherein said antibody comprises three Light Chain Complementary Determining Regions (CDRLs) having amino acid sequences of SEQ ID NO: 8, GNT and 10, respectively, or amino acid sequences differing from those sequences by one or two amino acid substitutions and a Fc region comprising at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In another embodiment, the antibody is derived from mAb2 and comprises three Heavy Chain Complementary Determining Regions (CDRHs) having amino acid sequences of SEQ ID NO: 11, 12 and 13, respectively, or amino acid sequences differing from those sequences by one or two amino acid substitutions and wherein said antibody comprises three Light Chain Complementary Determining Regions (CDRLs) having amino acid sequences of SEQ ID NO: 14, GTS and 16, respectively, or amino acid sequences differing from those sequences by one or two amino acid substitutions and a Fc region comprising at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In another embodiment, the antibody comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In a further embodiment, the variant antibody (mAb3) comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least an alanine at position 434, wherein said amino acid position is given according to the EU index.

In another further embodiment, the variant antibody (mAb4) comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least an alanine at positions 307, 380 and 434, respectively, wherein said amino acid positions are given according to the EU index.

In another further embodiment, the variant antibody (mAb5) comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least a glutamine at position 250 and a leucine at position 428, respectively, wherein said amino acid positions are given according to the EU index.

In another further embodiment, the variant antibody (mAb7) comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least a leucine at position 428 and a serine at position 434, respectively, wherein said amino acid positions are given according to the EU index.

In another further embodiment, the variant antibody (mAb6) comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least a tyrosine at position 252, a threonine at position 254 and a glutamic acid at position 256, respectively, wherein said amino acid positions are given according to the EU index.

In another embodiment, the variant antibody comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In a further embodiment, the variant antibody comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least an alanine at position 434, wherein said amino acid position is given according to the EU index.

In another further embodiment, the variant antibody comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least an alanine at positions 307, 380 and 434, respectively, wherein said amino acid positions are given according to the EU index.

In another further embodiment, the variant antibody comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least a glutamine at position 250 and a leucine at position 428, respectively, wherein said amino acid positions are given according to the EU index.

In another further embodiment, the variant antibody (mAb8) comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least a leucine at position 428 and a serine at position 434, respectively, wherein said amino acid positions are given according to the EU index.

In another further embodiment, the variant antibody (mAb9) comprises three Heavy Chain Complementary Determining Regions (CDRHs) having amino acid sequences of SEQ ID NO: 11, 12 and 13, respectively, and three Light Chain Complementary Determining Regions (CDRLs) having amino acid sequences of SEQ ID NO: 14, GTS and 16, respectively, and a Fc region comprising at least a tyrosine at position 252, a threonine at position 254 and a glutamic acid at position 256, respectively, wherein said amino acid positions are given according to the EU index.

The inventors showed, as described in example 3 and FIG. 5, that the binding of mAb1 and mAb2 to their CHIKV target pE2-E1 was not affected when comprising a Fc region comprising at least one residue as mentioned above. The inventors also showed that these antibodies, comprising a Fc region comprising at least one residue as mentioned above, all display an increased binding to human and mouse FcRn (example 2 and FIG. 4) which have a positive impact on their respective half-life and consequently of benefit for anti-CHIKV therapy; the highest FcRn binding in human and in mouse being shown when, either a tyrosine at position 252, a threonine at position 254 and a glutamic acid at position 256 respectively or a leucine at position 428 and a serine at position 434, respectively, are introduced in their respective Fc region.

Therefore, in an exemplary embodiment, the variant antibody comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least a leucine at position 428 and a serine at position 434, respectively, or a Fc region comprising at least a tyrosine at position 252, a threonine at position 254 and a glutamic acid at position 256, respectively, wherein said amino acid positions are given according to the EU index.

Furthermore, as shown in example 4 and FIG. 6, the inventors have shown that the binding of mAb1 and mAb2 to FcγRIIIa was retained when substitutions selected from the group below were introduced into their respective Fc region:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively.

On the contrary, FcγRIIIa binding was reduced when mAb1 and mAb2 were substituted with a tyrosine at position 252, a threonine at position 254 and a glutamic acid at position 256 respectively.

Therefore, the inventors identified at least one antibody with unaffected binding to its target and improved binding to human FcRn receptor while retaining FcγRIIIa binding, making it compatible with a development of therapeutics to prevent and treat CHIKV disease with respect to its increased half-life while maintaining their effector functions.

In a typical embodiment, the variant antibody comprises three Heavy Chain Complementary Determining Regions (CDRHs) having amino acid sequences of SEQ ID NO: 5, 6 and 7, respectively, and three Light Chain Complementary Determining Regions (CDRLs) having amino acid sequences of SEQ ID NO: 8, GNT and 10, respectively, and a Fc region comprising at least a leucine at position 428 and a serine at position 434, respectively, wherein said amino acid positions are given according to the EU index.

In other words, the antibody featured herein can be described as an isolated monoclonal antibody that binds to CHIKV and that comprises three Heavy Chain Complementary Determining Regions (CDRHs) and three Light Chain Complementary Determining Regions (CDRLs), wherein:

i. said CDRHs have amino acid sequences of SEQ ID NO: 5, 6 and 7, and said CDRLs have amino acid sequences of SEQ ID NO: 8, GNT and 10, or
ii. said CDRHs have amino acid sequences of SEQ ID NO: 11, 12 and 13, and said CDRLs have amino acid sequences of SEQ ID NO: 14, GTS and 16, or
iii. said CDRHs and CDRLHs have amino acid sequences differing from the sequences of i. or ii. by one or two amino acid substitutions;

and wherein said antibody further comprises a Fc region comprising at least one residue selected from the group consisting of:

iv. an alanine at position 434, or
v. an alanine at positions 307, 380 and 434, or
vi. a glutamine at position 250 and a leucine at position 428, or
vii. a leucine at position 428 and a serine at position 434, or
viii. a tyrosine at position 252, a threonine at position 254 and a glutamic acid at position 256, wherein said amino acid positions are given according to the EU index;

and wherein the antibody has one or more of the following properties:

i. binds a CHIKV pE2-E1 target with a binding dissociation equilibrium constant ($K_0$) of less than about 10 nM;

ii. binds human FcRn with a $K_D$ of less than about 200 nM;

iii. binds human FcγRIII with a $K_D$ of less than about 600 nM;

In one embodiment the antibody according to the invention binds a CHIKV pE2-E1 target with a binding dissociation equilibrium constant ($K_D$) of less than about 5 nM, less than about 4 nM, 3, 2, 1 nM, less than about 0.9, 0.8, 0.7, 0.6, 0.5, 0.4, 0.3 nM or less than about 0.25 nM, 0.20 nM, 0.15 nM, 0.1 nM.

In another embodiment, the antibody according to the invention binds human FcRn with a $K_D$ of less than about 200 nM, less than about 100 nM, less than about 50 nM, 45, 40, 35, 30 nM or less than about 25 nM, 20, 15 or 10 NM.

In another embodiment, the antibody according to the invention binds human FcγRIII with a $K_D$ of less than about 600 nM, less than about 500 nM, 400 nM, 300 nM, less than about 200 nM, 150, 100 or 50 nM.

Binding to CHIKV pE2-E1 target, human FcRn and human FcγRIII can for instance be measured by a surface plasmon resonance assay, e.g. at 37° C. This assay can for instance be performed as described in Examples 1 to 4.

The "Fc region" according to the invention can belong to one of the four human subclasses IgG (IgG1, IgG2. IgG3 and IgG4) heavy chains that determine the functional activity of the antibodies. In one embodiment, the Fc region belongs to an IgG1 subtype heavy chain. In another embodiment, the Fc region belongs to an IgG2 subtype heavy chain. In another embodiment, the Fc region belongs to an IgG3 subtype heavy chain. In another embodiment, the Fc region belongs to an IgG4 subtype heavy chain. In another embodiment, the Fc region comprises or consists of a sequence of IgG1 FC region (SEQ ID NO: 17), except for the mutations described herein (FIGS. 1 and 2).

In one embodiment, the antibody has a Fc region that comprises or consists of a sequence having at least 80% identity with SEQ ID NO: 17. In another embodiment, the antibody has a Fc region that comprises or consists of a sequence having at least 85% identity with SEQ ID NO: 17. In another embodiment, the antibody has a Fc region that comprises or consists of a sequence having at least 90% identity with SEQ ID NO: 17. In a further embodiment, the antibody has a Fc region that comprises or consists of a sequence having 91, 92, 93, 94, 95, 96, 97, 98 or 99% identity with SEQ ID NO: 17.

In one embodiment, the antibody has a Fc region comprising one or several of the substitutions as described above and within examples. In another embodiment, the antibody has a Fc region that comprises or consists of a sequence having at least 80% identity with SEQ ID NO: 59, 60, 61, 62 and 63.

Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron, P. C. et al., 1992, J Exp Med. 176(4): 1191-1195 and Shopes B., 1992, J Immunol. 148(9): 2918-2922).

In another embodiment, the antibody comprises a variable region of its heavy chain that comprises or consists of a sequence having at least 80% identity with SEQ ID NO: 1. In another embodiment, the antibody comprises a variable region of its heavy chain that comprises or consists of a sequence having at least 85% identity with SEQ ID NO: 1. In another embodiment, the antibody comprises a variable region of its heavy chain that comprises or consists of a sequence having at least 90% identity with SEQ ID NO: 1. In another embodiment, the antibody comprises a variable region of its heavy chain that comprises or consists of a sequence having 91, 92, 93, 94, 95, 96, 97, 98 or 99% identity with SEQ ID NO: 1.

In another embodiment, the antibody comprises a variable region of its light chain that comprises or consists of a sequence having at least 80% identity with SEQ ID NO: 2. In another embodiment, the antibody comprises a variable region of its light chain that comprises or consists of a sequence having at least 85% identity with SEQ ID NO: 2. In another embodiment, the antibody comprises a variable region of its light chain that comprises or consists of a sequence having at least 90% identity with SEQ ID NO: 2. In another embodiment, the antibody comprises a variable region of its light chain that comprises or consists of a sequence having 91, 92, 93, 94, 95, 96, 97, 98 or 99% identity with SEQ ID NO: 2.

In another embodiment, the heavy chain of the antibody comprises or consists of a sequence having at least 80% identity with SEQ ID NO: 19. In another embodiment, the heavy chain of the antibody comprises or consists of a sequence having at least 85% identity with SEQ ID NO: 19. In another embodiment, the heavy chain of the antibody comprises or consists of a sequence having at least 90% identity with SEQ ID NO: 19. In another embodiment, the heavy chain of the antibody comprises or consists of a sequence having 91, 92, 93, 94, 95, 96, 97, 98 or 99% identity with SEQ ID NO: 19.

In another embodiment, the light chain of the antibody comprises or consists of a sequence having at least 80% identity with SEQ ID NO: 20. In another embodiment, the light chain of the antibody comprises or consists of a sequence having at least 85% identity with SEQ ID NO: 20. In another embodiment, the light chain of the antibody comprises or consists of a sequence having at least 90% identity with SEQ ID NO: 20. In another embodiment, the light chain of the antibody comprises or consists of a sequence having 91, 92, 93, 94, 95, 96, 97, 98 or 99% identity with SEQ ID NO: 20.

In another embodiment, the heavy chain of the antibody comprises or consists of a sequence having at least 80% identity with SEQ ID NO: 23. In another embodiment, the heavy chain of the antibody comprises or consists of a sequence having at least 85% identity with SEQ ID NO: 23. In another embodiment, the heavy chain of the antibody comprises or consists of a sequence having at least 90% identity with SEQ ID NO: 23. In another embodiment, the heavy chain of the antibody comprises or consists of a sequence having 91, 92, 93, 94, 95, 96, 97, 98 or 99% identity with SEQ ID NO: 23.

In another embodiment, the heavy chain of the antibody comprises or consists of a sequence having at least 80% identity with SEQ ID NO: 25. In another embodiment, the heavy chain of the antibody comprises or consists of a sequence having at least 85% identity with SEQ ID NO: 25. In another embodiment, the heavy chain of the antibody comprises or consists of a sequence having at least 90% identity with SEQ ID NO: 25. In another embodiment, the heavy chain of the antibody comprises or consists of a sequence having 91, 92, 93, 94, 95, 96, 97, 98 or 99% identity with SEQ ID NO: 25.

In another embodiment, the heavy chain of the antibody comprises or consists of a sequence having at least 80% identity with SEQ ID NO: 27. In another embodiment, the heavy chain of the antibody comprises or consists of a sequence having at least 85% identity with SEQ ID NO: 27.

In another embodiment, the heavy chain of the antibody comprises or consists of a sequence having at least 90% identity with SEQ ID NO: 27. In another embodiment, the heavy chain of the antibody comprises or consists of a sequence having 91, 92, 93, 94, 95, 96, 97, 98 or 99% identity with SEQ ID NO: 27.

In another embodiment, the heavy chain of the antibody comprises or consists of a sequence having at least 80% identity with SEQ ID NO: 29. In another embodiment, the heavy chain of the antibody comprises or consists of a sequence having at least 85% identity with SEQ ID NO: 29. In another embodiment, the heavy chain of the antibody comprises or consists of a sequence having at least 90% identity with SEQ ID NO: 29. In another embodiment, the heavy chain of the antibody comprises or consists of a sequence having 91, 92, 93, 94, 95, 96, 97, 98 or 99% identity with SEQ ID NO: 29.

In another embodiment, the heavy chain of the antibody comprises or consists of a sequence having at least 80% identity with SEQ ID NO: 31. In another embodiment, the heavy chain of the antibody comprises or consists of a sequence having at least 85% identity with SEQ ID NO: 31. In another embodiment, the heavy chain of the antibody comprises or consists of a sequence having at least 90% identity with SEQ ID NO: 31. In another embodiment, the heavy chain of the antibody comprises or consists of a sequence having 91, 92, 93, 94, 95, 96, 97, 98 or 99% identity with SEQ ID NO: 31.

In one embodiment, the antibody is a combination between an heavy chain and a light chain or between an heavy chain and a light chain encoded by a nucleotide sequence of the sequences as described in the table 2 below.

TABLE 2

| | Amino acid sequences | | Nucleotide sequences | |
|---|---|---|---|---|
| | HC | LC | HC | LC |
| mAb3 = mAb1A | SEQ ID NO: 23 | SEQ ID NO: 20 | SEQ ID NO: 24 | SEQ ID NO: 22 |
| mAb4 = mAb1AAA | SEQ ID NO: 25 | SEQ ID NO: 20 | SEQ ID NO: 26 | SEQ ID NO: 22 |
| mAb5 = mAb1QL | SEQ ID NO: 27 | SEQ ID NO: 20 | SEQ ID NO: 28 | SEQ ID NO: 22 |
| mAb6 = mAb1YTE | SEQ ID NO: 29 | SEQ ID NO: 20 | SEQ ID NO: 30 | SEQ ID NO: 22 |
| mAb7 = mAb1LS | SEQ ID NO: 31 | SEQ ID NO: 20 | SEQ ID NO: 32 | SEQ ID NO: 22 |

In another embodiment, the antibody comprises a variable region of its heavy chain that comprises or consists of a sequence having at least 80% identity with SEQ ID NO: 3. In another embodiment, the antibody comprises a variable region of its heavy chain that comprises or consists of a sequence having at least 85% identity with SEQ ID NO: 3. In another embodiment, the antibody comprises a variable region of its heavy chain that comprises or consists of a sequence having at least 90% identity with SEQ ID NO: 3. In another embodiment, the antibody comprises a variable region of its heavy chain that comprises or consists of a sequence having 91, 92, 93, 94, 95, 96, 97, 98 or 99% identity with SEQ ID NO: 3.

In another embodiment, the antibody comprises a variable region of its light chain that comprises or consists of a sequence having at least 80% identity with SEQ ID NO: 4. In another embodiment, the antibody comprises a variable region of its light chain that comprises or consists of a sequence having at least 85% identity with SEQ ID NO: 4. In another embodiment, the antibody comprises a variable region of its light chain that comprises or consists of a sequence having at least 90% identity with SEQ ID NO: 4. In another embodiment, the antibody comprises a variable region of its light chain that comprises or consists of a sequence having 91, 92, 93, 94, 95, 96, 97, 98 or 99% identity with SEQ ID NO: 4.

In another embodiment, the heavy chain of the antibody comprises or consists of a sequence having at least 80% identity with SEQ ID NO: 37. In another embodiment, the heavy chain of the antibody comprises or consists of a sequence having at least 85% identity with SEQ ID NO: 37. In another embodiment, the heavy chain of the antibody comprises or consists of a sequence having at least 90% identity with SEQ ID NO: 37. In another embodiment, the heavy chain of the antibody comprises or consists of a sequence having 91, 92, 93, 94, 95, 96, 97, 98 or 99% identity with SEQ ID NO: 37.

In another embodiment, the light chain of the antibody comprises or consists of a sequence having at least 80% identity with SEQ ID NO: 38. In another embodiment, the light chain of the antibody comprises or consists of a sequence having at least 85% identity with SEQ ID NO: 38. In another embodiment, the light chain of the antibody comprises or consists of a sequence having at least 90% identity with SEQ ID NO: 38. In another embodiment, the light chain of the antibody comprises or consists of a sequence having 91, 92, 93, 94, 95, 96, 97, 98 or 99% identity with SEQ ID NO: 38.

In another embodiment, the heavy chain of the antibody comprises or consists of a sequence having at least 80% identity with SEQ ID NO: 41. In another embodiment, the heavy chain of the antibody comprises or consists of a sequence having at least 85% identity with SEQ ID NO: 41. In another embodiment, the heavy chain of the antibody comprises or consists of a sequence having at least 90% identity with SEQ ID NO: 41. In another embodiment, the heavy chain of the antibody comprises or consists of a sequence having 91, 92, 93, 94, 95, 96, 97, 98 or 99% identity with SEQ ID NO: 41.

In another embodiment, the heavy chain of the antibody comprises or consists of a sequence having at least 80% identity with SEQ ID NO: 43. In another embodiment, the heavy chain of the antibody comprises or consists of a sequence having at least 85% identity with SEQ ID NO: 43. In another embodiment, the heavy chain of the antibody comprises or consists of a sequence having at least 90% identity with SEQ ID NO: 43. In another embodiment, the heavy chain of the antibody comprises or consists of a sequence having 91, 92, 93, 94, 95, 96, 97, 98 or 99% identity with SEQ ID NO: 43.

In one embodiment, the antibody is a combination between an heavy chain and a light chain or between an heavy chain and a light chain encoded by a nucleotide sequence of the sequences as described in the table 3 below.

TABLE 3

| | Amino acid sequences | | Nucleotide sequences | |
|---|---|---|---|---|
| | HC | LC | HC | LC |
| mAb8 = mAb2YTE | SEQ ID NO: 41 | SEQ ID NO: 38 | SEQ ID NO: 42 | SEQ ID NO: 40 |
| mAb9 = mAb2LS | SEQ ID NO: 43 | SEQ ID NO: 38 | SEQ ID NO: 44 | SEQ ID NO: 40 |

As already mentioned, for therapeutic purposes, it is highly desirable to generate mAbs that we can rely on in term of stability, pharmacokinetics and pharmacodynamics as well as their functions, while retaining their binding affinities to their specific target.

In a second aspect, the inventors identified hot spots that can be used to increase homogeneity and mitigate the chemistry, manufacture and control (CMC) liabilities. Such analysis focused on solvent exposed unwanted motif like oxidation, deamidation, isomerization, acidic cleavage, glycosylation as well as additional free Cysteine residues, identified, either in silico or experimentally, as potentially resulting in degradation products or heterogeneity of antibody preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an antibody or polypeptide described herein, it may therefore be desirable to remove the site, typically by conservative substitution to remove one of the implicated residues.

Figure 3:
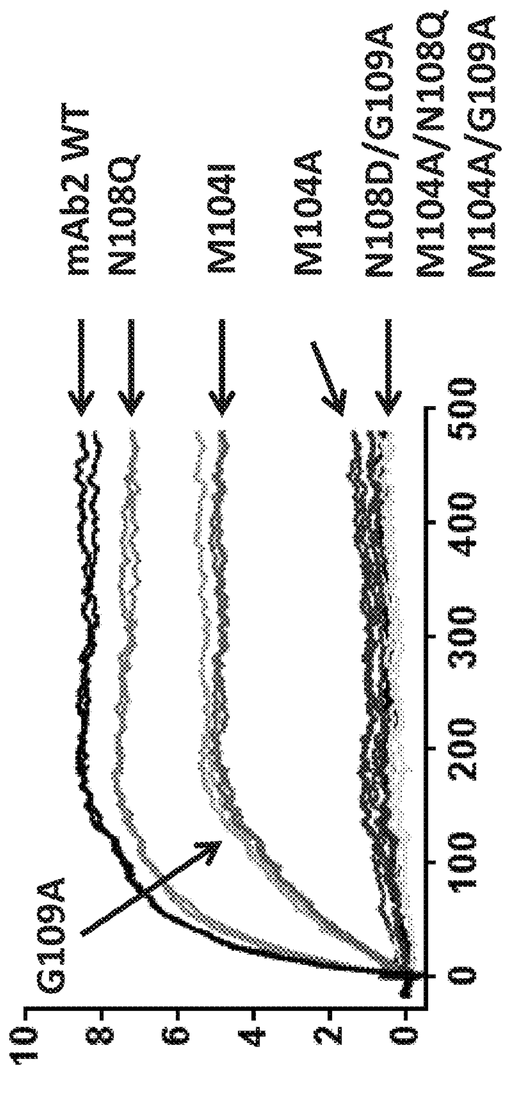
FIG. 3: Effect on E2-E1 target binding of mutations within CDRH3 of mAb2 created to eliminate potential deamination and oxydation motifs. Comparative results are shown in duplicate for each mutants.

As shown in example 1 and FIG. 3, the inventors identified at least three amino acids within CDRH3 of mAb2 (SEQ ID NO: 13) that can have deleterious consequences per se or because they create a non favourable motif based on the previous criteria when used for therapeutic purposes. As shown on FIG. 3, the inventors generate at least three variant antibodies of mAb2 with single substitutions respectively on positions 8, 12 and 13 of SEQ ID NO: 13 in order to suppress unwanted amino acids or motifs, which maintain binding affinity to their CHIKV pE2-E1 antigen. Hence, the inventors generated variants of mAb2 with, towards CMC criteria, higher stability, higher homogeneity when produced in bioreactors with less product-related impurities, while keeping their target affinity.

Hence, in a second aspect, the invention relates to mAb2 variant antibodies or an antigen-binding fragment thereof that binds to CHIKV and that comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and wherein said antibody or antigen-binding fragment thereof further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, and/or
ii. the amino acid at position 12 of SEQ ID NO: 33 is not N; and/or
iii. the amino acid at position 13 of SEQ ID NO: 33 is not G.

In one embodiment, the variant antibody comprises CDRHs with amino acid sequences differing by one or two amino acid substitutions from sequences of SEQ ID NO: 11, 12 and 33, and comprises CDRLs with amino acid sequences differing by one or two amino acid substitutions from sequences of SEQ ID NO: 14, GTS and 16, respectively. By "amino acid sequence differing by one or two amino acid substitutions", with respect to SEQ IDNO: 33, is meant additional amino acid substitutions compared to the substitutions envisioned at positions, 8, 12 and 13 of SEQ ID NO: 33 as featured in the invention.

An amino acid substitution may be a conservative or a non-conservative amino acid substitution. Examples of conservative substitutions are shown in the Table 1 above.

In another embodiment, the variant antibody comprises a CDRH3 of SEQ ID NO: 33 wherein the amino acid at position 8 of SEQ ID NO: 33 is not M, and the amino acid at position 12 of SEQ ID NO: 33 is not N; and the amino acid at position 13 of SEQ ID NO: 33 is not G. In another embodiment, said variant antibody comprises a CDRH3 of SEQ ID NO: 33 wherein the amino acid at position 8 of SEQ ID NO: 33 is M, and the amino acid at position 12 of SEQ ID NO: 33 is not N and the amino acid at position 13 of SEQ ID NO: 33 is not G. In other embodiments, said variant antibody comprises, respectively: a CDRH3 of SEQ ID NO: 33 wherein the amino acid at position 8 of SEQ ID NO: 33 is not M, and the amino acid at position 12 of SEQ ID NO: 33 is N and the amino acid at position 13 of SEQ ID NO: 33 is not G; a CDRH3 of SEQ ID NO: 33 wherein the amino acid at position 8 of SEQ ID NO: 33 is not M, and the amino acid at position 12 of SEQ ID NO: 33 is not N and the amino acid at position 13 of SEQ ID NO: 33 is G; a CDRH3 of SEQ ID NO: 33 wherein the amino acid at position 8 of SEQ ID NO: 33 is M, and the amino acid at position 12 of SEQ ID NO: 33 is N and the amino acid at position 13 of SEQ ID NO: 33 is not G; a CDRH3 of SEQ ID NO: 33 wherein the amino acid at position 8 of SEQ ID NO: 33 is M, and the amino acid at position 12 of SEQ ID NO: 33 is not N and the amino acid at position 13 of SEQ ID NO: 33 is G; a CDRH3 of SEQ ID NO: 33 wherein the amino acid at position 8 of SEQ ID NO: 33 is not M, and the amino acid at position 12 of SEQ ID NO: 33 is N and the amino acid at position 13 of SEQ ID NO: 33 is G; a CDRH3 of SEQ ID NO: 33 wherein the amino acid at position 8 of SEQ ID NO: 33 is not M, and the amino acid at position 12 of SEQ ID NO: 33 is N and the amino acid at position 13 of SEQ ID NO: 33 is not G. In other terms, SEQ ID NO: 33 cannot be identical to SEQ ID NO: 13.

By the expression "the amino acid at position X is not M", is meant that said amino acid at position X may be every amino acid but M. Similarly, by the expression "the amino acid at position X is not N", is meant that said amino acid at position X may be every amino acid but N. Similarly, by the expression "the amino acid at position X is not G", is meant that said amino acid at position X may be every amino acid but G. As a non-limiting example, the variant antibody wherein said variant comprises a CDRH3 of SEQ ID NO: 33 wherein the amino acid at position 8 of SEQ ID NO: 33 is not M, may comprise at said position 8 any amino acid selected from the group consisting of: A, G, V, L, I, F, W, Y, S, T, N, Q, C, D, E, K, R and H. As another non-limiting example, the variant antibody wherein said variant comprises a CDRH3 of SEQ ID NO: 33 wherein the amino acid at position 12 of SEQ ID NO: 33 is not N, may comprise at said position 12 any amino acid selected from the group consisting of: A, G, V, L, I, F, W, Y, S, T, M, Q, C, D, E, K, R and H. As another non-limiting example, the variant antibody wherein said variant comprises a CDRH3 of SEQ ID NO: 33 wherein the amino acid at position 13 of SEQ ID NO: 33 is not G, may comprise at said position 13 any amino acid selected from the group consisting of: A, N, V, L, I, F, W, Y, S, T, M, Q, C, D, E, K, R and H.

In another embodiment, the variant antibody or an antigen-binding fragment thereof, comprises:

A CDRH1 consisting of sequence SEQ ID NO: 11;
A CDRH2 consisting of sequence SEQ ID NO: 12;
A CDRH3 consisting of sequence SEQ ID NO: 33;
A CDRL1 consisting of sequence SEQ ID NO: 14;

A CDRL2 consisting of GTS;

A CDRL3 consisting of sequence SEQ ID NO: 16, and wherein:

i. the amino acid at position 8 of SEQ ID NO: 33 is not M, and/or ii. the amino acid at position 12 of SEQ ID NO: 33 is not N; and/or iii. the amino acid at position 13 of SEQ ID NO: 33 is not G.

In another embodiment, the variant antibody or an antigen-binding fragment thereof, comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, or ii. the amino acid at position 12 of SEQ ID NO: 33 is not N; or iii. the amino acid at position 13 of SEQ ID NO: 33 is not G.

In another embodiment, the variant antibody or an antigen-binding fragment thereof, comprises three Heavy Chain Complementary Determining Regions (CDRHs) having amino acid sequences of SEQ ID NO: 11, 12 and 33, respectively, and further comprises three Light Chain Complementary Determining Regions (CDRLs) having amino acid sequences of SEQ ID NO: 14, GTS and 16, respectively, and wherein:

i. the amino acid at position 8 of SEQ ID NO: 33 is not M, or ii. the amino acid at position 12 of SEQ ID NO: 33 is not N; or iii. the amino acid at position 13 of SEQ ID NO: 33 is not G.

In other words and as shown in example 1 and FIG. 3, the inventors identified antibodies or antigen-binding fragments thereof that comprise three Heavy Chain Complementary Determining Regions (CDRHs) having amino acid sequences of SEQ ID NO: 11, 12 and 33, respectively, or having amino acid sequences differing from those sequences by one or two amino acid substitutions, and that further comprise three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, or ii. the amino acid at position 12 of SEQ ID NO: 33 is not N; or iii. the amino acid at position 13 of SEQ ID NO: 33 is not G, and wherein the antibody has one or more of the following properties:

i. binds a CHIKV pE2-E1 target with a binding dissociation equilibrium constant ($K_D$) of less than about 10 nM;

ii. binds human FcRn with a $K_D$ of less than about 200 nM;

iii. binds human FcγRIII with a $K_D$ of less than about 600 nM;

In one embodiment the antibody binds a CHIKV pE2-E1 target with a binding dissociation equilibrium constant ($K_D$) of less than about 5 nM, less than about 4 nM, 3, 2, 1 nM, less than about 0.9, 0.8, 0.7, 0.6, 0.5, 0.4, 0.3 nM or less than about 0.25 nM, 0.20 nM, 0.15 nM, 0.1 nM.

In another embodiment, the antibody binds human FcRn with a $K_D$ of less than about 200 nM, less than about 100 nM, less than about 50 nM, 45, 40, 35, 30 nM or less than about 25 nM, 20, 15 or 10 NM.

In another embodiment, the antibody according to the invention binds human FcγRIII with a $K_D$ of less than about 600 nM, less than about 500 nM, 400 nM, 300 nM, less than about 200 nM, 150, 100 or 50 nM.

Binding to CHIKV pE2-E1 target, human FcRn and human FcγRIII can for instance be measured by a surface plasmon resonance assay, e.g. at 37° C. This assay can for instance be performed as described in Examples 1 to 4.

In another embodiment, the variant antibody or an antigen-binding fragment thereof, comprises CDRH3 having an amino acid sequence of SEQ ID NO: 33, wherein the amino acid at position 8 of SEQ ID NO: 33 is selected from the group consisting of I, L, V, Q and N.

In another embodiment, the variant antibody (mAb10) or an antigen-binding fragment thereof, comprises:

A CDRH1 consisting of sequence SEQ ID NO: 11;

A CDRH2 consisting of sequence SEQ ID NO: 12;

A CDRH3 consisting of sequence SEQ ID NO: 34;

A CDRL1 consisting of sequence SEQ ID NO: 14;

A CDRL2 consisting of GTS;

A CDRL3 consisting of sequence SEQ ID NO: 16.

In another embodiment, the variant antibody or an antigen-binding fragment thereof, comprises CDRH3 having an amino acid sequence of SEQ ID NO: 33, wherein the amino acid at position 12 of SEQ ID NO: 33 is selected from the group consisting of Q, E, S, T and D.

In another embodiment, the variant antibody (mAb11) or an antigen-binding fragment thereof, comprises:

A CDRH1 consisting of sequence SEQ ID NO: 11;

A CDRH2 consisting of sequence SEQ ID NO: 12;

A CDRH3 consisting of sequence SEQ ID NO: 35;

A CDRL1 consisting of sequence SEQ ID NO: 14;

A CDRL2 consisting of GTS;

A CDRL3 consisting of sequence SEQ ID NO: 16.

In another embodiment, the variant antibody or an antigen-binding fragment thereof, comprises CDRH3 having an amino acid sequence of SEQ ID NO: 33, wherein the amino acid at position 13 of SEQ ID NO: 33 is selected from the group consisting of A, S and T.

In another embodiment, the variant antibody (mAb12) or an antigen-binding fragment thereof, comprises:

A CDRH1 consisting of sequence SEQ ID NO: 11;

A CDRH2 consisting of sequence SEQ ID NO: 12;

A CDRH3 consisting of sequence SEQ ID NO: 36;

A CDRL1 consisting of sequence SEQ ID NO: 14;

A CDRL2 consisting of GTS;

A CDRL3 consisting of sequence SEQ ID NO: 16.

In another embodiment, the antibody comprises a variable region of its heavy chain that comprises or consists of a sequence having at least 80% identity with SEQ ID NO: 56. In another embodiment, the antibody comprises a variable region of its heavy chain that comprises or consists of a sequence having at least 85% identity with SEQ ID NO: 56. In another embodiment, the antibody comprises a variable region of its heavy chain that comprises or consists of a sequence having at least 90% identity with SEQ ID NO: 56. In another embodiment, the antibody comprises a variable region of its heavy chain that comprises or consists of a sequence having 91, 92, 93, 94, 95, 96, 97, 98 or 99% identity with SEQ ID NO: 56.

In another embodiment, the antibody comprises a variable region of its heavy chain that comprises or consists of a sequence having at least 80% identity with SEQ ID NO: 57. In another embodiment, the antibody comprises a variable region of its heavy chain that comprises or consists of a sequence having at least 85% identity with SEQ ID NO: 57. In another embodiment, the antibody comprises a variable region of its heavy chain that comprises or consists of a sequence having at least 90% identity with SEQ ID NO: 57. In another embodiment, the antibody comprises a variable region of its heavy chain that comprises or consists of a sequence having 91, 92, 93, 94, 95, 96, 97, 98 or 99% identity with SEQ ID NO: 57.

In another embodiment, the antibody comprises a variable region of its heavy chain that comprises or consists of a sequence having at least 80% identity with SEQ ID NO: 58. In another embodiment, the antibody comprises a variable region of its heavy chain that comprises or consists of a sequence having at least 85% identity with SEQ ID NO: 58. In another embodiment, the antibody comprises a variable region of its heavy chain that comprises or consists of a sequence having at least 90% identity with SEQ ID NO: 58. In another embodiment, the antibody comprises a variable region of its heavy chain that comprises or consists of a sequence having 91, 92, 93, 94, 95, 96, 97, 98 or 99% identity with SEQ ID NO: 58.

In another embodiment, the heavy chain of the antibody comprises or consists of a sequence having at least 80% identity with SEQ ID NO: 45. In another embodiment, the heavy chain of the antibody comprises or consists of a sequence having at least 85% identity with SEQ ID NO: 45. In another embodiment, the heavy chain of the antibody comprises or consists of a sequence having at least 90% identity with SEQ ID NO: 45. In another embodiment, the heavy chain of the antibody comprises or consists of a sequence having 91, 92, 93, 94, 95, 96, 97, 98 or 99% identity with SEQ ID NO: 45.

In another embodiment, the heavy chain of the antibody comprises or consists of a sequence having at least 80% identity with SEQ ID NO: 47. In another embodiment, the heavy chain of the antibody comprises or consists of a sequence having at least 85% identity with SEQ ID NO: 47. In another embodiment, the heavy chain of the antibody comprises or consists of a sequence having at least 90% identity with SEQ ID NO: 47. In another embodiment, the heavy chain of the antibody comprises or consists of a sequence having 91, 92, 93, 94, 95, 96, 97, 98 or 99% identity with SEQ ID NO: 47.

In another embodiment, the heavy chain of the antibody comprises or consists of a sequence having at least 80% identity with SEQ ID NO: 49 or comprises or consists of a sequence encoded by a nucleotide sequence having at least 80% identity with SEQ ID NO: 50. In another embodiment, the heavy chain of the antibody comprises or consists of a sequence having at least 85% identity with SEQ ID NO: 49. In another embodiment, the heavy chain of the antibody comprises or consists of a sequence having at least 90% identity with SEQ ID NO: 49. In another embodiment, the heavy chain of the antibody comprises or consists of a sequence having 91, 92, 93, 94, 95, 96, 97, 98 or 99% identity with SEQ ID NO: 49.

In one embodiment, the antibody is a combination between an heavy chain and a light chain or between an heavy chain and a light chain encoded by a nucleotide sequence of the sequences as described in the table 4 below.

TABLE 4

| | Amino acid sequences | | Nucleotide sequences | |
|---|---|---|---|---|
| | HC | LC | HC | LC |
| mAb10 = mAb2M104I | SEQ ID NO: 45 | SEQ ID NO: 38 | SEQ ID NO: 46 | SEQ ID NO: 40 |
| mAb11 = mAb2N108Q | SEQ ID NO: 47 | SEQ ID NO: 38 | SEQ ID NO: 48 | SEQ ID NO: 40 |
| mAb12 = mAb2G109A | SEQ ID NO: 49 | SEQ ID NO: 38 | SEQ ID NO: 50 | SEQ ID NO: 40 |

In a third aspect, the inventors combined the beneficial aspects above. The inventors generated variants of mAb2 which, on one side, were substituted within CDRH3 to suppress non favourable amino acids or motifs based on chemistry, manufacture and control (CMC) liabilities criteria and on the other side, had improved binding to FcRn receptor in an acidic environment while retaining FcγRIIIa binding associated with effector functions because they comprised at least one amino acid substitution in their Fc domain.

Figure 4A:
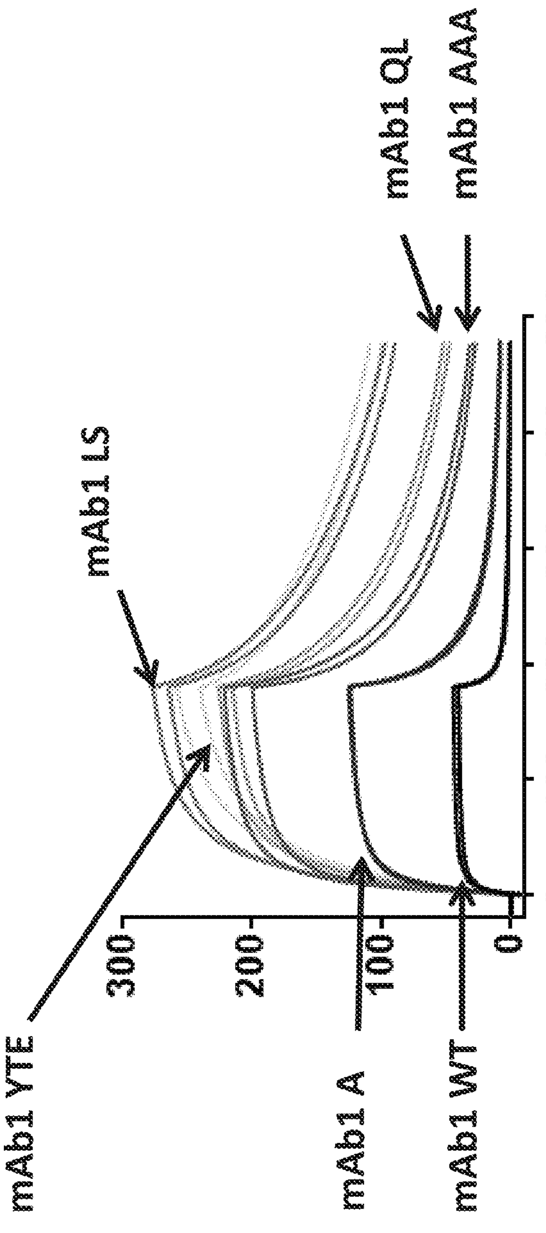
FIG. 4A-D: Effect on FcRn binding of substitutions in Fc regions of mAb1 and mAb2 respectively. Comparative results are shown in duplicate on human FcRn for mAb1 (FIG. 4A) and mAb2 (FIG. 4C) and on mouse FcRn for mAb1 (FIG. 4B) and mAb2 (FIG. 4D), at pH 6.0.
Figure 4B:
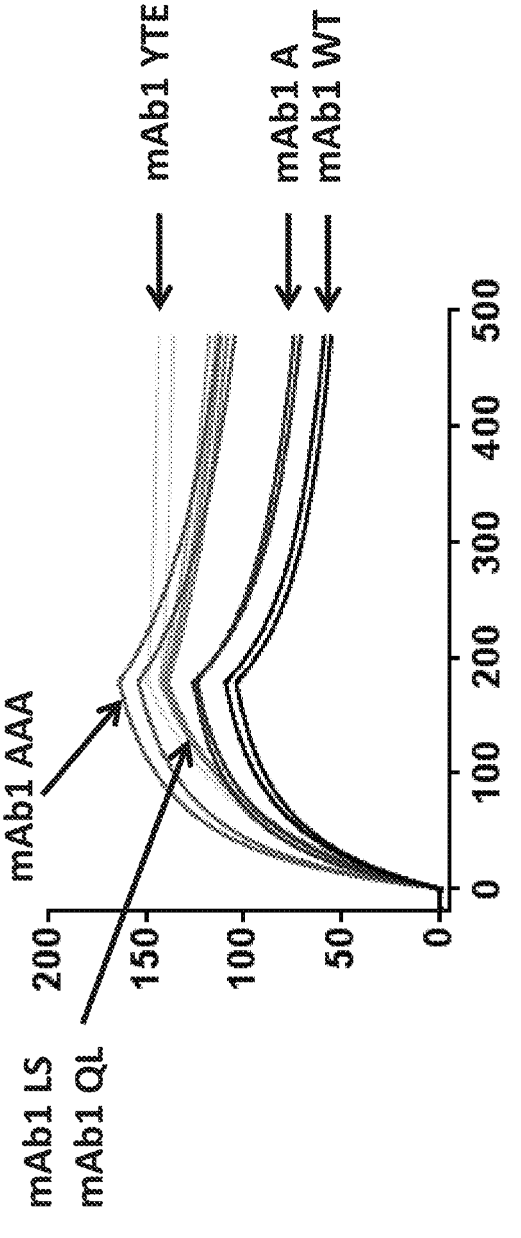
Figure 4C:
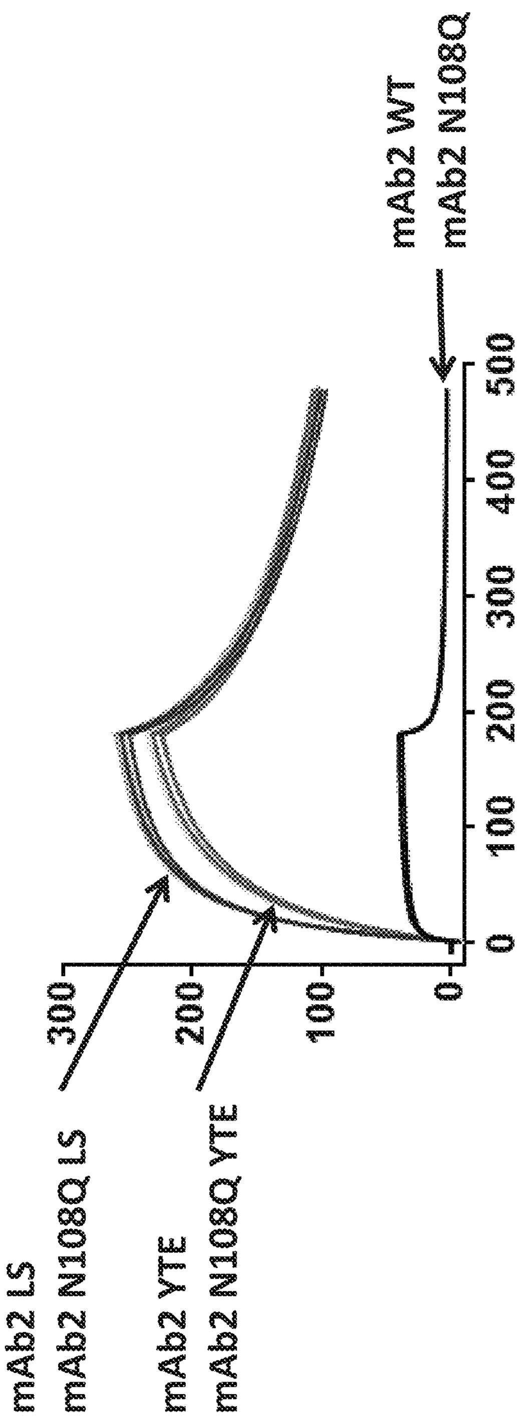
Figure 4D:
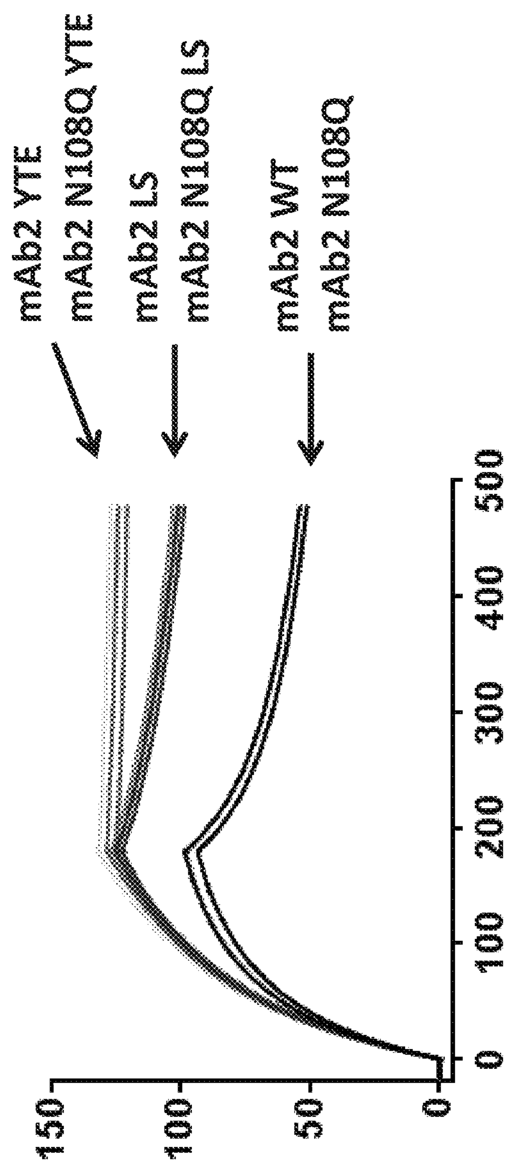

As described in example 2 and FIGS. 4C and 4D, the inventors showed that a variant of mAb2 wherein substitutions within its CDRH3 were introduced displayed an increased binding to human and mouse FcRn receptors at pH 6 when substitutions selected from the group below were introduced within its Fc region:

i. a leucine at position 428 and a serine at position 434, respectively, or
ii. a tyrosine at position 252, a threonine at position 254 and a glutamic acid at position 256.

Furthermore, the inventors confirmed, as described in example 3 and FIG. 5, that the binding to their CHIKV target pE2-E1 were not affected for antibodies cumulating substitutions within their CDRH3 and their Fc region as described above.

Figure 6A:
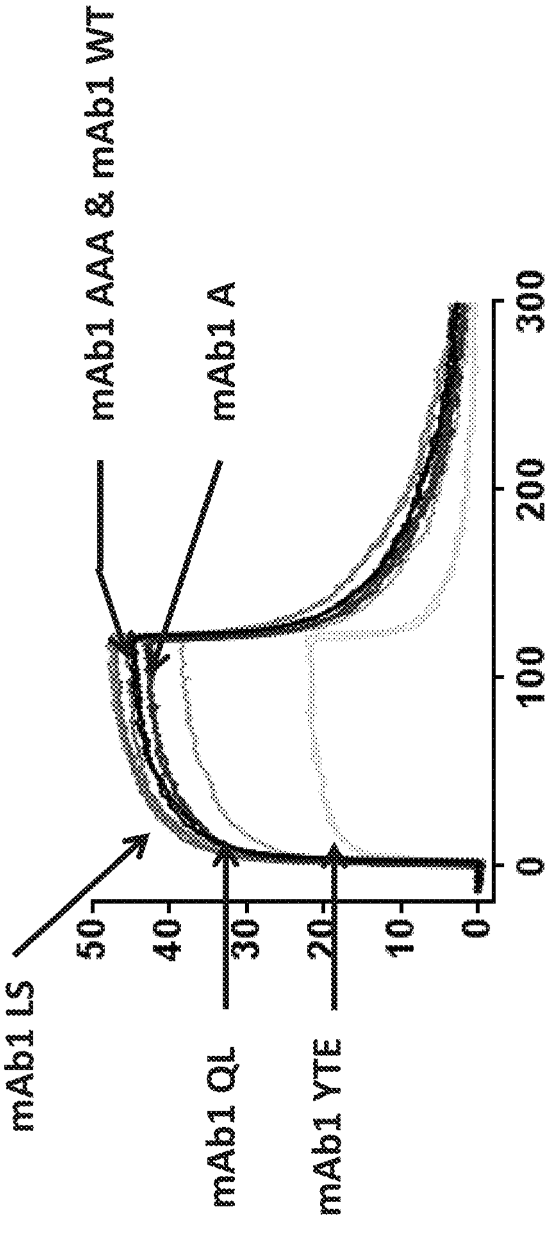
FIG. 6A-D: Effect on FcγRIIIa binding of substitutions in Fc regions of mAb1 and mAb2 respectively. Binding results are shown in duplicate on human FcγRIIIa high affinity receptor (FcγRIIIaV158) for mAb1 (FIG. 6A) and for mAb2 (FIG. 6B) as well as on human FcγRIIIa low affinity receptor (FcγRIIIaF158), respectively (FIG. 6C for mAb1 and FIG. 6D for mAb2).
Figure 6B:
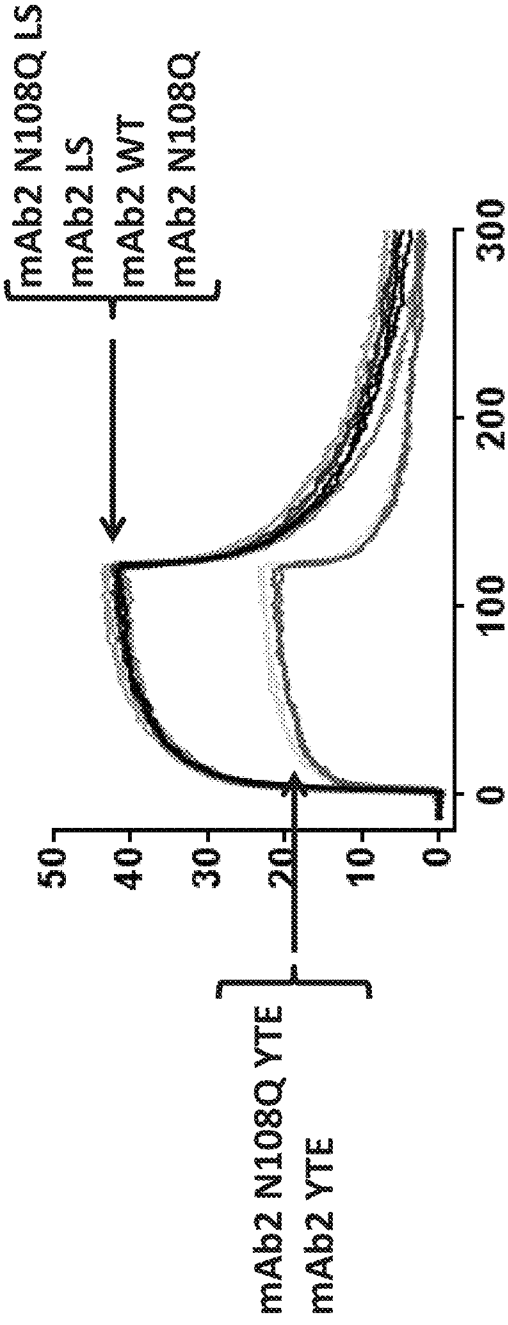
Figure 6C:
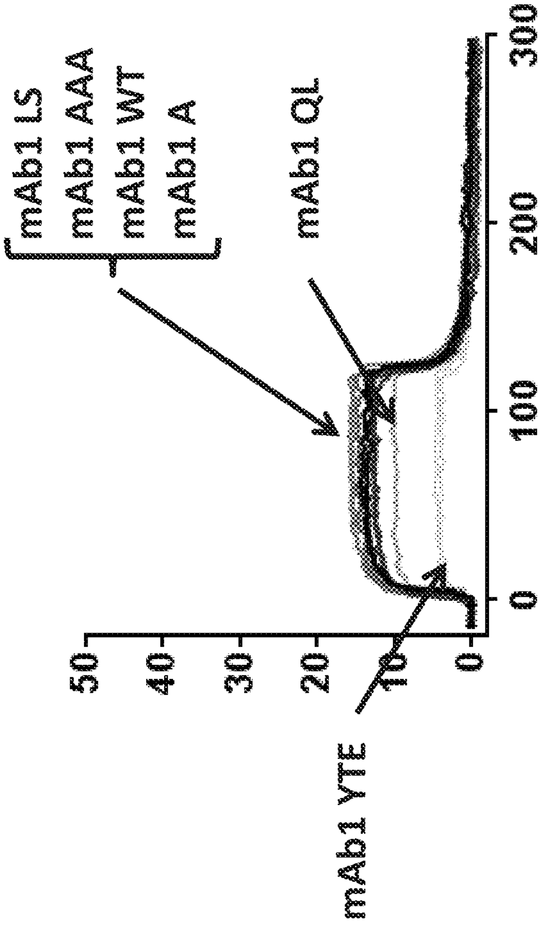
Figure 6D:
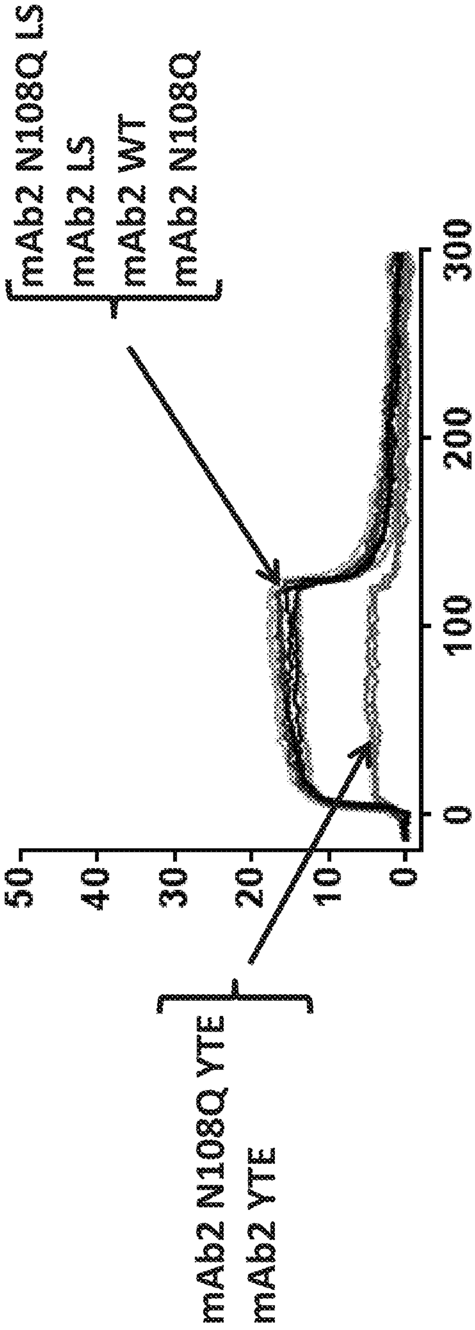

As shown in example 4 and FIGS. 6B and 6D, the inventors also confirmed that for such antibodies the binding to FcγRIIIa was retained at least when a leucine at position 428 and a serine at position 434, respectively, were introduced in their Fc region. On the contrary, FcγRIIIa binding was reduced when such antibodies were substituted with a tyrosine at position 252, a threonine at position 254 and a glutamic acid at position 256 respectively.

Therefore, the inventors confirmed on antibodies according to the invention which have been substituted within CDRH3 to suppress non favourable amino acids or motifs based on chemistry, manufacture and control (CMC) liabilities criteria, the beneficial effects of substitutions introduced within their respective Fc regions.

Hence, in this third aspect, the invention relates to mAb2 variant antibodies or an antigen-binding fragment thereof that binds to CHIKV and that comprises three Heavy Chain Complementary Determining Regions (CDRHs) having amino acid sequences of SEQ ID NO: 11, 12 and 33, respectively, or having amino acid sequences differing from those sequences by one or two amino acid substitutions, and wherein said antibody or antigen-binding fragment thereof further comprises three Light Chain Complementary Determining Regions (CDRLs) having amino acid sequences of SEQ ID NO: 14, GTS and 16, respectively, or having amino acid sequences differing from those sequences by one or two amino acid substitutions, and wherein:

i. the amino acid at position 8 of SEQ ID NO: 33 is not M, and/or
ii. the amino acid at position 12 of SEQ ID NO: 33 is not N; and/or
iii. the amino acid at position 13 of SEQ ID NO: 33 is not G;

and wherein said antibody comprises a Fc region comprising at least mutations selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In a third aspect, it is understood that any antibody of the second aspect, i.e. comprising a CDRH of SEQ ID NO:33, can comprise any mutation in the Fc region described in the first aspect, said antibody comprising a Fc region with at least one residue selected from the group consisting of:

i. an alanine at position 434, or
ii. an alanine at positions 307, 380 and 434, respectively, or
iii. a glutamine at position 250 and a leucine at position 428, respectively, or
iv. a leucine at position 428 and a serine at position 434, respectively, or
v. a tyrosine at position 252, a threonine at position 254 and a glutamic acid at position 256, respectively, wherein said amino acid positions are given according to the EU index.

In another embodiment, the variant antibody (mAb13) or an antigen-binding fragment thereof, comprises:

A CDRH1 consisting of sequence SEQ ID NO: 11;
A CDRH2 consisting of sequence SEQ ID NO: 12;
A CDRH3 consisting of sequence SEQ ID NO: 35;
A CDRL1 consisting of sequence SEQ ID NO: 14;
A CDRL2 consisting of GTS;
A CDRL3 consisting of sequence SEQ ID NO: 16;

and a Fc region comprising at least a tyrosine at position 252, a threonine at position 254 and a glutamic acid at position 256, respectively, wherein said amino acid positions are given according to the EU index.

In another embodiment, the variant antibody (mAb14) or an antigen-binding fragment thereof, comprises:

A CDRH1 consisting of sequence SEQ ID NO: 11;
A CDRH2 consisting of sequence SEQ ID NO: 12;
A CDRH3 consisting of sequence SEQ ID NO: 35;
A CDRL1 consisting of sequence SEQ ID NO: 14;
A CDRL2 consisting of GTS;
A CDRL3 consisting of sequence SEQ ID NO: 16.

and a Fc region comprising at least a leucine at position 428 and a serine at position 434, respectively, wherein said amino acid positions are given according to the EU index.

In another embodiment, the heavy chain of the antibody comprises or consists of a sequence having at least 80% identity with SEQ ID NO: 51. In another embodiment, the heavy chain of the antibody comprises or consists of a sequence having at least 85% identity with SEQ ID NO: 51. In another embodiment, the heavy chain of the antibody comprises or consists of a sequence having at least 90% identity with SEQ ID NO: 51. In another embodiment, the heavy chain of the antibody comprises or consists of a sequence having 91, 92, 93, 94, 95, 96, 97, 98 or 99% identity with SEQ ID NO: 51.

In another embodiment, the heavy chain of the antibody comprises or consists of a sequence having at least 80% identity with SEQ ID NO: 53. In another embodiment, the heavy chain of the antibody comprises or consists of a sequence having at least 85% identity with SEQ ID NO: 53. In another embodiment, the heavy chain of the antibody comprises or consists of a sequence having at least 90% identity with SEQ ID NO: 53. In another embodiment, the heavy chain of the antibody comprises or consists of a sequence having 91, 92, 93, 94, 95, 96, 97, 98 or 99% identity with SEQ ID NO: 53.

In one embodiment, the antibody according to this particular aspect is a combination between an heavy chain and a light chain or between an heavy chain and a light chain encoded by a nucleotide sequence of the sequences as described in the table 5 below

TABLE 5

| | Amino acid sequences | | Nucleotide sequences | |
|---|---|---|---|---|
| | HC | LC | HC | LC |
| mAb13 = mAb2N108QYTE | SEQ ID NO: 51 | SEQ ID NO: 38 | SEQ ID NO: 52 | SEQ ID NO: 40 |
| mAb14 = mAb2N108QLS | SEQ ID NO: 53 | SEQ ID NO: 38 | SEQ ID NO: 54 | SEQ ID NO: 40 |

Nucleic Acids, Vectors and Recombinant Host Cells

A further object featured in the invention relates to a nucleic acid sequence comprising or consisting of a sequence encoding an antibody as defined herein, or a polypeptide, a heavy chain, a light chain or a fragment comprising or consisting of an antibody described herein or a fragment thereof.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object featured in the invention relates to a vector comprising a nucleic acid as described herein.

Such vectors may comprise regulatory elements, such as a promoter, enhancer, terminator and the like, to cause or direct expression of said polypeptide upon administration to a subject. Examples of promoters and enhancers used in the expression vector for animal cell include enhancer and promoter of human cytomegalovirus (Nelson, J., 1996 J. Virology 70: 3207-3986), early promoter and enhancer of SV40 (Mizukami, T. and Itoh, S. et al., 1987, J Biochem. 101(5): 1307-1310), LTR promoter and enhancer of Moloney mouse leukemia virus (Kuwana Y. et al., 1987, Biochem Biophys Res Commun. 149: 960-968), promoter (Mason, J. O. et al., 1985, Cell 41: 479-487) and enhancer (Gillies, S. D. et al., 1983, Cell 33: 717-728) of immunoglobulin H chain and the like.

Any expression vector for animal cell can be used, so long as a gene encoding the human antibody C region can be inserted and expressed. Examples of suitable vectors include pAGE107 (Miyaji, H. et al., 1990, Cytotechnology 3(2): 133-140), pAGE103 (Mizukami, T. and Itoh, S. et al., 1987, J Biochem. 101(5): 1307-1310), pHSG274 (Brady, G. et al., 1984, Gene 27(2): 223-232), pKCR (O'Hare, K. et al., 1981, Proc Natl Acad Sci USA. 78(3): 1527-1531), pSG1 beta d2-4- (Miyaji, H. et al., 1990, Cytotechnology 4: 173-180) and the like.

Other examples of plasmids include replicating plasmids comprising an origin of replication pCEP5, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

In one embodiment, the invention relates to a polynucleotide having at least 80% identity with one of the sequences selected from the group consisting of SEQ ID NO: 18, 21, 22, 24, 26, 28, 30, 32, 39, 40, 42, 44, 46, 48, 50, 52 and 54. In another embodiment, the invention relates to a polynucleotide having at least 85% identity with one of the sequences selected from the group consisting of SEQ ID NO: 18, 21, 22, 24, 26, 28, 30, 32, 39, 40, 42, 44, 46, 48, 50, 52 and 54. In another embodiment, the invention relates to a polynucleotide having at least 90% identity with one of the sequences selected from the group consisting of SEQ ID NO: 18, 21, 22, 24, 26, 28, 30, 32, 39, 40, 42, 44, 46, 48, 50, 52 and 54. In another embodiment, the invention relates to a polynucleotide having at least 91, 92, 93, 94, 95, 96, 97, 98 or 99% identity with one of the sequences selected from the group consisting of SEQ ID NO: 18, 21, 22, 24, 26, 28, 30, 32, 39, 40, 42, 44, 46, 48, 50, 52 and 54. In another embodiment, the invention relates to a polynucleotide encoding one of the heavy chains, or one of the light chains, or both heavy chains and light chains of the antibodies as described herein, i.e. mAb3, 4, 5, 6, 7, 8, 9, 10, 11, 12, 13 or 14. In another embodiment, the invention relates to a polynucleotide comprising a sequence encoding an antibody or an antigen-binding fragment thereof as featured herein.

A further object featured in the present invention relates to a cell which has been transfected, infected or transformed by a nucleic acid and/or a vector as described herein.

Accordingly, the present invention relates to a cell line producing one of the antibodies as described herein.

The term "transformation" means the introduction of a "foreign" (i.e. extrinsic) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids featured herein may be used to produce a recombinant anti-CHIKV antibody from a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, Kluyveromyces or Saccharomyces yeasts, mammalian cell lines (e.g., Vero cells, CHO cells, 3T3 cells, COS cells, HEK293 cells etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub, G. et al.; 1980, Proc Natl Acad Sci USA. 77(7): 4216-4220), rat YB2/3HL.P2.G11.16Ag.20 cell (ATCC CRL1662, hereinafter referred to as "YB2/0 cell"), and the like. The YB2/0 cell is of interest, since ADCC activity of chimeric or humanised antibodies is enhanced when expressed in this cell.

In particular, for expression of humanised antibody, the expression vector may be either of a type in which a gene encoding an antibody heavy chain and a gene encoding an antibody light chain exists on separate vectors or of a type in which both genes exist on the same vector (tandem type). In respect of easiness of construction of a humanised antibody expression vector, easiness of introduction into animal cells, and balance between the expression levels of antibody H and L chains in animal cells, humanised antibody expression vectors of the tandem type are commonly used (shitara, K. et al., 1994, J Immunol Methods. January 3: 167(1-2): 271-8). Examples of tandem type humanised antibody expression vectors include pKANTEX93 (WO 97/10354), pEE18 and the like.

The present invention also relates to a method of producing a recombinant host cell expressing an antibody according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody.

Such recombinant host cells can be used for the production of anti-CHIKV antibodies described herein.

Accordingly, the present invention relates to a method of producing a monoclonal antibody according to the invention, wherein said method comprises the steps of (i) culturing a cell line as described above; (ii) purifying the produced monoclonal antibody; and optionally (iii) formulating said monoclonal antibody into a pharmaceutical composition.

Methods of Producing Anti-CHIKV Antibodies

Anti-CHIKV antibodies featured in the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies or immunoglobulin chains, by standard techniques for production of polypeptides. For instance, they can be synthesized using well-known solid phase method, in particular using a commercially available peptide synthesis apparatus (such as that made by Applied Biosystems, Foster City, California) and following the manufacturer's instructions. Alternatively, antibodies and immunoglobulin chains can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In particular, the invention further relates to a method of producing an antibody which method comprises the steps consisting of: (i) culturing a transformed host cell according to the invention; (ii) expressing said antibody or polypeptide; and (iii) recovering the expressed antibody or polypeptide.

In other words, the invention relates to a method for producing an antibody, comprising the steps of:

(i) Providing a cell expressing the anti-CHIKV antibody;
(ii) Cultivating said cell;
(iii) Purifying said antibody; and
(iv) Optionally, formulating said antibody into a pharmaceutical composition.

Methods for producing humanised or chimeric antibodies involve conventional recombinant DNA and gene transfection techniques are well known in the art (See Morrison, S. L. and Oi, V. T., 1984, Annu Rev Immunol 2: 239-256 and patent documents U.S. Pat. Nos. 5,202,238; 5,204,244).

In a particular embodiment, a chimeric antibody of the present invention can be produced by obtaining nucleic sequences encoding the murine VL and VH domains as previously described, constructing a chimeric antibody expression vector by inserting them into an expression vector for animal cell having genes encoding human antibody CH and human antibody CL, and expressing the coding sequence by introducing the expression vector into an animal cell.

Antibodies featured herein are suitably separated from the culture medium by conventional immunoglobulin purification procedures such as, for example protein A affinity chromatography, ceramic hydroxyapatite chromatography, mixed-mode chromatography, size-exclusion chromatography etc.

The Fab can be obtained by treating an antibody which specifically reacts with CHIKV with a protease, such as papaine. Also, the Fab can be produced by inserting DNA sequences encoding both chains of the Fab of the antibody into a vector for prokaryotic expression, or for eukaryotic expression, and introducing the vector into procaryotic or eukaryotic cells (as appropriate) to express the Fab.

The F(ab')2 can be obtained treating an antibody which specifically reacts with CHIKV with a protease, pepsin. Also, the F(ab')2 can be produced by binding Fab' described below via a thioether bond or a disulfide bond.

The Fab' can be obtained treating F(ab')2 which specifically reacts with CHIKV with a reducing agent, such as dithiothreitol. Also, the Fab' can be produced by inserting DNA sequences encoding Fab' chains of the antibody into a vector for prokaryotic expression, or a vector for eukaryotic expression, and introducing the vector into prokaryotic or eukaryotic cells (as appropriate) to perform its expression.

The scFv can be produced by taking sequences of the CDRs or VH and VL domains as previously described, constructing a DNA encoding an scFv fragment, inserting the DNA into a prokaryotic or eukaryotic expression vector, and then introducing the expression vector into prokaryotic or eukaryotic cells (as appropriate) to express the scFv. To generate a humanised scFv fragment, a well known technology called CDR grafting may be used, which involves selecting the complementary determining regions (CDRs) according to the invention, and grafting them onto a human scFv fragment framework of known three dimensional structure (see, e. g., WO98/45322; WO 87/02671; U.S. Pat. Nos. 5,859,205; 5,585,089; 4,816,567; EP0173494).

The single chain antibody or VHH directed against CHIKV may be obtained for instance by a method comprising the steps of (a) immunizing a mammal belonging to the Camelidae with CHIKV or a fragment thereof, so as to elicit antibodies (and in particular heavy chain antibodies) against CHIKV; (b) obtaining a biological sample from the Camelidae thus immunized, said sample comprising heavy chain antibody sequences and/or VHH sequences that are directed against CHIKV; and (c) recovering (e.g isolating) heavy chain antibody sequences and/or VHH sequences that are directed against CHIKV from said biological sample. Suitable single chain antibody or VHH may also be obtained by screening a library comprising heavy chain antibody sequences and/or VHH sequences for heavy chain antibody sequences and/or VHH sequences that compete for binding with pE2-E1 of CHIKV as a non-limiting example.

Modification of the Anti-CHIKV Antibodies of the Invention

A further object of the present invention encompasses function-conservative variants of the antibodies described herein.

For example, certain amino acids may be substituted by other amino acids in a protein structure without appreciable loss of activity. Since the interactive capacity and nature of a protein define its biological functional activity, certain amino acid substitutions can be made in a protein sequence, and of course in its DNA encoding sequence, while nevertheless obtaining a protein with like properties. It is thus contemplated that various changes may be made to the antibodies sequences o, or corresponding DNA sequences which encode said antibodies, without appreciable loss of their binding activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

Another type of amino acid modification of an antibody may be useful for altering the original glycosylation pattern of the antibody, i.e. by deleting one or more carbohydrate moieties found in the antibody, and/or adding one or more glycosylation sites that are not present in the antibody. The presence of either of the tripeptide sequences asparagine-X-serine, and asparagine-X-threonine, where X is any amino acid except proline, creates a potential glycosylation site. Addition or deletion of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N-or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, or tyrosine, (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr, H. et al. (1987, Arch Biochem Biophys. 259(1): 52-57) and by Edge, A. S. et al. (1981, Anal Biochem. 118(1): 131-137). Enzymatic cleavage of carbohydrate moieties on antibodies can be achieved by the use of a variety of endo-and exo-glycosidases as described by Thotakura, NR. et al. (1987, Methods Enzymol 138: 350-359).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Pharmaceutical Compositions

The anti-CHIKV antibodies featured in the invention may be combined with pharmaceutically acceptable excipients, and optionally sustained-release matrices, such as biodegradable polymers, to form therapeutic compositions.

Thus, the invention also relates to a pharmaceutical composition comprising an anti-CHIKV antibody of the invention and a pharmaceutically acceptable carrier.

The invention also relates to an antibody according to the invention, for use as a medicament.

“Pharmaceutically” or “pharmaceutically acceptable” refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and gender of the patient, etc.

The pharmaceutical compositions can be formulated for a topical, oral, parenteral, intranasal, intravenous, intramuscular, subcutaneous or intraocular administration and the like.

In particular, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

In one embodiment, the invention relates to a pharmaceutical composition comprising antibodies or an antigen-binding fragment thereof that bind to CHIKV as described herein in a prophylactically or therapeutically effective amount, and a pharmaceutically acceptable carrier.

The pharmaceutical forms suitable for injectable use include sterile aqueous solutions or dispersions; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (for example, glycerol, propylene glycol, and liquid polyethylene glycol, and the like), suitable mixtures thereof. The proper fluidity can be maintained, for example, by the use of a coating, such as lecithin, by the maintenance of the required particle size in the case of dispersion and by the use of surfactants, stabilizing agents, cryoprotectants or antioxidants. The prevention of the action of microorganisms can be brought about by antibacterial and antifungal agents. In many cases, it will be preferable to include isotonic agents, for example, sugars or sodium chloride.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, common methods of preparation include vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, “Remington's Pharmaceutical Sciences” 15th Edition, pages 1035-1038 and 1570-1580). Some variation in dosage will necessarily occur depending on the condition of the subject being treated. The person responsible for administration will, in any event, determine the appropriate dose for the individual subject.

The antibody may be formulated within a therapeutic mixture to comprise about 0.01 to 100 milligrams, per dose or so.

According to certain embodiments, a single or multiple doses of an anti-CHIKV antibody described herein may be administered to a subject over a defined time course.

The methods according to this aspect comprise sequentially administering to a subject multiple doses of an antibody to CHIKV. As used herein, "sequentially administering" means that each dose of antibody to CHIKV is administered to the subject at a different point in time, e.g., on different days separated by a predetermined interval (e.g., hours, days, weeks or months). The present invention includes methods which comprise sequentially administering to the patient a single initial dose of an antibody to CHIKV, followed by one or more secondary doses of the antibody to CHIKV and optionally followed by one or more tertiary doses of the antibody to CHIKV.

The terms "initial dose," "secondary doses," and "tertiary doses," refer to the temporal sequence of administration of the antibody to CHIKV. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to CHIKV, but generally may differ from one another in terms of frequency of administration. In certain embodiments, however, the amount of antibody to CHIKV contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Therapeutic Methods and Uses

In another aspect, the invention provides a method for preventing infection with CHIKV in a patient in need thereof, or for treating a patient suffering from an infection with CHIKV, or for ameliorating at least one symptom or complication associated with the CHIKV infection, the method comprising administering one or more antibodies or antigen-binding fragments thereof as described herein, or a pharmaceutical composition comprising one or more anti-CHIKV antibodies featured in the invention or fragments thereof, as described herein, to a patient in need thereof, such that the CHIKV infection is prevented, or at least one symptom or complication associated with the infection is ameliorated, alleviated or reduced in severity and/or duration.

In some embodiments, the method reduces a pathology associated with CHIKV infection.

In some embodiments, the method alleviates the symptoms associated with acute, post-acute or chronic polyarthritis/polyarthralgia/CHIKV-associated arthralgia, fever, rash, myalgia and/or fatigue. In one embodiment, the method reduces the pain in a subject associated with the CHIKV infection. In one embodiment, the antibody is used to treat/reduce the symptoms associated with CHIKV infection can cross-react and treat a symptom associated with other alphaviruses infections. In one embodiment, the antibody is used to treat/reduce acute, post-acute and chronic polyarthritis/polyarthralgia phases associated with CHIKV infection.

Examples of such other alphaviruses include, but are not limited to, O'nyong Nyong (ONNV), Ross River (RRV), Barmah Forest (BFV), Western Equine Encephalitis (WEEV), Semliki Forest (SFV), Sindbis (SINV), Eastern Equine Encephalitis (EEEV), Venezuelan Equine Encephalitis (VEEV). Symptoms treated or reduced can include, but are not limited to, pain, fever and the like.

In another embodiment, there is provided a method of treating a subject infected with Chikungunya Virus, or reducing the likelihood of infection of a subject at risk of contracting Chikungunya virus, comprising delivering to said subject an antibody that bind to CHIKV or an antigen-binding fragment according to the invention which comprises CDR sequences from antibodies listed in Tables 2 to 5, respectively.

In another embodiment, there is provided a method of treating a subject infected with Chikungunya Virus, or reducing the likelihood of infection of a subject at risk of contracting Chikungunya virus, comprising delivering to said subject an antibody that bind to CHIKV listed in Tables 2 to 5, respectively. In another embodiment, one, two or several antibodies amongst those listed in Tables 2 to 5 can be combined. In another embodiment, the antibody may be encoding a variant antibody comprising heavy and light chains with variable sequences having 70%, 80%, 90% or 95% identity with the variable sequences of one of the antibodies listed in Tables 2 to 5. The antibody fragment may be a recombinant ScFv (single chain fragment variable) antibody, Fab fragment, F(ab')2 fragment, or Fv fragment. The antibody may be an IgG, and/or a chimeric antibody. The antibody or antibody fragment may be administered prior to infection, or after infection. Delivering may comprise antibody or antibody fragment administration, or genetic delivery with an RNA or DNA sequence or vector encoding the antibody or antibody fragment.

As noted above, the methods of the present invention comprise administering to the subject in need thereof for preventing or treating CHIKV infection/symptoms one antibody as described herein selected from the group consisting of mAb3, mAb4, mAb5, mAb6, mAb7, mAb8, mAb9, mAb10, mAb11, mAb12, mAb13 and mAb14 as listed in tables 2, 3, 4 and 5.

As noted above, the methods of the present invention comprise administering to the subject in need thereof for preventing or treating CHIKV infection/symptoms one antibody as described herein selected from the group consisting of mAb6, mAb7, mAb8, mAb9, mAb13 and mAb14. In another embodiment, the methods of the present invention comprise administering to the subject in need thereof for preventing or treating CHIKV infection/symptoms one antibody feature in the invention selected from the group consisting of mAb7 and mAb14.

In another aspect, the invention relates to a monoclonal antibody as described herein for use as a medicament. In one embodiment, the invention relates to a monoclonal antibody as described herein for use in treatment of CHIKV infection. In one embodiment, the invention relates to a monoclonal antibody for use in treatment of CHIKV-associated arthralgia. In one embodiment, the invention relates to a monoclonal antibody for use in the treatment of acute, post-acute and chronic polyarthritis/polyarthralgia phases associated with CHIKV infection. In one embodiment, the invention relates to a monoclonal antibody for use in treatment of the symptoms associated with acute, post-acute or chronic polyarthritis/polyarthralgia/CHIKV-associated arthralgia, fever, rash, myalgia and/or fatigue. In one embodiment, the invention relates to a monoclonal antibody for use to reduce the pain in a subject associated with a CHIKV infection. In another aspect, the invention relates to a monoclonal antibody for use in the prevention of CHIKV infection. In another embodiment, the invention relates to a monoclonal antibody selected from the group consisting of mAb3, mAb4, mAb5, mAb6, mAb7, mAb8, mAb9, mAb10, mAb11, mAb12, mAb13 and mAb14 as listed in tables 2, 3, 4 and 5 for use in the treatment of the infection and symptoms as listed above. In another embodiment, the invention relates to a monoclonal antibody selected from the group consisting of mAb6, mAb7, mAb8, mAb9, mAb13 and mAb14 as listed in tables 2, 3 and 5 for use in the treatment of the infection and symptoms as listed above. In another embodiment, the invention relates to a monoclonal antibody selected from mAb7 and mAb14 as listed in tables 2 and 5 for use in the treatment of the infection and symptoms as listed above.

In another aspect, the monoclonal anti-CHIKV antibody of the invention or the antigen-binding fragment thereof may be used to prevent or treat CHIKV infection or associated-symptoms in combination with one or more additional therapeutic agents. As used herein, the expression "in combination with" means that the additional therapeutic agents are administered before, after, or concurrent with the pharmaceutical composition comprising the anti-CHIKV antibody featured in the invention. The term "in combination with" also includes sequential or concomitant administration of the anti-CHIKV antibody and a second therapeutic agent.

For example, when administered "before" the pharmaceutical composition comprising the anti-CHIKV antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-CHIKV antibody. When administered "after" the pharmaceutical composition comprising the anti-CHIKV antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-CHIKV antibodies. Administration "concurrent" or with the pharmaceutical composition comprising the anti-CHIKV antibody means that the additional therapeutic agent is administered to the subject in a separate dosage form within less than 5 minutes (before, after, or at the same time) of administration of the pharmaceutical composition comprising the anti-CHIKV antibody, or administered to the subject as a single combined dosage formulation comprising both the additional therapeutic agent and the anti-CHIKV antibody.

Combination therapies may include an anti-CHIKV antibody described herein and any additional therapeutic agent that may be advantageously combined with the antibody, or with a biologically active fragment of the antibody.

For example, a second or third therapeutic agent may be employed to aid in reducing the symptoms associated with a CHIKV infection which include but are not limited to acute, post-acute or chronic polyarthritis polyarthralgia/CHIKV-associated arthralgia, fever, rash, myalgia and/or fatigue. For example, a second or third therapeutic agent may be employed to aid in reducing the pain associated with a CHIKV infection.

Diagnostic Uses

In another aspect, the monoclonal antibody or an antigen-binding fragment featured in the invention is used to detect the presence or the absence of a CHIKV antigen in a sample. In one embodiment, the antibody as described herein is used as a component of an assay comprising a step of contacting a sample with an antibody or an antigen-binding fragment as described herein, a step of detecting the binding of the monoclonal antibody or an antigen-binding fragment to a CHIKV antigen, wherein the detection of the binding indicates the presence of CHIKV antigen or the absence of the detection of the binding to the CHIKV antigen indicates the absence of the CHIKV antigen.

In particular, the monoclonal antibody or an antigen-binding fragment as described herein is used both as component of the therapeutic agent and as component of the diagnostic assay.

In an embodiment, the antibody is intended for an in vitro or ex vivo use. For example, CHIKV may be detected in vitro or ex vivo in a biological sample obtained from a subject, using an anti-CHIKV antibody described herein.

The invention further relates to an in vitro or ex vivo method of detecting the presence of a CHIKV infection in a subject, comprising the steps consisting of:

i. contacting a biological sample of a subject with an anti-CHIKV antibody, in particular in conditions sufficient for the antibody to form complexes with said biological sample,
ii. measuring the level of antibody bound to said biological sample,
iii. detecting the presence of a CHIKV infection by comparing the measured level of bound antibody with a control, an increased level of bound antibody compared to control being indicative of a CHIKV infection.

The invention also relates to an in vitro or ex vivo method of determining susceptibility of a patient infected by CHIKV to a therapeutic agent targeting CHIKV, in particular to an anti-CHIKV antibody or an antigen-binding fragment thereof, as described herein, which method comprises the steps consisting of:

i. contacting a biological sample of a patient infected by CHIKV with an anti-CHIKV antibody or an antigen-binding fragment thereof, in particular in conditions sufficient for the antibody to form complexes with said biological sample,
ii. measuring the level of antibody bound to said biological sample,
iii. comparing the measured level of bound antibody to said biological sample with the level of antibody bound to a control, wherein an increased level of bound antibody to said biological sample compared to control is indicative of a patient susceptible to a therapeutic agent targeting CHIKV.

In the above methods, said control can be a normal, non-infected biological sample of the same type, or a reference value determined to be representative of the antibody binding level in normal biological sample of the same type.

The invention further relates to an in vitro or ex vivo method of monitoring effectiveness of a CHIKV infection therapy, comprising the steps consisting of:

i. contacting a biological sample of a subject undergoing CHIKV infection therapy, with an antibody or an antigen-binding fragment thereof as described herein, in particular in conditions sufficient for the antibody to form complexes with said biological sample, ii. measuring the level of antibody bound to said biological sample, iii. comparing the measured level of bound antibody with the level of antibody bound to a control;

wherein a decreased level of bound antibody to said biological sample compared to control is indicative of effectiveness of said CHIKV infection therapy.

In said method, an increased level of bound antibody to said biological sample compared to control is indicative of ineffectiveness of said CHIKV infection therapy.

Said control is in particular a biological sample of the same type as the biological sample submitted to analysis, but which was obtained from the subject previously in time, during the course of the CHIKV infection therapy.

In an embodiment, anti-CHIKV antibodies or antigen-binding fragment thereof as described herein (e.g., E2-binding fragments) may be labelled with a detectable molecule or substance, such as a fluorescent molecule, a radioactive molecule or any other labels known in the art that provide (either directly or indirectly) a signal.

As used herein, the term "labeled", with regard to the antibody according to the invention, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the polypeptide, as well as indirect labeling of the polypeptide by reactivity with a detectable substance.

"Samples" or "biological sample" that can be used in CHIKV diagnostic assays according to the present invention include any tissue or fluid sample obtainable from a patient under normal or pathological conditions.

Biological samples include but are not limited to blood and other liquid samples of biological origin, solid tissue samples such as a biopsy specimen or tissue cultures or cells derived therefrom, and the progeny thereof. Therefore, biological samples encompass clinical samples, cells in culture, cell supernatants, cell lysates, serum, plasma, biological fluid, and tissue samples.

Kits

The invention also provides kits comprising at least one anti-CHIKV antibody or antigen-binding fragment. Kits containing antibodies or antigen-binding fragments find use in detecting CHIKV, or in therapeutic or diagnostic assays. Kits can contain a polypeptide or antibody coupled to a solid support, e.g. a tissue culture plate or beads (e.g. sepharose beads). Kits can be provided which contain antibodies for detection and quantification of the CHIKV in vitro, e.g. in an ELISA or a Western blot. Such an antibody useful for detection may be provided with a label such as a fluorescent or radiolabel.

In one embodiment, the invention relates to a kit comprising at least one antibody as featured herein and optionally packaging material and optionally a label or packaging insert contained within said packaging material indicating that said antibody as featured herein is effective for preventing/treating CHIKV infection or CHIKV infection related symptoms.

BRIEF DESCRIPTION OF THE SEQUENCES

SEQ ID NO: 1 shows the VH sequence of "mAb1" antibody.

SEQ ID NO: 2 shows the VL sequence of "mAb1" antibody.

SEQ ID NO: 3 shows the VH sequence of "mAb2" antibody.

SEQ ID NO: 4 shows the VL sequence of "mAb2" antibody.

SEQ ID NO: 5-7 show the sequences of the CDR1H, CDR2H, CDR3H of "mAb1" antibody.

SEQ ID NO: 8 shows the sequence of the CDR1L of "mAb1" antibody.

SEQ ID NO: 9 shows the sequence of the recombinant pE2-E1 recombinant target "His-tagged CHIKV E2 LR2006".

SEQ ID NO: 10 shows the sequence of the CDR3L of "mAb1" antibody.

SEQ ID NO: 11-13 show the sequences of the CDR1H, CDR2H, CDR3H of "mAb2" antibody.

SEQ ID NO: 14 shows the sequences of the CDR1L of "mAb2" antibody.

SEQ ID NO: 15 shows the sequence of the recombinant pE2-E1 recombinant target "His-tagged CHIKV E2 SL15649".

SEQ ID NO: 16 shows the sequence of the CDR3L of "mAb2" antibody.

SEQ ID NO: 17 shows the sequence of IgG1 Fc region without substitutions featured in the invention and shown on FIG. 1.

SEQ ID NO: 18 shows the nucleic acid sequence of IgG1 Fc region.

SEQ ID NO: 19 shows the HC sequence of "mAb1" antibody.

SEQ ID NO: 20 shows the LC sequence of "mAb1" antibody.

SEQ ID NO: 21 shows the HC nucleic acid sequence of "mAb1" antibody.

SEQ ID NO: 22 shows the LC nucleic acid sequence of "mAb1" antibody.

SEQ ID NO: 23 shows the HC sequence of "mAb3" antibody.

SEQ ID NO: 24 shows the HC nucleic acid sequence of "mAb3" antibody.

SEQ ID NO: 25 shows the HC sequence of "mAb4" antibody.

SEQ ID NO: 26 shows the HC nucleic acid sequence of "mAb4" antibody.

SEQ ID NO: 27 shows the HC sequence of "mAb5" antibody.

SEQ ID NO: 28 shows the HC nucleic acid sequence of "mAb5" antibody.

SEQ ID NO: 29 shows the HC sequence of "mAb6" antibody.

SEQ ID NO: 30 shows the HC nucleic acid sequence of "mAb6" antibody.

SEQ ID NO: 31 shows the HC sequence of "mAb7" antibody.

SEQ ID NO: 32 shows the HC nucleic acid sequence of "mAb7" antibody.

SEQ ID NO: 33 shows the consensus sequence of the CDRH3 of "mAb2" antibody.

SEQ ID NO: 34 shows the sequence of the CDRH3 of "mAb10" antibody.

SEQ ID NO: 35 shows the sequence of the CDRH3 of "mAb11" antibody.

SEQ ID NO: 36 shows the sequence of the CDRH3 of "mAb12" antibody.

SEQ ID NO: 37 shows the HC sequence of "mAb2" antibody.

SEQ ID NO: 38 shows the LC sequence of "mAb2" antibody.

SEQ ID NO: 39 shows the HC nucleic acid sequence of "mAb2" antibody.
SEQ ID NO: 40 shows the LC nucleic acid sequence of "mAb2" antibody.
SEQ ID NO: 41 shows the HC sequence of "mAb8" antibody.
SEQ ID NO: 42 shows the HC nucleic acid sequence of "mAb8" antibody.
SEQ ID NO: 43 shows the HC sequence of "mAb9" antibody.
SEQ ID NO: 44 shows the HC nucleic acid sequence of "mAb9" antibody.
SEQ ID NO: 45 shows the HC sequence of "mAb10" antibody.
SEQ ID NO: 46 shows the HC nucleic acid sequence of "mAb10" antibody.
SEQ ID NO: 47 shows the HC sequence of "mAb11" antibody.
SEQ ID NO: 48 shows the HC nucleic acid sequence of "mAb11" antibody.
SEQ ID NO: 49 shows the HC sequence of "mAb12" antibody.
SEQ ID NO: 50 shows the HC nucleic acid sequence of "mAb12" antibody.
SEQ ID NO: 51 shows the HC sequence of "mAb13" antibody.
SEQ ID NO: 52 shows the HC nucleic acid sequence of "mAb13" antibody.
SEQ ID NO: 53 shows the HC sequence of "mAb14" antibody.
SEQ ID NO: 54 shows the HC nucleic acid sequence of "mAb14" antibody.
SEQ ID NO: 55 shows the sequence of a IgG1 constant region as shown on FIG. 1.
SEQ ID NO: 56 shows the VH sequence of "mAb10" antibody.
SEQ ID NO: 57 shows the VH sequence of "mAb11" antibody.
SEQ ID NO: 58 shows the VH sequence of "mAb12" antibody.
SEQ ID NO: 59 shows the sequence of a IgG1 Fc region with an alanine at position 434 according to the invention as shown on FIG. 2.
SEQ ID NO: 60 shows the sequence of a IgG1 Fc region with an alanine at positions 307, 380 and 434, respectively, according to the invention as shown on FIG. 2.
SEQ ID NO: 61 shows the sequence of a IgG1 Fc region with a glutamine at position 250 and a leucine at position 428, respectively, according to the invention as shown on FIG. 2.
SEQ ID NO: 62 shows the sequence of a IgG1 Fc region with a tyrosine at position 252, a threonine at position 254 and a glutamic acid at position 256, respectively, according to the invention as shown on FIG. 2.
SEQ ID NO: 63 shows the sequence of a IgG1 Fc region with a leucine at position 428 and a serine at position 434, respectively, according to the invention as shown on FIG. 2.

EXAMPLES

Materials and Methods

Monoclonal Antibodies Analysis and Engineering:

The amino acid sequences of anti-CHIKV antibodies were analyzed using Antibody Inspector (in-house developed tool for antibody sequence analysis) coupled with 3D model/structure analysis tools (Biovia Discovery Studio Suite) to screen potential issues and liabilities for development. The liabilities analysis focus on, solvent exposed unwanted motif like oxidation, deamidation, isomerization, acidic cleavage, glycosylation, and additional free Cys. All the solvent exposed liabilities are prioritized based on their location (CDRs, variable domain frameworks, constant domains). Mutations were suggested to minimize liabilities found in sequences.

Generation of Optimized Antibodies:

Codon-optimized gene fragments were synthesized and cloned into a mammalian expression vector. Transfection was carried out according to the manufacturer's protocol using Expi293F expression system (Thermo Fisher Scientific). Harvested conditioned media samples were purified through Protein A column and the elution fractions were buffer-exchanged into Gibco PBS, pH 7.4.

Binding Analysis: Antigen Binding, FcRn Binding to Human and Mouse, FcγRIIIa Binding:

Recombinant CHIKV E2 antigen binding was measured by surface plasmon resonance using the Biacore T200 instrument. A CM5 series S sensor chip was immobilized with anti-tetra His antibody (Qiagen) at saturating levels via the standard amine coupling procedure provided by Biacore. Recombinant CHIKV E2 antigens i.e. His-tagged CHIKV E2 LR2006 (SEQ ID NO: 9) and His-tagged CHIKV E2 SL15649 (SEQ ID NO: 15) recombinant protein constructs were based on Voss et al., 2010 (Voss J E et al 2010, Nature 468:709-712), transiently expressed by and purified from HEK293 cells (Pal et al, 2013, PLoS Pathog 9, e1003312; Smith et al, 2015, Cell Host & Microbe 18:86-95). Basically, these constructs are designed as signal peptide-E3_E2-(G45)4-E1-His8, but in the mature form, the signal peptide and E3 is cleaved off. His-tagged CHIKV E2 LR2006 and His-tagged CHIKV E2 SL15649 recombinant antigens were diluted in HBS-EP+ running buffer and injected for 30 sec in order to achieve a capture level between 10 and 30 RU. Test antibodies were serially diluted 3-fold from 30 nM to 1.1 nM. Low affinity binders were serially diluted from 900 nM. Each antibody was injected to the captured antigens and control surfaces for 3 min in duplicate at 65 μL/min flow rate with 5 or 15 min dissociation. The surfaces were regenerated with glycine pH 1.5. Kinetic constants were calculated using a 1:1 binding model with the Biacore T200 Evaluation Software.

To measure FcRn binding, a CM5 series S sensor chip was directly immobilized with recombinant human FcRn or mouse FcRn using amine chemistry, achieving a surface density of 1700 RU and 800 RU, respectively. Test antibodies were diluted to 200 and 50 nM in 50 mM sodium phosphate, 150 mM NaCl, 0.05% surfactant P20, pH 6.0 or pH 7.4. The diluted samples were injected for 3 min, followed by 5 min dissociation in buffer at 10 μL/min, in duplicate. The surfaces were regenerated with borate pH 8.5 buffer.

FcγRIIIa binding was measured with the Biacore 3000 instrument. A CM5 chip was immobilized with anti-HPC4 antibody at saturating levels via amine coupling. Two polymorphisms of recombinant human FcγRIIIa were compared in the analysis (Va1158 and Phe158). Recombinant human HPC4-tagged FcγRIIIa-V158 and FcγRIII-F158 were diluted to in HBS-P+ buffer containing 2 mM CaCl2 and injected to Fc2 or Fc4, respectively, for 30 sec at 10 μL/min to achieve a capture level of 10-40 RU. Samples were diluted to 900, 300, and 100 nM and injected for 2 min, followed by 3 min dissociation in buffer at 30 μL/min, in duplicate. The surfaces were regenerated for 3 min with 10 mM EDTA in HBS-EP+ buffer at 20 μL/min.

Results

Example 1

Antigen Binding of mAb2 with Substitutions in CDRH3

The results are presented on FIG. 3. The effects of mutations within CDRH3 of mAb2, introduced to eliminate potential deamidation and oxidation motifs, were measured on the binding to CHIKV pE2-E1 antigen derived from CHIKV strains LR2006. Binding were measured for respectively:

- mAb2 and its derived variants mAb10, mAb11 and mAb12 comprising respectively an isoleucine at position 8 of its CDRH3, a glutamine at position 12 of its CDRH3 and an alanine at position 13 of its CDRH3 as well as for a variant comprising an alanine at position 8 of its CDRH3 and variants comprising different combinations of two substitutions amongst those listed above.

Among the seven mutants created to eliminate potential deamination and oxidation motifs, only mAb11, comprising a glutamine at position 12 of its CDRH3 (mAb2 N108Q) retained a target binding affinity equivalent to the parental mAb. Of note, mAb10 comprising an isoleucine at position 8 of its CDRH3 (mAb2 M104I) and mAb12, comprising an alanine at position 13 of its CDRH3 (mAb2 G109A), presented intermediate profiles; double mutants lost their target binding affinities as well as a variant comprising an alanine at position 8 of its CDRH3 (mAb2 M104A).

Example 2

FcRn Binding

The results are presented on FIG. 4. Binding to human FcRn (FIGS. 4A and 4C) and to mouse (FIGS. 4B and 4D) were measured at pH 6.0. for:

- mAb1 and mAb3, mAb4, mAb5, mAb6 and mAb7 comprising respectively in their Fc regions an alanine at position 434, an alanine at positions 307, 380 and 434, respectively, a glutamine at position 250 and a leucine at position 428, a leucine at position 428 and a serine at position 434, respectively, and a tyrosine at position 252, a threonine at position 254 and a glutamic acid at position 256.
- mAb2 and mAb8, mAb9, mAb11, mAb13 and mAb14 comprising respectively in their Fc regions a tyrosine at position 252, a threonine at position 254 and a glutamic acid at position 256, a leucine at position 428 and a serine at position 434, respectively, a glutamine at position 12 of its CDRH3, a tyrosine at position 252, a threonine at position 254 and a glutamic acid at position 256 as well as a glutamine at position 12 of its CDRH3, a leucine at position 428 and a serine at position 434 as well as a glutamine at position 12 of its CDRH3.

All mutants showed an increase FcRn binding affinity which is expected to result in an increased half-life, and therefore a positive impact on their usefulness in an anti-CHIKV therapy. Mutants comprising a leucine at position 428 and a serine at position 434, respectively, and a tyrosine at position 252, a threonine at position 254 and a glutamic acid at position 256 respectively showed the strongest binding when compared to the other mutants.

Example 3

Effects of Fc Region-Substitutions on mAb1 and mAb2 Target Binding

Figure 5A:
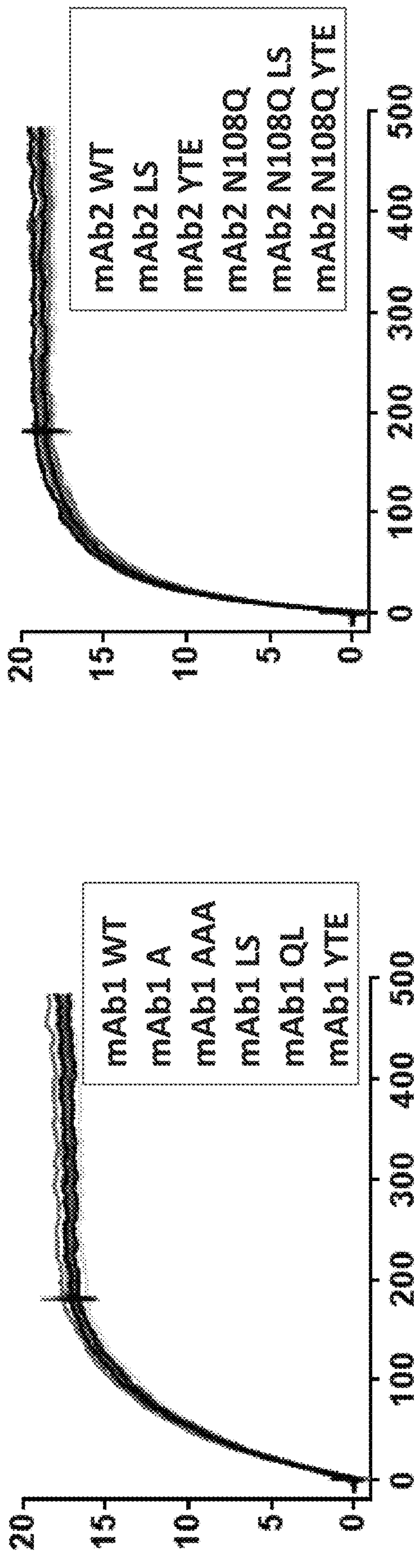
FIG. 5A-B: Effect on E2-E1 target binding of mutations in Fc regions of mAb1 and mAb2 respectively. Results are shown in duplicate for E1-E2 antigen derived from strains LR2006 (FIG. 5A) and SL15649 (FIG. 5B), respectively.
Figure 5B:
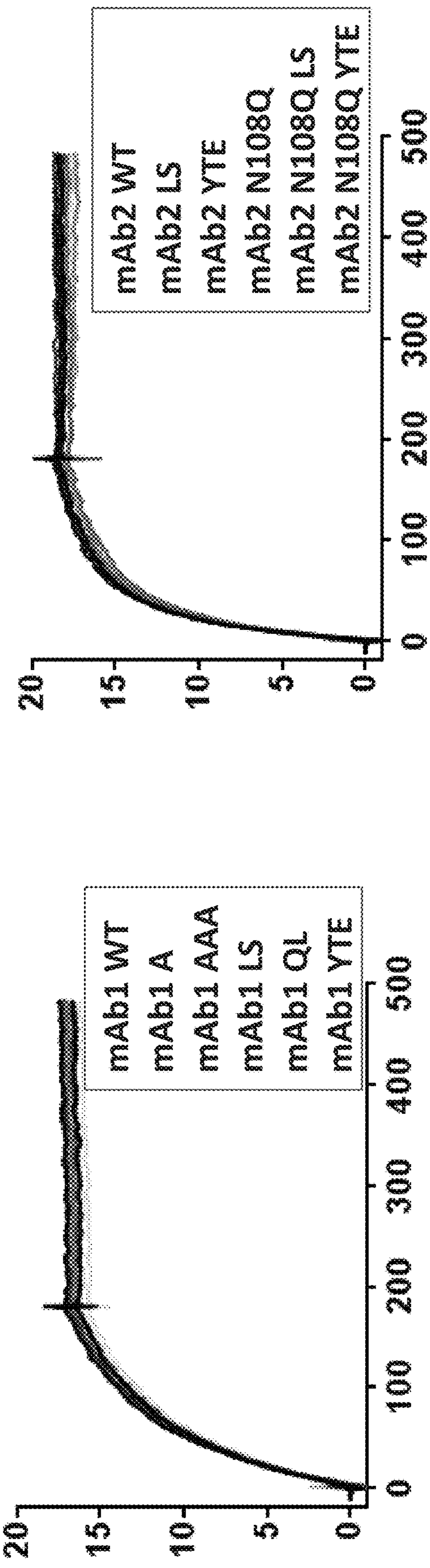

The results are presented on FIG. 5. The effect of substitutions in Fc region were measured for mAb1 and mAb2 on the binding to CHIKV pE2-E1 antigen derived from CHIKV strains LR2006 (FIG. 5A) and SL15649 (FIG. 5B), respectively. Binding were measured for respectively:

- mAb1 and mAb3, mAb4, mAb5, mAb6 and mAb7 comprising respectively an alanine at position 434, an alanine at positions 307, 380 and 434, respectively, a glutamine at position 250 and a leucine at position 428, a leucine at position 428 and a serine at position 434, respectively, and a tyrosine at position 252, a threonine at position 254 and a glutamic acid at position 256.
- mAb2 and mAb8, mAb9, mAb11, mAb13 and mAb14 comprising respectively a tyrosine at position 252, a threonine at position 254 and a glutamic acid at position 256, a leucine at position 428 and a serine at position 434, respectively, a glutamine at position 12 of its CDRH3, a tyrosine at position 252, a threonine at position 254 and a glutamic acid at position 256 as well as a glutamine at position 12 of its CDRH3, a leucine at position 428 and a serine at position 434 as well as a glutamine at position 12 of its CDRH3.

None of the substitutions in Fc region that enhanced the FcRn binding of mAb1 and mAb2 affected the binding to CHIKV targeted pE2-E1 antigen.

Example 4

FcγRIIIa Binding

The results are presented on FIG. 6. The effects of substitutions in the Fc region of mAb1 and mAb2 were measured on the binding to FcγRIIIa respectively. FCγRIIa (CD16a) is expressed by NK and macrophages and is able to induce antibody-dependent cell mediated cytotoxicity (ADCC) and cytokine release by macrophages.

Binding results are shown on human FcγRIIIa high affinity receptor (FcγRIIIaV158) for mAb1 (FIG. 6A) and for mAb2 (FIG. 6B) as well as on human FcγRIIIa low affinity receptor (FcγRIIIaF158), respectively for mAb1 (FIG. 6C) and for mAb2 (FIG. 6D).

Binding were measured for respectively:

- mAb1 and mAb3, mAb4, mAb5, mAb6 and mAb7 comprising respectively an alanine at position 434, an alanine at positions 307, 380 and 434, respectively, a glutamine at position 250 and a leucine at position 428, a leucine at position 428 and a serine at position 434, respectively, and a tyrosine at position 252, a threonine at position 254 and a glutamic acid at position 256.
- mAb2 and mAb8, mAb9, mAb11, mAb13 and mAb14 comprising respectively a tyrosine at position 252, a threonine at position 254 and a glutamic acid at position 256, a leucine at position 428 and a serine at position 434, respectively, a glutamine at position 12 of its CDRH3, a tyrosine at position 252, a threonine at position 254 and a glutamic acid at position 256 as well as a glutamine at position 12 of its CDRH3, a leucine at position 428 and a serine at position 434 as well as a glutamine at position 12 of its CDRH3.

Amongst the substitutions in the Fc region of mAb1 and mAb2 that enhanced FcRn binding, a tyrosine at position 252, a threonine at position 254 and a glutamic acid at position 256 led to a reduced FcγRIIIa binding affinity that could have a negative impact on cell mediated effector functions and anti-CHIKV therapy compared to mAb1 or mAb2 with non-substituted Fc regions. Other mutations such as an alanine at position 434, an alanine at positions 307, 380 and 434, respectively, a glutamine at position 250 and a leucine at position 428, a leucine at position 428 and a serine at position 434, respectively, retained binding affinity toward FcγRIIIa.

MAb1 and mAb2 comprising an alanine at position 434, an alanine at positions 307, 380 and 434, respectively, or a glutamine at position 250 and a leucine at position 428, or a leucine at position 428 and a serine at position 434, respectively, but not a tyrosine at position 252, a threonine at position 254 and a glutamic acid at position 256, retained FcγRIIIa binding that is linked to effector functions. Hence, mAb1 or mAb2 comprising a leucine at position 428 and a serine at position 434 present the best FcRn binding while retaining FcγRIIIa binding which are linked to effector functions.

TABLE 6

Improvement folds of FcRn binding $K_D$ of mAb1 with or without a Fc region carrying one or several substitutions.

| | Ligand | $K_D$ (nM) | Affinity Increase (fold) | Ligand | $K_D$ (nM) | Affinity Increase (fold) | Ligand | $K_D$ (nM) | Ligand | $K_D$ (nM) |
|---|---|---|---|---|---|---|---|---|---|---|
| mAb1 | Human | 348 | 1.0 | Mouse | 20 | 1.0 | Antigen | 0.13 | hFcγRIII | 179 |
| mAb7 | FcRn | 15 | 23.8 | FcRn | 5.9 | 3.4 | (E2) | 0.17 | | 169 |
| mAb6 | | 21 | 16.3 | | 1.9 | 10.4 | | | | 381 |
| mAb5 | | 27 | 13.0 | | 5.9 | 3.3 | | | | 236 |
| mAb4 | | 31 | 11.3 | | 8.4 | 2.3 | | | | 180 |
| mAb3 | | 45 | 7.7 | | 9.3 | 2.1 | | | | 199 |

TABLE 7

Improvement folds of FcRn binding $K_D$ of mAb2 and mAb2 carrying a substitution in CDRH3 with or without a Fc region carrying one or several substitutions.

| | Ligand | $K_D$ (nM) | Affinity Increase (fold) | Ligand | $K_D$ (nM) | Affinity Increase (fold) | Ligand | $K_D$ (nM) | Ligand | $K_D$ (nM) |
|---|---|---|---|---|---|---|---|---|---|---|
| mAb2 | Human | 328 | 1.0 | Mouse | 22 | 1.0 | Antigen | 0.13 | hFcγRIII | 262 |
| mAb9 | FcRn | 20 | 16.6 | FcRn | 7.5 | 3.0 | (E2) | 0.25 | | 207 |
| mAb8 | | 23 | 14.1 | | 1.2 | 19.5 | | | | 499 |
| mAb11 | | 301 | 1.1 | | 20 | 1.1 | | 0.22 | | 289 |
| mAb14 | | 18 | 18.2 | | 6.2 | 3.6 | | 0.12 | | 187 |
| mAb13 | | 24 | 13.7 | | 1.6 | 13.7 | | | | 387 |
| mAb12 | | | | | | | | 0.50 | | |
| mAb10 | | | | | | | | 0.94 | | |

Example 5

Neutralization Activity of mAbs Using Standard Plaque Reduction Assay

MAb1, mAb7 and mAb CTR (Anti-lysozyme rhIgG1 control antibody) were tested in vitro against 3 different prototypic strains of CHIKV (Caribbean, La Reunion (LR) and 37997 strains) that represent the three CHIKV lineages (Asian, East-Central and South African (ESCA) and West African lineages).

Set amount of virus was mixed with an equal volume of antibody diluted in PBS or with diluent. Mixture was incubated at 37° C. for 2 hours. Then the mixture was added to confluent monolayers of vero cells in 6 well plates. After 2 hour incubation, the plates were overlaid with CMC in DMEM-5%. Plates were fixed at 48 hours post injection with formalin and then stained with methylene blue dye. Plaques were counted and data analyzed in Prism-Graph Pad for $EC_{50}$ determination.

Figure 7A:
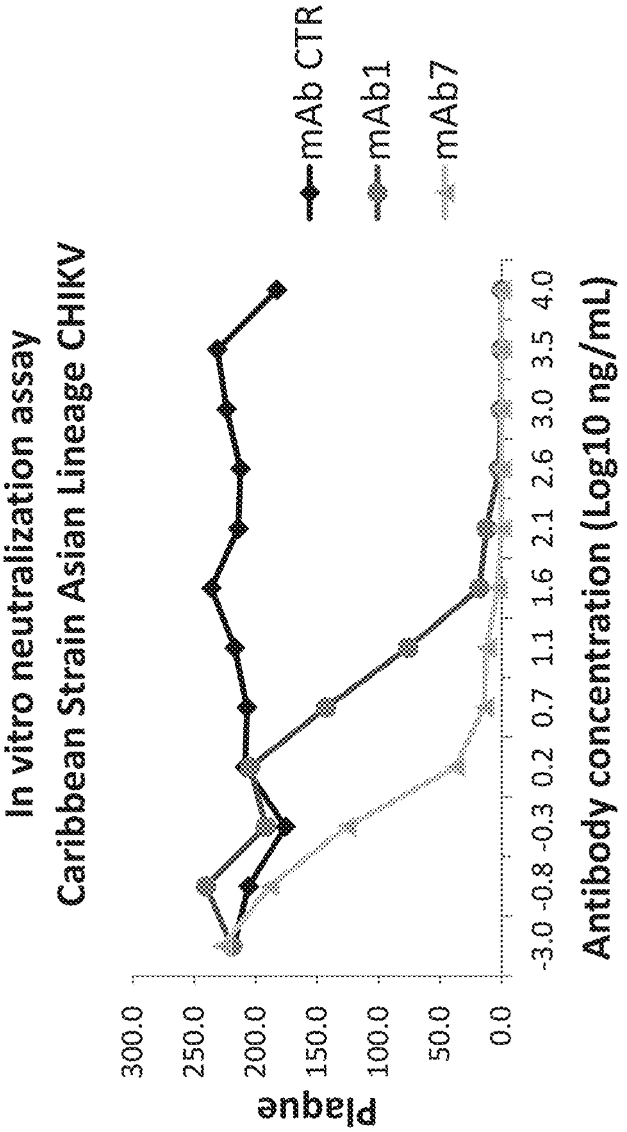
FIG. 7A-C: Neutralization activity of mAb1 and mAb7 using Standard Plaque Reduction Assay. MAb1 and mAb7 inhibit Chikungunya viruses from all three genotypes i.e. Asian (FIG. 7A), East-Central and South African (ESCA) (FIG. 7B) and West African (FIG. 7C) with ultrapotent activity.
Figure 7B:
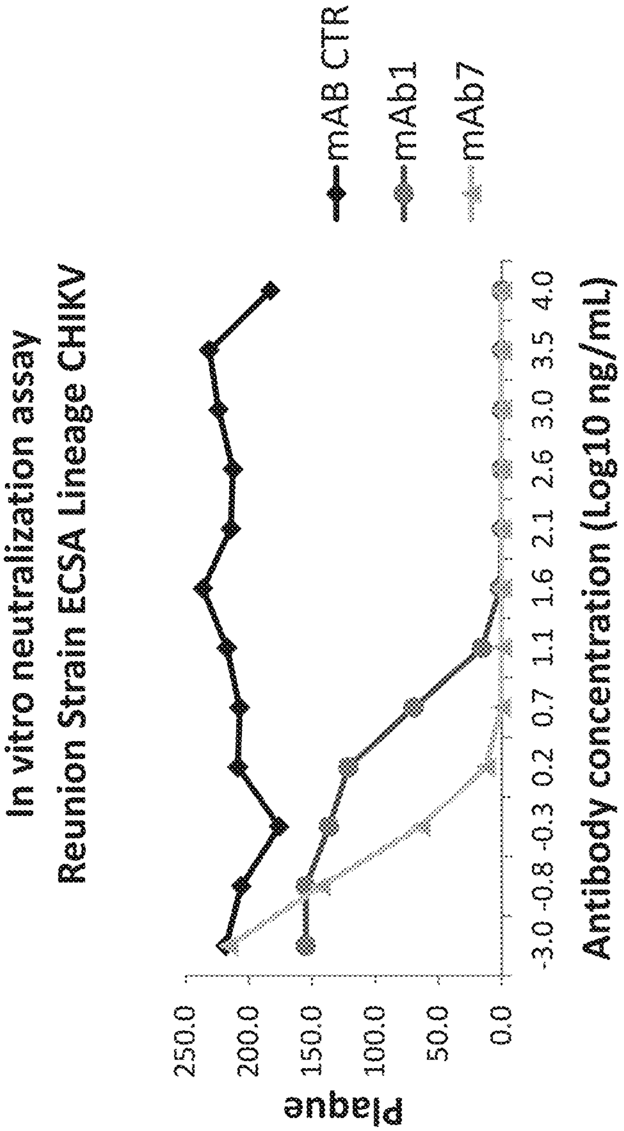
Figure 7C:
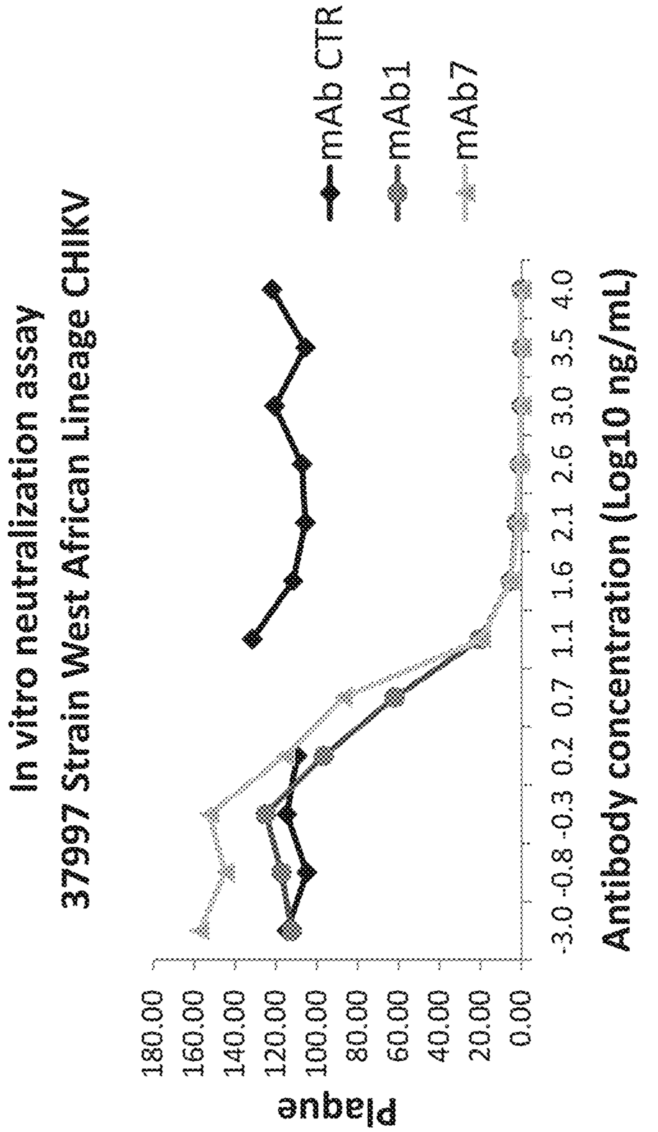

The results are presented in table 8 below as well as on FIGS. 7A to 7C. MAb1 and mAb7 inhibited viruses from all three genotypes with ultrapotent activity ($EC_{50}$ values<10 ng/mL for mAb1 and <1 ng/mL for mAb7) on Asian, East-Central and South African (ESCA) and West African CHIKV lineages as shown on FIGS. 7A, 7B and 7C, respectively. Anti-lysozyme antibody (mAb CTR) was used as non-specific negative control.

TABLE 8

| | In vitro neutralization - $EC_{50}$ (ng/ml) | | |
|---|---|---|---|
| CHIKV Genotype | mAb CTR | mAb1 | mAb7 |
| Caribean Strain Asian Lineage | NA | 7.6 | 0.6 |
| LR Strain ECSA Lineage | NA | 3.9 | 0.3 |
| 37997 Strain West African Lineage | NA | 4.8 | 0.2 |

Example 6

In Vivo Protection Studies in Mice

In vivo studies with DBA1/J mice model were carried out in strict accordance with the recommendations in the Guide for the Care and Use of Laboratory Animals of the National Institutes of Health. The protocols were approved by the Institutional Animal Care and Use Committee at National Institute of Allergy and Infection Diseases (NIAID). Infection experiments were performed in A-BSL3 facilities with the approval of the NIAID Animal Studies Committee.

7-8 week old DBA/1J mice were inoculated by 0.05 ml subcutaneously in the right hind footpad toward the ankle, with CHIKV-LR2006. For therapeutic studies, a single dose of recombinant human IgG anti-CHIKV individual mAbs at specified doses was administered by intra-peritoneal route at 3 days post CHIKV infection using subcutaneous inoculation in the footpad with $10^{5.5}$ $CCID_{50}$/0.1 ml of CHIKV-LR2006. Virus titer in the site of injection was monitored at 5 days post-infection. For prophylaxis studies, recombinant human IgG anti-CHIKV mAbs were administered by intra-peritoneal injection either at 2, 7 or 14 days prior to subcutaneous infection in the footpad with $10^{5.5}$ $CCID_{50}$/0.1 ml of CHIKV-LR2006. Virus titer in the site of injection was monitored at 3 days post-infection.

MAb Prophylaxis In Vivo.

Figure 8:
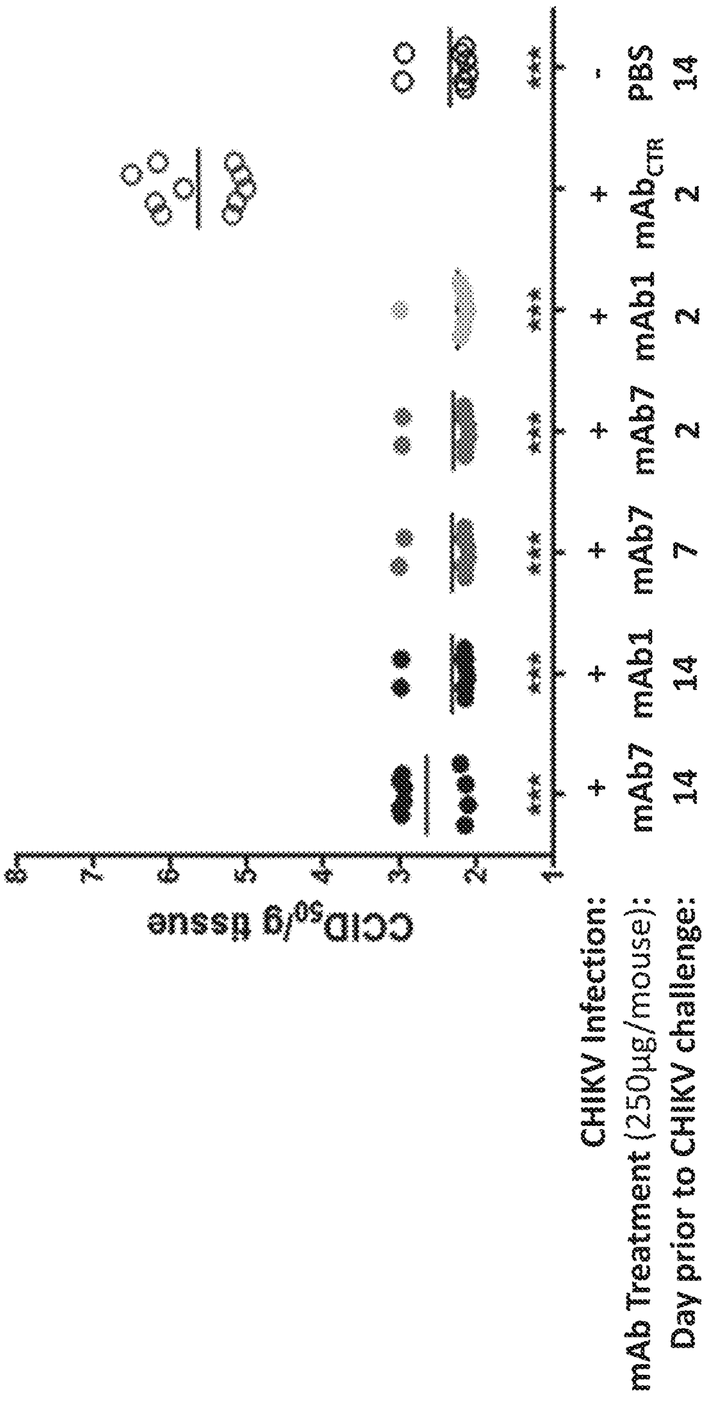
FIG. 8: Mab prophylaxis studies in mice. Effect of mAb1 and mAb7 given at 250 μg/mouse at 2, 7 or 14 days prior to CHIKV infection on the virus titer at 3 days post-inoculation in the right hind leg of DBA/1J mice. Viral titer is plotted as 50% cell culture infectious dose ($CCID_{50}$) per gram of tissue.

Mice were pre-treated with a single 250 μg dose (~12.5 mg/kg) of recombinant hIgG anti-CHIKV mAbs (mAb1, mAb7) or anti-lysozyme isotype control mAb ($mAbc_{CTR}$) either at 2, 7 or 14 days before subcutaneous injection with CHIKV-LR2006. All mice treated with the isotype control mAb exhibited a high virus titer in the right hind leg ($CCID_{50}$/g tissue) at 3 days post-inoculation (FIG. 8). Pretreatment with both mAb7 and mAb1, at the different time prior to infection (−2 to −14 days), completely protected DBA1/J-mice from virus burden at the site of injection as their respective virus level in the right hind leg was comparable to non-infected mice from SHAM-PBS group.

Figure 9A:
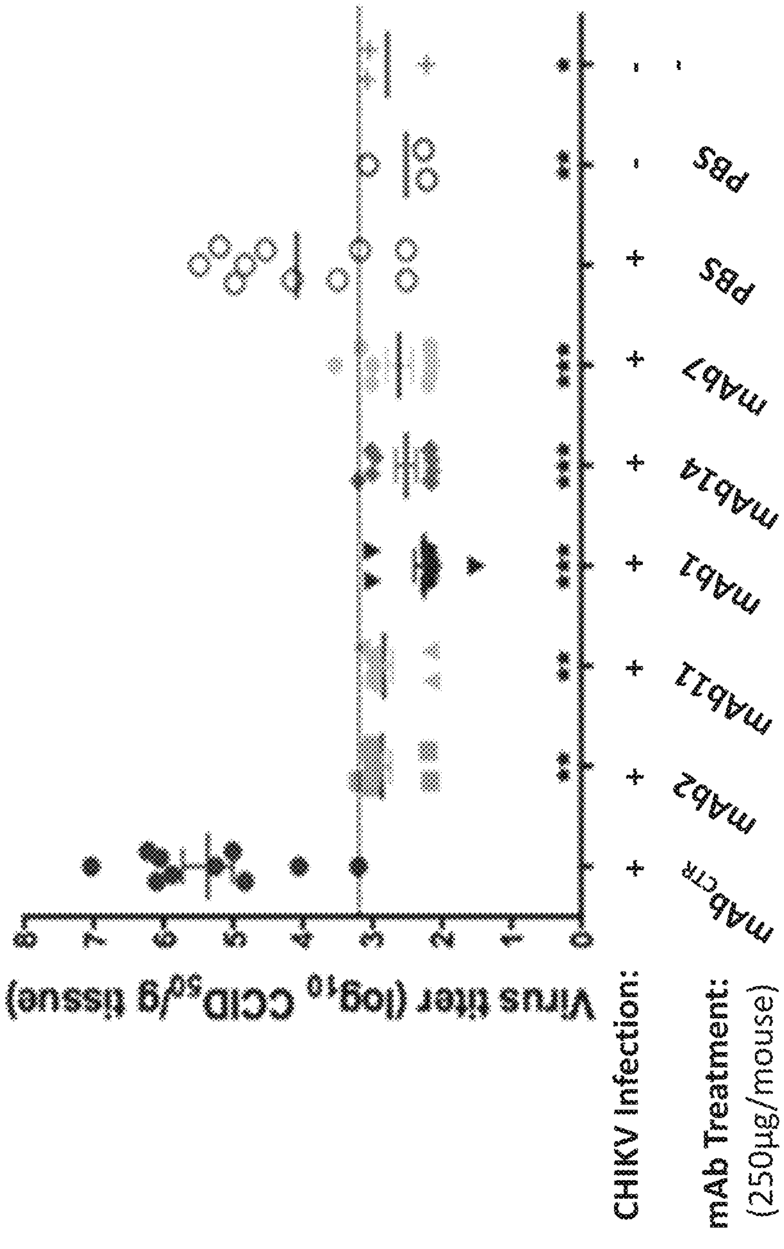
FIG. 9A-B: Mab post-exposure therapy in mice. Virus titer in the Right Hind Leg at 5 days post-inoculation (dpi) after single intra-peritoneal administration of fixed 250 μg dose of mAbs 2, 7, 11 and 14 at 3 dpi (FIG. 9A). Dose range effect on virus titer in the Right Hind Leg at 5 dpi of mAb7 and mAb14 after single administration of various doses (from 10 to 250 μg/mouse) at 3 dpi (FIG. 9B). Viral titer is plotted as 50% cell culture infectious dose ($CCID_{50}$) per gram of tissue. Upper dashed line is the average limit of detection for tissue homogenates.
Figure 9B:
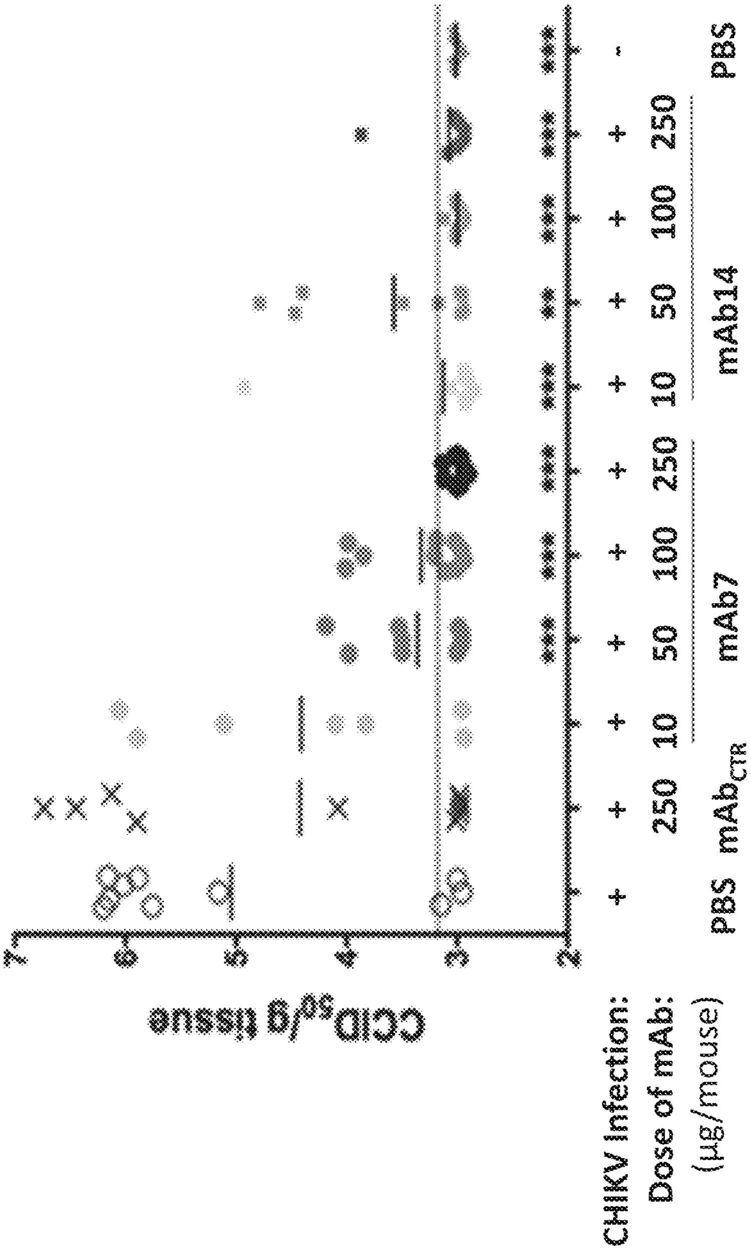

MAb Post-Exposure Therapy In Vivo 7-8 week old DBA/1J mice were inoculated by 0.05 ml subcutaneously in the right hind footpad toward the ankle, with 105.5 $CCID_{50}$/0.1 ml of CHIKV-LR. A single 250 μg dose of individual mAb (mAb1, mAb2, mAb7, mAb11 or mAb14) was administered by intra-peritoneal route at 3 days post CHIKV infection. Virus titer in the site of injection was monitored at 5 days post-infection. All tested mAbs exhibited the same potency to neutralize tissue viral load in the mouse model of CHIKV infection (FIG. 9A). MAb7 and mAb14 were further characterized in a dose titration study. To that purpose, DBA1/J mice were inoculated by 0.05 ml subcutaneously in the right hind footpad toward the ankle, with 105.5 $CCID_{50}$/0.1 ml of CHIKV-LR2006. MAb7 or mAb14 were given at 3 dpi by single intra-peritoneal injection at 10, 25, 50, 100 and 250 μg doses (~0.5, 1, 2.5, 5, 12.5 mg/kg). The primary outcome was virus titer in the hind limb at the site of virus challenge on 5 dpi. The mAb7 reduced the joint viral titer in a dose dependent manner in CHIKV-infected DBA/1J mice (FIG. 9B). Significant reduction is observed from 50 to 250 μg dose with the maximal effect achieved at the highest dose. The mAb14 significantly reduced viral titer whatever the dose but no dose-effect was observed in tested conditions.

Example 7

Mab Pharmacokinetics in Non-Human Primate

Figure 10:
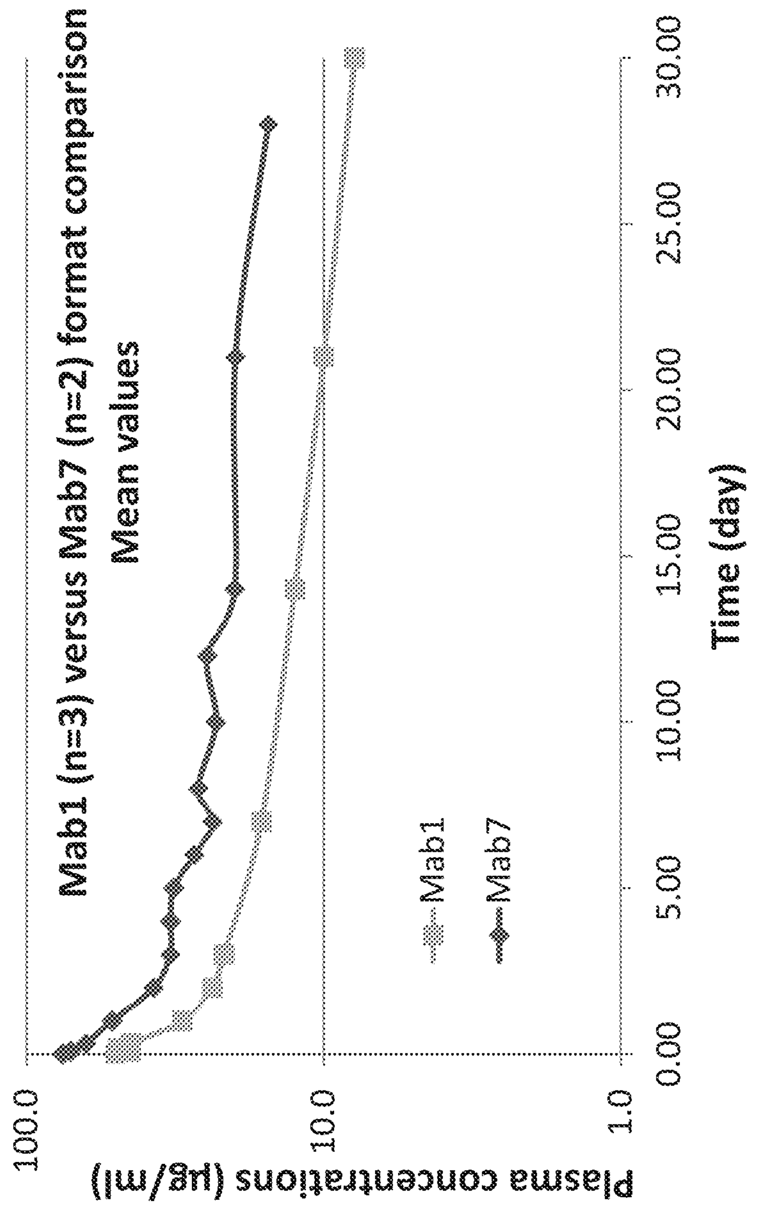
FIG. 10: Mab Pharmacokinetics in Non-Human Primate. Comparison of pharmacokinetics for mAb1 and mAb7 administered by intravenous (IV) bolus, 2.5 mg/kg into male Cynomolgus Monkey (Macaca Fascicularis).

MAb1 and mAb7 were administered by intravenous (IV) bolus, 2.5 mg/kg into male Cynomolgus Monkey (Macaca Fascicularis). Animals receiving mab1 and mab7 were different (two separate studies). Plasma samples were assayed with an exploratory Elisa bioanalytical method using antibodies against human IgG1 and thereby recognizing mAb1 and mAb7 developed by rabbit immunization. Comparison of pharmacokinetics showed an increase of terminal half-life (i.e. $t_{1/2}$, the period of time required for the concentration or amount of drug in the body to be reduced to exactly one-half) with mAb7 with 22.7 and 25.5 days for mAb1 and mAb7 respectively (FIG. 10).

The invention claimed is:

1. A polynucleotide comprising a sequence encoding an isolated monoclonal antibody that binds to CHIKV and that comprises three Heavy Chain Complementary Determining Regions (CDRHs) and three Light Chain Complementary Determining Regions (CDRLs), wherein:

i. said CDRHs have amino acid sequences of SEQ ID NO: 5, 6 and 7, and said CDRLs have amino acid sequences of SEQ ID NO: 8, GNT and 10, or ii. said CDRHs have amino acid sequences of SEQ ID NO: 11, 12 and 13, and said CDRLs have amino acid sequences of SEQ ID NO: 14, GTS and 16, and wherein said antibody further comprises a Fc region comprising a leucine at position 428 and a serine at position 434, respectively, wherein said amino acid positions in the Fc region are given according to the EU index.

2. The polynucleotide of claim 1, wherein the polynucleotide comprises a sequence encoding a light chain, wherein the sequence encoding the light chain has at least 95% identity with a sequence selected from the group consisting of SEQ ID NOs: 22 and 40 and/or a sequence encoding a heavy chain, wherein the sequence encoding the heavy chain has at least 95% identity with a sequence selected from the group consisting of SEQ ID NOs: 32 and 44.

3. The polynucleotide of claim 1, wherein the polynucleotide comprises a sequence encoding a light chain, wherein the sequence encoding the light chain has at least 96% identity with a sequence selected from the group consisting of SEQ ID NOs: 22 and 40 and/or a sequence encoding a heavy chain, wherein the sequence encoding the heavy chain has at least 96% identity with a sequence selected from the group consisting of SEQ ID NOs: 32 and 44.

4. The polynucleotide of claim 1, wherein the polynucleotide comprises a sequence encoding a light chain, wherein the sequence encoding the light chain has at least 97% identity with a sequence selected from the group consisting of SEQ ID NOs: 22 and 40 and/or a sequence encoding a heavy chain, wherein the sequence encoding the heavy chain has at least 97% identity with a sequence selected from the group consisting of SEQ ID NOs: 32 and 44.

5. The polynucleotide of claim 1, wherein the polynucleotide comprises the sequence of SEQ ID: 44.

6. The polynucleotide of claim 1, wherein the polynucleotide comprises the sequence of SEQ ID: 40.

7. The polynucleotide of claim 1, wherein the polynucleotide comprises the sequence of SEQ ID NO: 32.

8. The polynucleotide of claim 1, wherein the polynucleotide comprises the sequence of SEQ ID NO: 22.

9. The polynucleotide of claim 1, wherein said antibody comprises three Heavy Chain Complementary Determining Regions (CDRHs) having amino acid sequences of SEQ ID NO: 5, 6 and 7, respectively, and wherein said antibody comprises three Light Chain Complementary Determining Regions (CDRLs) having amino acid sequences of SEQ ID NO: 8, GNT and 10, respectively.

10. The polynucleotide of claim 9, wherein the Fc region comprises the sequence of SEQ ID NO: 63.

11. The polynucleotide of claim 9, wherein said antibody further comprises a heavy chain variable region comprising the sequence of SEQ ID NO: 1 and a light chain variable region comprising the sequence of SEQ ID NO: 2.

12. The polynucleotide of claim 9, wherein said antibody further comprises a heavy chain comprising the sequence of SEQ ID NO: 31 and a light chain comprising the sequence of SEQ ID NO: 20.

13. The polynucleotide of claim 1, wherein said antibody comprises three Heavy Chain Complementary Determining Regions (CDRHs) having amino acid sequences of SEQ ID NO: 11, 12 and 13, respectively, and said antibody comprises three Light Chain Complementary Determining Regions (CDRLs) having amino acid sequences of SEQ ID NO: 14, GTS and 16, respectively.

14. The polynucleotide of claim 13, wherein the Fc region comprises the sequence of SEQ ID NO: 63.

15. The polynucleotide of claim 13, wherein said antibody further comprises a heavy chain variable region comprising the sequence of SEQ ID NO: 3 and a light chain variable region comprising the sequence of SEQ ID NO: 4.

16. The polynucleotide of claim 13, wherein said antibody further comprises a light chain comprising the sequence of SEQ ID NO: 38 and a heavy chain comprising the sequence of SEQ ID NO: 43.

17. A vector comprising the polynucleotide of claim 1.

18. An isolated host cell line comprising the vector of claim 17.

19. The polynucleotide of claim 1, wherein the polynucleotide comprises a sequence encoding a light chain, wherein the sequence encoding the light chain has at least 98% identity with a sequence selected from the group consisting of SEQ ID NOs: 22 and 40 and/or a sequence encoding a heavy chain, wherein the sequence encoding the heavy chain has at least 98% identity with a sequence selected from the group consisting of SEQ ID NOs: 32 and 44.

20. The polynucleotide of claim 1, wherein the polynucleotide comprises a sequence encoding a light chain, wherein the sequence encoding the light chain has at least 99% identity with a sequence selected from the group consisting of SEQ ID NOs: 22 and 40 and/or a sequence encoding a heavy chain, wherein the sequence encoding the heavy chain has at least 99% identity with a sequence selected from the group consisting of SEQ ID NOs: 32 and 44.

21. The polynucleotide of claim 1, wherein the polynucleotide has a sequence selected from the group consisting of SEQ ID NOs: 22, 32, 40, and 44.

22. The polynucleotide of claim 1, wherein the polynucleotide comprises a sequence encoding a light chain, wherein the sequence encoding the light chain has at least 95% identity with a sequence selected from the group consisting of SEQ ID NOs: 22 and 40 and/or a sequence encoding a heavy chain, wherein the sequence encoding the heavy chain has at least 95% identity with a sequence selected from the group consisting of SEQ ID NOs: 32 and 44 and wherein the light chain comprises a variable light chain region comprising a sequence of SEQ ID NO: 2 or SEQ ID NO: 4 and wherein the heavy chain comprises a variable heavy chain region comprising a sequence of SEQ ID NO: 1 or SEQ ID NO: 3.

* * * * *

UNITED STATES PATENT AND TRADEMARK OFFICE

CERTIFICATE OF CORRECTION

PATENT NO. : 12,227,560 B2
APPLICATION NO. : 17/672871
DATED : February 18, 2025
INVENTOR(S) : Carter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 52 days.

Signed and Sealed this
Twenty-ninth Day of July, 2025

Coke Morgan Stewart
*Acting Director of the United States Patent and Trademark Office*

SEQUENCE LISTING

```
<160> NUMBER OF SEQ ID NOS: 63

<210> SEQ ID NO 1
<211> LENGTH: 126
<212> TYPE: PRT
<213> ORGANISM: Artificial Sequence
<220> FEATURE:
<223> OTHER INFORMATION: VH mAb1

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95
```

-continued

```
Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser
        115                 120                 125


<210> SEQ ID NO 2
<211> LENGTH: 111
<212> TYPE: PRT
<213> ORGANISM: Artificial Sequence
<220> FEATURE:
<223> OTHER INFORMATION: VL mAb1

<400> SEQUENCE: 2

Gln Ala Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr Asn Val His Trp Tyr Gln Leu Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu
            100                 105                 110


<210> SEQ ID NO 3
<211> LENGTH: 123
<212> TYPE: PRT
<213> ORGANISM: Artificial Sequence
<220> FEATURE:
<223> OTHER INFORMATION: VH mAb2

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Gly Val Asp Tyr
            100                 105                 110

Trp Gly Gln Gly Thr Leu Val Thr Val Ser Ser
        115                 120


<210> SEQ ID NO 4
<211> LENGTH: 107
<212> TYPE: PRT
<213> ORGANISM: Artificial Sequence
<220> FEATURE:
<223> OTHER INFORMATION: VL mAb2
```

<400> SEQUENCE: 4

Gln Ala Val Val Thr Gln Ser Pro Ser Ser Leu Pro Ala Ser Val Gly
1 5 10 15

Asp Arg Val Thr Ile Thr Cys Arg Ala Ser Gln Asp Ile Arg Asn Asn
20 25 30

Leu Gly Trp Tyr Gln Gln Lys Pro Gly Lys Ala Pro Glu Arg Leu Ile
35 40 45

Tyr Gly Thr Ser Asn Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Ser Tyr Pro Pro
85 90 95

Thr Phe Gly Arg Gly Thr Lys Val Glu Ile Lys
100 105

<210> SEQ ID NO 5
<211> LENGTH: 8
<212> TYPE: PRT
<213> ORGANISM: Artificial Sequence
<220> FEATURE:
<223> OTHER INFORMATION: CDRH1 mAb1

<400> SEQUENCE: 5

Gly Tyr Ser Phe Thr Ser Tyr Gly
1 5

<210> SEQ ID NO 6
<211> LENGTH: 8
<212> TYPE: PRT
<213> ORGANISM: Artificial Sequence
<220> FEATURE:
<223> OTHER INFORMATION: CDRH2 mAb1

<400> SEQUENCE: 6

Ile Ser Thr Tyr Lys Gly Tyr Thr
1 5

<210> SEQ ID NO 7
<211> LENGTH: 19
<212> TYPE: PRT
<213> ORGANISM: Artificial Sequence
<220> FEATURE:
<223> OTHER INFORMATION: CDRH3 mAb1

<400> SEQUENCE: 7

Ala Arg Val Leu Ser Glu Thr Gly Tyr Phe Tyr Tyr Tyr Tyr Tyr Gly
1 5 10 15

Met Asp Val

<210> SEQ ID NO 8
<211> LENGTH: 9
<212> TYPE: PRT
<213> ORGANISM: Artificial Sequence
<220> FEATURE:
<223> OTHER INFORMATION: CDRL1 mAb1

<400> SEQUENCE: 8

Ser Ser Asn Ile Gly Ala Asp Tyr Asn
1 5

-continued

<210> SEQ ID NO 9
<211> LENGTH: 863
<212> TYPE: PRT
<213> ORGANISM: Artificial Sequence
<220> FEATURE:
<223> OTHER INFORMATION: His-tagged CHIKVE2 LR2006

<400> SEQUENCE: 9

```
Ser Leu Ala Ile Pro Val Met Cys Leu Leu Ala Asn Thr Thr Phe Pro
1               5                   10                  15

Cys Ser Gln Pro Pro Cys Thr Pro Cys Cys Tyr Glu Lys Glu Pro Glu
            20                  25                  30

Glu Thr Leu Arg Met Leu Glu Asp Asn Val Met Arg Pro Gly Tyr Tyr
        35                  40                  45

Gln Leu Leu Gln Ala Ser Leu Thr Cys Ser Pro His Arg Gln Arg Arg
    50                  55                  60

Ser Thr Lys Asp Asn Phe Asn Val Tyr Lys Ala Thr Arg Pro Tyr Leu
65                  70                  75                  80

Ala His Cys Pro Asp Cys Gly Glu Gly His Ser Cys His Ser Pro Val
                85                  90                  95

Ala Leu Glu Arg Ile Arg Asn Glu Ala Thr Asp Gly Thr Leu Lys Ile
            100                 105                 110

Gln Val Ser Leu Gln Ile Gly Ile Lys Thr Asp Asp Ser His Asp Trp
        115                 120                 125

Thr Lys Leu Arg Tyr Met Asp Asn His Met Pro Ala Asp Ala Glu Arg
    130                 135                 140

Ala Gly Leu Phe Val Arg Thr Ser Ala Pro Cys Thr Ile Thr Gly Thr
145                 150                 155                 160

Met Gly His Phe Ile Leu Ala Arg Cys Pro Lys Gly Glu Thr Leu Thr
                165                 170                 175

Val Gly Phe Thr Asp Ser Arg Lys Ile Ser His Ser Cys Thr His Pro
            180                 185                 190

Phe His His Asp Pro Pro Val Ile Gly Arg Glu Lys Phe His Ser Arg
        195                 200                 205

Pro Gln His Gly Lys Glu Leu Pro Cys Ser Thr Tyr Val Gln Ser Thr
    210                 215                 220

Ala Ala Thr Thr Glu Glu Ile Glu Val His Met Pro Pro Asp Thr Pro
225                 230                 235                 240

Asp Arg Thr Leu Met Ser Gln Gln Ser Gly Asn Val Lys Ile Thr Val
                245                 250                 255

Asn Gly Gln Thr Val Arg Tyr Lys Cys Asn Cys Gly Gly Ser Asn Glu
            260                 265                 270

Gly Leu Thr Thr Thr Asp Lys Val Ile Asn Asn Cys Lys Val Asp Gln
        275                 280                 285

Cys His Ala Ala Val Thr Asn His Lys Lys Trp Gln Tyr Asn Ser Pro
    290                 295                 300

Leu Val Pro Arg Asn Ala Glu Leu Gly Asp Arg Lys Gly Lys Ile His
305                 310                 315                 320

Ile Pro Phe Pro Leu Ala Asn Val Thr Cys Arg Val Pro Lys Ala Arg
                325                 330                 335

Asn Pro Thr Val Thr Tyr Gly Lys Asn Gln Val Ile Met Leu Leu Tyr
            340                 345                 350

Pro Asp His Pro Thr Leu Leu Ser Tyr Arg Asn Met Gly Glu Glu Pro
        355                 360                 365
```

-continued

```
Asn Tyr Gln Glu Glu Trp Val Met His Lys Lys Glu Val Val Leu Thr
    370                 375                 380

Val Pro Thr Glu Gly Leu Glu Val Thr Trp Gly Asn Asn Glu Pro Tyr
385                 390                 395                 400

Lys Tyr Trp Pro Gln Leu Ser Thr Asn Gly Thr Ala His Gly His Pro
                405                 410                 415

His Glu Ile Ile Leu Tyr Tyr Tyr Glu Gly Gly Gly Gly Ser Gly Gly
            420                 425                 430

Gly Gly Ser Gly Gly Gly Gly Ser Gly Gly Gly Gly Tyr Glu His Val
        435                 440                 445

Thr Val Ile Pro Asn Thr Val Gly Val Pro Tyr Lys Thr Leu Val Asn
    450                 455                 460

Arg Pro Gly Tyr Ser Pro Met Val Leu Glu Met Glu Leu Leu Ser Val
465                 470                 475                 480

Thr Leu Glu Pro Thr Leu Ser Leu Asp Tyr Ile Thr Cys Glu Tyr Lys
                485                 490                 495

Thr Val Ile Pro Ser Pro Tyr Val Lys Cys Cys Gly Thr Ala Glu Cys
            500                 505                 510

Lys Asp Lys Asn Leu Pro Asp Tyr Ser Cys Lys Val Phe Thr Gly Val
        515                 520                 525

Tyr Pro Phe Met Trp Gly Gly Ala Tyr Cys Phe Cys Asp Ala Glu Asn
    530                 535                 540

Thr Gln Leu Ser Glu Ala His Val Glu Lys Ser Glu Ser Cys Lys Thr
545                 550                 555                 560

Glu Phe Ala Ser Ala Tyr Arg Ala His Thr Ala Ser Ala Ser Ala Lys
                565                 570                 575

Leu Arg Val Leu Tyr Gln Gly Asn Asn Ile Thr Val Thr Ala Tyr Ala
            580                 585                 590

Asn Gly Asp His Ala Val Thr Val Lys Asp Ala Lys Phe Ile Val Gly
        595                 600                 605

Pro Met Ser Ser Ala Trp Thr Pro Phe Asp Asn Lys Ile Val Val Tyr
    610                 615                 620

Lys Gly Asp Val Tyr Asn Met Asp Tyr Pro Pro Phe Gly Ala Gly Arg
625                 630                 635                 640

Pro Gly Gln Phe Gly Asp Ile Gln Ser Arg Thr Pro Glu Ser Lys Asp
                645                 650                 655

Val Tyr Ala Asn Thr Gln Leu Val Leu Gln Arg Pro Ala Val Gly Thr
            660                 665                 670

Val His Val Pro Tyr Ser Gln Ala Pro Ser Gly Phe Lys Tyr Trp Leu
        675                 680                 685

Lys Glu Arg Gly Ala Ser Leu Gln His Thr Ala Pro Phe Gly Cys Gln
    690                 695                 700

Ile Ala Thr Asn Pro Val Arg Ala Val Asn Cys Ala Val Gly Asn Met
705                 710                 715                 720

Pro Ile Ser Ile Asp Ile Pro Glu Ala Ala Phe Thr Arg Val Val Asp
                725                 730                 735

Ala Pro Ser Leu Thr Asp Met Ser Cys Glu Val Pro Ala Cys Thr His
            740                 745                 750

Ser Ser Asp Phe Gly Gly Val Ala Ile Ile Lys Tyr Ala Ala Ser Lys
        755                 760                 765

Lys Gly Lys Cys Ala Val His Ser Met Thr Asn Ala Val Thr Ile Arg
    770                 775                 780
```

Glu Ala Glu Ile Glu Val Glu Gly Asn Ser Gln Leu Gln Ile Ser Phe
785 790 795 800

Ser Thr Ala Leu Ala Ser Ala Glu Phe Arg Val Gln Val Cys Ser Thr
805 810 815

Gln Val His Cys Ala Ala Glu Cys His Pro Pro Lys Asp His Ile Val
820 825 830

Asn Tyr Pro Ala Ser His Thr Thr Leu Gly Val Gln Asp Ile Ser Ala
835 840 845

Thr Ala Met Ser Trp Val Gln His His His His His His His His
850 855 860

<210> SEQ ID NO 10
<211> LENGTH: 11
<212> TYPE: PRT
<213> ORGANISM: Artificial Sequence
<220> FEATURE:
<223> OTHER INFORMATION: CDRL3 mAb1

<400> SEQUENCE: 10

Gln Ser Tyr Asp Ser Ser Leu Ser Ala Ser Val
1 5 10

<210> SEQ ID NO 11
<211> LENGTH: 8
<212> TYPE: PRT
<213> ORGANISM: Artificial Sequence
<220> FEATURE:
<223> OTHER INFORMATION: CDRH1 mAb2

<400> SEQUENCE: 11

Gly Tyr Ile Leu Ser Lys Leu Ser
1 5

<210> SEQ ID NO 12
<211> LENGTH: 8
<212> TYPE: PRT
<213> ORGANISM: Artificial Sequence
<220> FEATURE:
<223> OTHER INFORMATION: CDRH2 mAb2

<400> SEQUENCE: 12

Ser Glu Arg Glu Asp Gly Glu Thr
1 5

<210> SEQ ID NO 13
<211> LENGTH: 16
<212> TYPE: PRT
<213> ORGANISM: Artificial Sequence
<220> FEATURE:
<223> OTHER INFORMATION: CDRH3 mAb2

<400> SEQUENCE: 13

Ala Thr Gly Gly Phe Trp Ser Met Ile Gly Gly Asn Gly Val Asp Tyr
1 5 10 15

<210> SEQ ID NO 14
<211> LENGTH: 6
<212> TYPE: PRT
<213> ORGANISM: Artificial Sequence
<220> FEATURE:
<223> OTHER INFORMATION: CDRL1 mAb2

<400> SEQUENCE: 14

Gln Asp Ile Arg Asn Asn
1 5

<210> SEQ ID NO 15
<211> LENGTH: 863
<212> TYPE: PRT
<213> ORGANISM: Artificial Sequence
<220> FEATURE:
<223> OTHER INFORMATION: His-tagged CHIKVE2 SL15649

<400> SEQUENCE: 15

```
Ser Leu Ala Ile Pro Val Met Cys Leu Leu Ala Asn Thr Thr Phe Pro
1               5                   10                  15

Cys Ser Gln Pro Pro Cys Thr Pro Cys Cys Tyr Glu Lys Glu Pro Glu
            20                  25                  30

Glu Thr Leu Arg Met Leu Glu Asp Asn Val Met Arg Pro Gly Tyr Tyr
        35                  40                  45

Gln Leu Leu Gln Ala Ser Leu Thr Cys Ser Pro His Arg Gln Arg Arg
    50                  55                  60

Ser Thr Lys Asp Asn Phe Asn Val Tyr Lys Ala Thr Arg Pro Tyr Leu
65                  70                  75                  80

Ala His Cys Pro Asp Cys Gly Glu Gly His Ser Cys His Ser Pro Val
                85                  90                  95

Ala Leu Glu Arg Ile Arg Asn Glu Ala Thr Asp Gly Thr Leu Lys Ile
            100                 105                 110

Gln Val Ser Leu Gln Ile Gly Ile Lys Thr Asp Asp Ser His Asp Trp
        115                 120                 125

Thr Lys Leu Arg Tyr Met Asp Asn His Met Pro Ala Asp Ala Glu Arg
    130                 135                 140

Ala Gly Leu Phe Val Arg Thr Ser Ala Pro Cys Thr Ile Thr Gly Thr
145                 150                 155                 160

Met Gly His Phe Ile Leu Ala Arg Cys Pro Lys Gly Glu Thr Leu Thr
                165                 170                 175

Val Gly Phe Thr Asp Ser Arg Lys Ile Ser His Ser Cys Thr His Pro
            180                 185                 190

Phe His His Asp Pro Pro Val Ile Gly Arg Glu Lys Phe His Ser Arg
        195                 200                 205

Pro Gln His Gly Lys Glu Leu Pro Cys Ser Thr Tyr Val Gln Ser Thr
    210                 215                 220

Ala Ala Thr Thr Glu Glu Ile Glu Val His Met Pro Pro Asp Thr Pro
225                 230                 235                 240

Asp Arg Thr Leu Met Ser Gln Gln Ser Gly Asn Val Lys Ile Thr Val
                245                 250                 255

Asn Gly Gln Thr Val Arg Tyr Lys Cys Asn Cys Gly Gly Ser Asn Glu
            260                 265                 270

Gly Leu Thr Thr Thr Asp Lys Val Ile Asn Asn Cys Lys Val Asp Gln
        275                 280                 285

Cys His Ala Ala Val Thr Asn His Lys Lys Trp Gln Tyr Asn Ser Pro
    290                 295                 300

Leu Val Pro Arg Asn Ala Glu Leu Gly Asp Arg Lys Gly Lys Ile His
305                 310                 315                 320

Ile Pro Phe Pro Leu Ala Asn Val Thr Cys Arg Val Pro Lys Ala Arg
                325                 330                 335

Asn Pro Thr Val Thr Tyr Gly Lys Asn Gln Val Ile Met Leu Leu Tyr
            340                 345                 350

Pro Asp His Pro Thr Leu Leu Ser Tyr Arg Asn Met Gly Glu Glu Pro
        355                 360                 365
```

-continued

```
Asn Tyr Gln Glu Glu Trp Val Met His Lys Lys Glu Val Val Leu Thr
    370                 375                 380

Val Pro Thr Glu Gly Leu Glu Val Thr Trp Gly Asn Asn Glu Pro Tyr
385                 390                 395                 400

Lys Tyr Trp Pro Gln Leu Ser Thr Asn Gly Thr Ala His Gly His Pro
                405                 410                 415

His Glu Ile Ile Leu Tyr Tyr Tyr Glu Gly Gly Gly Gly Ser Gly Gly
            420                 425                 430

Gly Gly Ser Gly Gly Gly Gly Ser Gly Gly Gly Gly Tyr Glu His Val
        435                 440                 445

Thr Val Ile Pro Asn Thr Val Gly Val Pro Tyr Lys Thr Leu Val Asn
    450                 455                 460

Arg Pro Gly Tyr Ser Pro Met Val Leu Glu Met Glu Leu Leu Ser Val
465                 470                 475                 480

Thr Leu Glu Pro Thr Leu Ser Leu Asp Tyr Ile Thr Cys Glu Tyr Lys
                485                 490                 495

Thr Val Ile Pro Ser Pro Tyr Val Lys Cys Cys Gly Thr Ala Glu Cys
            500                 505                 510

Lys Asp Lys Asn Leu Pro Asp Tyr Ser Cys Lys Val Phe Thr Gly Val
        515                 520                 525

Tyr Pro Phe Met Trp Gly Gly Ala Tyr Cys Phe Cys Asp Ala Glu Asn
    530                 535                 540

Thr Gln Leu Ser Glu Ala His Val Glu Lys Ser Glu Ser Cys Lys Thr
545                 550                 555                 560

Glu Phe Ala Ser Ala Tyr Arg Ala His Thr Ala Ser Ala Ser Ala Lys
                565                 570                 575

Leu Arg Val Leu Tyr Gln Gly Asn Asn Ile Thr Val Thr Ala Tyr Ala
            580                 585                 590

Asn Gly Asp His Ala Val Thr Val Lys Asp Ala Lys Phe Ile Val Gly
        595                 600                 605

Pro Met Ser Ser Ala Trp Thr Pro Phe Asp Asn Lys Ile Val Val Tyr
    610                 615                 620

Lys Gly Asp Val Tyr Asn Met Asp Tyr Pro Pro Phe Gly Ala Gly Arg
625                 630                 635                 640

Pro Gly Gln Phe Gly Asp Ile Gln Ser Arg Thr Pro Glu Ser Lys Asp
                645                 650                 655

Val Tyr Ala Asn Thr Gln Leu Val Leu Gln Arg Pro Ala Ala Gly Thr
            660                 665                 670

Val His Val Pro Tyr Ser Gln Ala Pro Ser Gly Phe Lys Tyr Trp Leu
        675                 680                 685

Lys Glu Arg Gly Ala Ser Leu Gln His Thr Ala Pro Phe Gly Cys Gln
    690                 695                 700

Ile Ala Thr Asn Pro Val Arg Ala Val Asn Cys Ala Val Gly Asn Met
705                 710                 715                 720

Pro Ile Ser Ile Asp Ile Pro Glu Ala Ala Phe Thr Arg Val Val Asp
                725                 730                 735

Ala Pro Ser Leu Thr Asp Met Ser Cys Glu Val Leu Ala Cys Thr His
            740                 745                 750

Ser Ser Asp Phe Gly Gly Val Ala Ile Ile Lys Tyr Ala Ala Ser Lys
        755                 760                 765

Lys Gly Lys Cys Ala Val His Ser Met Thr Asn Ala Val Thr Ile Arg
    770                 775                 780
```

-continued

```
Glu Ala Glu Ile Glu Val Glu Gly Asn Ser Gln Leu Gln Ile Ser Phe
785                 790                 795                 800

Ser Thr Ala Leu Ala Ser Ala Glu Phe Arg Val Gln Val Cys Ser Thr
                805                 810                 815

Gln Val His Cys Ala Ala Glu Cys His Pro Pro Lys Asp His Ile Val
            820                 825                 830

Asn Tyr Pro Ala Ser His Thr Thr Leu Gly Val Gln Asp Ile Ser Ala
        835                 840                 845

Thr Ala Met Ser Trp Val Gln His His His His His His His His
    850                 855                 860


<210> SEQ ID NO 16
<211> LENGTH: 9
<212> TYPE: PRT
<213> ORGANISM: Artificial Sequence
<220> FEATURE:
<223> OTHER INFORMATION: CDRL3 mAb2

<400> SEQUENCE: 16

Leu Gln His Asn Ser Tyr Pro Pro Thr
1               5


<210> SEQ ID NO 17
<211> LENGTH: 221
<212> TYPE: PRT
<213> ORGANISM: Artificial Sequence
<220> FEATURE:
<223> OTHER INFORMATION: IgG1 Fc region without substitution

<400> SEQUENCE: 17

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220
```

```
<210> SEQ ID NO 18
<211> LENGTH: 663
<212> TYPE: DNA
<213> ORGANISM: Artificial Sequence
<220> FEATURE:
<223> OTHER INFORMATION: IgG1 Fc region without substitution nucleic
      acid sequence
<220> FEATURE:
<221> NAME/KEY: exon
<222> LOCATION: (1)..(663)

<400> SEQUENCE: 18

tgt ccc cct tgt cct gcc cct gaa ctg ctg ggc gga cct tcc gtg ttc       48
Cys Pro Pro Cys Pro Ala Pro Glu Leu Leu Gly Gly Pro Ser Val Phe
1               5                   10                  15

ctg ttc ccc cca aag ccc aag gac acc ctg atg atc agc cgg acc ccc       96
Leu Phe Pro Pro Lys Pro Lys Asp Thr Leu Met Ile Ser Arg Thr Pro
            20                  25                  30

gaa gtg acc tgc gtg gtg gtg gat gtg tcc cac gag gac cct gaa gtg      144
Glu Val Thr Cys Val Val Val Asp Val Ser His Glu Asp Pro Glu Val
        35                  40                  45

aag ttc aat tgg tac gtg gac ggc gtg gaa gtg cac aac gcc aag acc      192
Lys Phe Asn Trp Tyr Val Asp Gly Val Glu Val His Asn Ala Lys Thr
    50                  55                  60

aag ccc aga gag gaa cag tac aac tcc acc tac cgg gtg gtg tcc gtg      240
Lys Pro Arg Glu Glu Gln Tyr Asn Ser Thr Tyr Arg Val Val Ser Val
65                  70                  75                  80

ctg aca gtg ctg cac cag gac tgg ctg aac ggc aaa gag tac aag tgc      288
Leu Thr Val Leu His Gln Asp Trp Leu Asn Gly Lys Glu Tyr Lys Cys
                85                  90                  95

aag gtg tcc aac aaa gcc ctg cct gcc ccc atc gag aaa acc atc agc      336
Lys Val Ser Asn Lys Ala Leu Pro Ala Pro Ile Glu Lys Thr Ile Ser
            100                 105                 110

aag gcc aag ggc cag ccc cgc gaa ccc cag gtg tac aca ctg cct ccc      384
Lys Ala Lys Gly Gln Pro Arg Glu Pro Gln Val Tyr Thr Leu Pro Pro
        115                 120                 125

agc agg gac gag ctg acc aag aac cag gtg tcc ctg acc tgt ctc gtg      432
Ser Arg Asp Glu Leu Thr Lys Asn Gln Val Ser Leu Thr Cys Leu Val
    130                 135                 140

aaa ggc ttc tac ccc tcc gat atc gcc gtg gaa tgg gag agc aac ggc      480
Lys Gly Phe Tyr Pro Ser Asp Ile Ala Val Glu Trp Glu Ser Asn Gly
145                 150                 155                 160

cag ccc gag aac aac tac aag acc acc ccc cct gtg ctg gac agc gac      528
Gln Pro Glu Asn Asn Tyr Lys Thr Thr Pro Pro Val Leu Asp Ser Asp
                165                 170                 175

ggc tca ttc ttc ctg tac agc aag ctg acc gtg gac aag tcc cgg tgg      576
Gly Ser Phe Phe Leu Tyr Ser Lys Leu Thr Val Asp Lys Ser Arg Trp
            180                 185                 190

cag cag ggc aac gtg ttc agc tgc agc gtg atg cac gag gcc ctg cac      624
Gln Gln Gly Asn Val Phe Ser Cys Ser Val Met His Glu Ala Leu His
        195                 200                 205

aac cac tac aca cag aag tcc ctg agc ctg agc ccc ggc                  663
Asn His Tyr Thr Gln Lys Ser Leu Ser Leu Ser Pro Gly
    210                 215                 220


<210> SEQ ID NO 19
<211> LENGTH: 455
<212> TYPE: PRT
<213> ORGANISM: Artificial Sequence
<220> FEATURE:
<223> OTHER INFORMATION: HC mAb1
```

<400> SEQUENCE: 19

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415
```

```
Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly
    450                 455


<210> SEQ ID NO 20
<211> LENGTH: 217
<212> TYPE: PRT
<213> ORGANISM: Artificial Sequence
<220> FEATURE:
<223> OTHER INFORMATION: LC mAb1

<400> SEQUENCE: 20

Gln Ala Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr Asn Val His Trp Tyr Gln Leu Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 21
<211> LENGTH: 1368
<212> TYPE: DNA
<213> ORGANISM: Artificial Sequence
<220> FEATURE:
<223> OTHER INFORMATION: HC mAb1 nucleic acid sequence

<400> SEQUENCE: 21

caggtgcagc tggtgcagtc tggcgccgaa gtgaagaaac caggcgccag cgtgaaggtg      60

tcctgcaagg ccagcggcta cagcttcacc agctacggca tcagctgggt gcgccaggct     120

cctggacagg gcctggaatg gatgggctgg atcagcacct acaagggcta cacccagtac     180

gcccagaact tccagggcag agtgaccatc accaccgaca cccctgccac caccgtgtac     240
```

-continued

```
atggaactgc ggagcctgag aagcgacgac accgccgtgt actactgcgc cagagtgctg    300

agcgagacag gctactttta ctactactat tacggcatgg acgtgtgggg ccagggcacc    360

ctcgtgacag tgtctagcgc ctctacaaag ggccccagcg tgttccctct ggcccctagc    420

agcaagagca catctggcgg aacagccgcc ctgggctgcc tcgtgaagga ctactttccc    480

gagcccgtga ccgtgtcctg gaacagcggc gctctgacct ctggcgtgca cacctttcca    540

gccgtgctgc agagcagcgg cctgtactct ctgagcagcg tcgtgactgt gcccagcagc    600

agcctgggaa cccagaccta catctgcaac gtgaaccaca agcccagcaa caccaaggtg    660

gacaagaagg tggaacccaa gagctgcgac aagacccaca cctgtccccc ttgtcctgcc    720

cctgaactgc tgggcggacc ttccgtgttc ctgttccccc caaagcccaa ggacaccctg    780

atgatcagcc ggacccccga agtgacctgc gtggtggtgg atgtgtccca cgaggaccct    840

gaagtgaagt tcaattggta cgtggacggc gtggaagtgc acaacgccaa gaccaagccc    900

agagaggaac agtacaactc cacctaccgg gtggtgtccg tgctgacagt gctgcaccag    960

gactggctga acggcaaaga gtacaagtgc aaggtgtcca acaaagccct gcctgccccc   1020

atcgagaaaa ccatcagcaa ggccaagggc cagccccgcg aaccccaggt gtacacactg   1080

cctcccagca gggacgagct gaccaagaac caggtgtccc tgacctgtct cgtgaaaggc   1140

ttctacccct ccgatatcgc cgtggaatgg gagagcaacg gccagcccga gaacaactac   1200

aagaccaccc cccctgtgct ggacagcgac ggctcattct tcctgtacag caagctgacc   1260

gtggacaagt cccggtggca gcagggcaac gtgttcagct gcagcgtgat gcacgaggcc   1320

ctgcacaacc actacacaca gaagtccctg agcctgagcc ccggctga                1368
```

<210> SEQ ID NO 22
<211> LENGTH: 654
<212> TYPE: DNA
<213> ORGANISM: Artificial Sequence
<220> FEATURE:
<223> OTHER INFORMATION: LC mAb1 nucleic acid sequence

<400> SEQUENCE: 22

```
caggctgtcg tgacacagcc tcctagcgtg tcaggcgccc ctggccagag agtgaccatc     60

agctgtacag gcagcagcag caacatcgga gccgactaca acgtgcactg gtatcagctg    120

ctgcccggca ccgcccctaa gctgctgatc tacggcaaca ccaaccggcc tagcggcgtg    180

cccgatagat tcagcggcag caagagcggc acaagcgcca gcctggccat tactggactg    240

caggccgagg acgaggccga ctactactgc cagagctacg acagcagcct gagcgcctcc    300

gtgtttggcg gcggaacaaa gctgacagtg ctgggccagc ctaaggccgc tccaagcgtg    360

accctgttcc ctccaagcag cgaggaactg caggctaaca aggccaccct cgtgtgcctg    420

atcagcgact tctatcctgg cgccgtgacc gtggcctgga aggccgatag ctctcctgtg    480

aaggccggcg tggaaaccac caccccctagc aagcagagca acaacaaata cgccgccagc    540

agctacctga gcctgacccc cgagcagtgg aagtcccaca gatcctacag ctgccaagtg    600

acccacgagg gcagcaccgt ggaaaagaca gtggccccta ccgagtgctc ctga          654
```

<210> SEQ ID NO 23
<211> LENGTH: 455
<212> TYPE: PRT
<213> ORGANISM: Artificial Sequence
<220> FEATURE:
<223> OTHER INFORMATION: HC mAb3

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415
```

-continued

```
Ser Lys Leu Thr Val Asp Lys Ser Arg Trp Gln Gln Gly Asn Val Phe
            420                 425                 430

Ser Cys Ser Val Met His Glu Ala Leu His Ala His Tyr Thr Gln Lys
        435                 440                 445

Ser Leu Ser Leu Ser Pro Gly
    450                 455
```

<210> SEQ ID NO 24
<211> LENGTH: 1368
<212> TYPE: DNA
<213> ORGANISM: Artificial Sequence
<220> FEATURE:
<223> OTHER INFORMATION: HC mAb3 nucleic acid sequence

<400> SEQUENCE: 24

```
caggtgcagc tggtgcagtc tggcgccgaa gtgaagaaac caggcgccag cgtgaaggtg     60

tcctgcaagg ccagcggcta cagcttcacc agctacggca tcagctgggt gcgccaggct    120

cctggacagg gcctggaatg gatgggctgg atcagcacct acaagggcta cacccagtac    180

gcccagaact tccagggcag agtgaccatc accaccgaca cccctgccac caccgtgtac    240

atggaactgc ggagcctgag aagcgacgac accgccgtgt actactgcgc cagagtgctg    300

agcgagacag gctactttta ctactactat tacggcatgg acgtgtgggg ccagggcacc    360

ctcgtgacag tgtctagcgc cagcacaaag ggccccagcg tgttccctct ggccccctagc    420

agcaagagca catctggcgg aacagccgcc ctgggctgcc tcgtgaagga ctactttccc    480

gagcccgtga ccgtgtcctg gaacagcggc gctctgacct ctggcgtgca cacctttcca    540

gccgtgctgc agagcagcgg cctgtactct ctgagcagcg tcgtgactgt gcccagcagc    600

agcctgggaa cccagaccta catctgcaac gtgaaccaca agcccagcaa caccaaggtg    660

gacaagaagg tggaacccaa gagctgcgac aagacccaca cctgtccccc ttgtcctgcc    720

cctgaactgc tgggcggacc ttccgtgttc ctgttccccc caaagcccaa ggacaccctg    780

atgatcagcc ggacccccga agtgacctgc gtggtggtgg atgtgtccca cgaggaccct    840

gaagtgaagt tcaattggta cgtggacggc gtggaagtgc acaacgccaa gaccaagccc    900

agagaggaac agtacaactc cacctaccgg gtggtgtccg tgctgacagt gctgcaccag    960

gactggctga acggcaaaga gtacaagtgc aaggtgtcca acaaagccct gcctgccccc   1020

atcgagaaaa ccatcagcaa ggccaagggc cagccccgcg aaccccaggt gtacacactg   1080

cctcccagca gggacgagct gaccaagaac caggtgtccc tgacctgtct cgtgaaaggc   1140

ttctacccct ccgatatcgc cgtggaatgg gagagcaacg gccagcccga gaacaactac   1200

aagaccaccc cccctgtgct ggacagcgac ggctcattct tcctgtacag caagctgacc   1260

gtggacaagt cccggtggca gcagggcaac gtgttcagct gcagcgtgat gcacgaggcc   1320

ctgcacgccc actacacaca gaagtccctg agcctgagcc ccggctga                1368
```

<210> SEQ ID NO 25
<211> LENGTH: 455
<212> TYPE: PRT
<213> ORGANISM: Artificial Sequence
<220> FEATURE:
<223> OTHER INFORMATION: HC mAb4

<400> SEQUENCE: 25

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ser Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Ala Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Ala Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430
```

```
Ser Cys Ser Val Met His Glu Ala Leu His Ala His Tyr Thr Gln Lys
        435                 440                 445

Ser Leu Ser Leu Ser Pro Gly
    450                 455
```

<210> SEQ ID NO 26
<211> LENGTH: 1368
<212> TYPE: DNA
<213> ORGANISM: Artificial Sequence
<220> FEATURE:
<223> OTHER INFORMATION: HC mAb4 nucleic acid sequence

<400> SEQUENCE: 26

```
caggtgcagc tggtgcagtc tggcgccgaa gtgaagaaac caggcgccag cgtgaaggtg     60

tcctgcaagg ccagcggcta cagcttcacc agctacggca tcagctgggt gcgccaggct    120

cctggacagg gcctggaatg gatgggctgg atcagcacct acaagggcta cacccagtac    180

gcccagaact tccagggcag agtgaccatc accaccgaca cccctgccac caccgtgtac    240

atggaactgc ggagcctgag aagcgacgac accgccgtgt actactgcgc cagagtgctg    300

agcgagacag gctactttta ctactactat tacggcatgg acgtgtgggg ccagggcacc    360

ctcgtgacag tgtctagcgc cagcacaaag ggccccagcg tgttccctct ggcccctagc    420

agcaagagca catctggcgg aacagccgcc ctgggctgcc tcgtgaagga ctactttccc    480

gagcccgtga ccgtgtcctg gaacagcggc gctctgacct ctggcgtgca cacctttcca    540

gccgtgctgc agagcagcgg cctgtactct ctgagcagcg tcgtgactgt gcccagcagc    600

agcctgggaa cccagaccta catctgcaac gtgaaccaca agcccagcaa caccaaggtg    660

gacaagaagg tggaacccaa gagctgcgac aagacccaca cctgtccccc ttgtcctgcc    720

cctgaactgc tgggcggacc ttccgtgttc ctgttccccc caaagcccaa ggacaccctg    780

atgatcagcc ggacccccga agtgacctgc gtggtggtgg atgtgtccca cgaggaccct    840

gaagtgaagt tcaattggta cgtggacggc gtggaagtgc acaacgccaa gaccaagccc    900

agagaggaac agtacaactc cacctaccgg gtggtgtccg tgctggctgt gctgcaccag    960

gactggctga acggcaaaga gtacaagtgc aaggtgtcca acaaagccct gcctgccccc   1020

atcgagaaaa ccatcagcaa ggccaagggc cagccccgcg aaccccaggt gtacacactg   1080

cctcccagca gggacgagct gaccaagaac caggtgtccc tgacctgtct cgtgaaaggc   1140

ttctacccct ccgatatcgc cgtggcctgg gagagcaacg gccagcccga gaacaactac   1200

aagaccaccc cccctgtgct ggacagcgac ggctcattct tcctgtacag caagctgacc   1260

gtggacaagt cccggtggca gcagggcaac gtgttcagct gcagcgtgat gcacgaggcc   1320

ctgcacgccc actacacaca gaagtccctg agcctgagcc ccggctga                 1368
```

<210> SEQ ID NO 27
<211> LENGTH: 455
<212> TYPE: PRT
<213> ORGANISM: Artificial Sequence
<220> FEATURE:
<223> OTHER INFORMATION: HC mAb5

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30
```

-continued

```
Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Gln Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430
```

```
Ser Cys Ser Val Leu His Glu Ala Leu His Asn His Tyr Thr Gln Lys
        435                 440                 445

Ser Leu Ser Leu Ser Pro Gly
    450                 455
```

<210> SEQ ID NO 28
<211> LENGTH: 1368
<212> TYPE: DNA
<213> ORGANISM: Artificial Sequence
<220> FEATURE:
<223> OTHER INFORMATION: HC mAb5 nucleic acid sequence

<400> SEQUENCE: 28

```
caggtgcagc tggtgcagtc tggcgccgaa gtgaagaaac caggcgccag cgtgaaggtg      60

tcctgcaagg ccagcggcta cagcttcacc agctacggca tcagctgggt gcgccaggct     120

cctggacagg gcctggaatg gatgggctgg atcagcacct acaagggcta cacccagtac     180

gcccagaact tccagggcag agtgaccatc accaccgaca cccctgccac caccgtgtac     240

atggaactgc ggagcctgag aagcgacgac accgccgtgt actactgcgc cagagtgctg     300

agcgagacag gctacttttta ctactactat tacggcatgg acgtgtgggg ccagggcacc     360

ctcgtgacag tgtctagcgc cagcacaaag ggccccagcg tgttccctct ggcccctagc     420

agcaagagca catctggcgg aacagccgcc ctgggctgcc tcgtgaagga ctactttccc     480

gagcccgtga ccgtgtcctg gaacagcggc gctctgacct ctggcgtgca cacctttcca     540

gccgtgctgc agagcagcgg cctgtactct ctgagcagcg tcgtgactgt gcccagcagc     600

agcctgggaa cccagaccta catctgcaac gtgaaccaca agcccagcaa caccaaggtg     660

gacaagaagg tggaacccaa gagctgcgac aagacccaca cctgtccccc ttgtcctgcc     720

cctgaactgc tgggcggacc ttccgtgttc ctgttccccc caaagcccaa ggaccagctg     780

atgatcagcc ggacccccga agtgacctgc gtggtggtgg atgtgtccca cgaggaccct     840

gaagtgaagt tcaattggta cgtggacggc gtggaagtgc acaacgccaa gaccaagccc     900

agagaggaac agtacaactc cacctaccgg gtggtgtccg tgctgacagt gctgcaccag     960

gactggctga acggcaaaga gtacaagtgc aaggtgtcca acaaagccct gcctgccccc    1020

atcgagaaaa ccatcagcaa ggccaagggc cagccccgcg aaccccaggt gtacacactg    1080

cctcccagca gggacgagct gaccaagaac caggtgtccc tgacctgtct cgtgaaaggc    1140

ttctacccct ccgatatcgc cgtggaatgg gagagcaacg gccagcccga gaacaactac    1200

aagaccaccc cccctgtgct ggacagcgac ggctcattct tcctgtacag caagctgacc    1260

gtggacaagt cccggtggca gcagggcaac gtgttcagct gcagcgtgct gcacgaggcc    1320

ctgcacaacc actacacaca gaagtccctg agcctgagcc ccggctga                 1368
```

<210> SEQ ID NO 29
<211> LENGTH: 455
<212> TYPE: PRT
<213> ORGANISM: Artificial Sequence
<220> FEATURE:
<223> OTHER INFORMATION: HC mAb6

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30
```

-continued

```
Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Tyr Ile Thr Arg Glu Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430
```

Ser Cys Ser Val Met His Glu Ala Leu His Asn His Tyr Thr Gln Lys
435 440 445

Ser Leu Ser Leu Ser Pro Gly
450 455

<210> SEQ ID NO 30
<211> LENGTH: 1368
<212> TYPE: DNA
<213> ORGANISM: Artificial Sequence
<220> FEATURE:
<223> OTHER INFORMATION: HC mAb6 nucleic acid sequence

<400> SEQUENCE: 30
caggtgcagc tggtgcagtc tggcgccgaa gtgaagaaac caggcgccag cgtgaaggtg 60
tcctgcaagg ccagcggcta cagcttcacc agctacggca tcagctgggt gcgccaggct 120
cctggacagg gcctggaatg gatgggctgg atcagcacct acaagggcta cacccagtac 180
gcccagaact tccagggcag agtgaccatc accaccgaca cccctgccac caccgtgtac 240
atggaactgc ggagcctgag aagcgacgac accgccgtgt actactgcgc cagagtgctg 300
agcgagacag gctacttta ctactactat tacggcatgg acgtgtgggg ccagggcacc 360
ctcgtgacag tgtctagcgc cagcacaaag ggccccagcg tgttccctct ggcccctagc 420
agcaagagca catctggcgg aacagccgcc ctgggctgcc tcgtgaagga ctactttccc 480
gagcccgtga ccgtgtcctg gaacagcggc gctctgacct ctggcgtgca cacctttcca 540
gccgtgctgc agagcagcgg cctgtactct ctgagcagcg tcgtgactgt gcccagcagc 600
agcctgggaa cccagaccta catctgcaac gtgaaccaca agcccagcaa caccaaggtg 660
gacaagaagg tggaacccaa gagctgcgac aagacccaca cctgtccccc ttgtcctgcc 720
cctgaactgc tgggcggacc ttccgtgttc ctgttccccc caaagcccaa ggacaccctg 780
tacatcaccc gcgagcccga agtgacctgc gtggtggtgg atgtgtccca cgaggaccct 840
gaagtgaagt tcaattggta cgtggacggc gtggaagtgc acaacgccaa gaccaagccc 900
agagaggaac agtacaactc cacctaccgg gtggtgtccg tgctgacagt gctgcaccag 960
gactggctga acggcaaaga gtacaagtgc aaggtgtcca acaaagccct gcctgccccc 1020
atcgagaaaa ccatcagcaa ggccaagggc cagccccgcg aaccccaggt gtacacactg 1080
cctcccagca gggacgagct gaccaagaac caggtgtccc tgacctgtct cgtgaaaggc 1140
ttctacccct ccgatatcgc cgtggaatgg gagagcaacg gccagcccga gaacaactac 1200
aagaccaccc cccctgtgct ggacagcgac ggctcattct tcctgtacag caagctgacc 1260
gtggacaagt cccggtggca gcagggcaac gtgttcagct gcagcgtgat gcacgaggcc 1320
ctgcacaacc actacacaca gaagtccctg agcctgagcc ccggctga 1368

<210> SEQ ID NO 31
<211> LENGTH: 455
<212> TYPE: PRT
<213> ORGANISM: Artificial Sequence
<220> FEATURE:
<223> OTHER INFORMATION: HC mAb7

<400> SEQUENCE: 31

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Ser Tyr
20 25 30

-continued

```
Gly Ile Ser Trp Val Arg Gln Ala Pro Gly Gln Gly Leu Glu Trp Met
        35                  40                  45

Gly Trp Ile Ser Thr Tyr Lys Gly Tyr Thr Gln Tyr Ala Gln Asn Phe
    50                  55                  60

Gln Gly Arg Val Thr Ile Thr Thr Asp Thr Pro Ala Thr Thr Val Tyr
65                  70                  75                  80

Met Glu Leu Arg Ser Leu Arg Ser Asp Asp Thr Ala Val Tyr Tyr Cys
                85                  90                  95

Ala Arg Val Leu Ser Glu Thr Gly Tyr Phe Tyr Tyr Tyr Tyr Tyr Gly
            100                 105                 110

Met Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430
```

-continued

```
Ser Cys Ser Val Leu His Glu Ala Leu His Ser His Tyr Thr Gln Lys
        435                 440                 445

Ser Leu Ser Leu Ser Pro Gly
    450                 455
```

<210> SEQ ID NO 32
<211> LENGTH: 1368
<212> TYPE: DNA
<213> ORGANISM: Artificial Sequence
<220> FEATURE:
<223> OTHER INFORMATION: HC mAb7 nucleic acid sequence

<400> SEQUENCE: 32

```
caggtgcagc tggtgcagtc tggcgccgaa gtgaagaaac caggcgccag cgtgaaggtg     60

tcctgcaagg ccagcggcta cagcttcacc agctacggca tcagctgggt gcgccaggct    120

cctggacagg gcctggaatg gatgggctgg atcagcacct acaagggcta cacccagtac    180

gcccagaact tccagggcag agtgaccatc accaccgaca cccctgccac caccgtgtac    240

atggaactgc ggagcctgag aagcgacgac accgccgtgt actactgcgc cagagtgctg    300

agcgagacag gctactttta ctactactat tacggcatgg acgtgtgggg ccagggcacc    360

ctcgtgacag tgtctagcgc cagcacaaag ggccccagcg tgttccctct ggcccctagc    420

agcaagagca catctggcgg aacagccgcc ctgggctgcc tcgtgaagga ctactttccc    480

gagcccgtga ccgtgtcctg gaacagcggc gctctgacct ctggcgtgca cacctttcca    540

gccgtgctgc agagcagcgg cctgtactct ctgagcagcg tcgtgactgt gcccagcagc    600

agcctgggaa cccagaccta catctgcaac gtgaaccaca agcccagcaa caccaaggtg    660

gacaagaagg tggaacccaa gagctgcgac aagacccaca cctgtccccc ttgtcctgcc    720

cctgaactgc tgggcggacc ttccgtgttc ctgttccccc caaagcccaa ggacaccctg    780

atgatcagcc ggacccccga agtgacctgc gtggtggtgg atgtgtccca cgaggaccct    840

gaagtgaagt tcaattggta cgtggacggc gtggaagtgc acaacgccaa gaccaagccc    900

agagaggaac agtacaactc cacctaccgg gtggtgtccg tgctgacagt gctgcaccag    960

gactggctga acggcaaaga gtacaagtgc aaggtgtcca acaaagccct gcctgccccc   1020

atcgagaaaa ccatcagcaa ggccaagggc cagccccgcg aaccccaggt gtacacactg   1080

cctcccagca gggacgagct gaccaagaac caggtgtccc tgacctgtct cgtgaaaggc   1140

ttctacccct ccgatatcgc cgtggaatgg gagagcaacg gccagcccga gaacaactac   1200

aagaccaccc cccctgtgct ggacagcgac ggctcattct tcctgtacag caagctgacc   1260

gtggacaagt cccggtggca gcagggcaac gtgttcagct gcagcgtgct gcacgaggcc   1320

ctgcacagcc actacacaca gaagtccctg agcctgagcc ccggctga                1368
```

<210> SEQ ID NO 33
<211> LENGTH: 16
<212> TYPE: PRT
<213> ORGANISM: Artificial Sequence
<220> FEATURE:
<223> OTHER INFORMATION: mAb2 CDRH3
<220> FEATURE:
<221> NAME/KEY: MISC_FEATURE
<222> LOCATION: (8)..(8)
<223> OTHER INFORMATION: X = any amino acid except M
<220> FEATURE:
<221> NAME/KEY: MISC_FEATURE
<222> LOCATION: (12)..(12)
<223> OTHER INFORMATION: X = any amino acid except N
<220> FEATURE:

```
<221> NAME/KEY: MISC_FEATURE
<222> LOCATION: (13)..(13)
<223> OTHER INFORMATION: X = any amino acid except G

<400> SEQUENCE: 33

Ala Thr Gly Gly Phe Trp Ser Xaa Ile Gly Gly Xaa Xaa Val Asp Tyr
1               5                   10                  15


<210> SEQ ID NO 34
<211> LENGTH: 16
<212> TYPE: PRT
<213> ORGANISM: Artificial Sequence
<220> FEATURE:
<223> OTHER INFORMATION: mAb10 CDRH3

<400> SEQUENCE: 34

Ala Thr Gly Gly Phe Trp Ser Ile Ile Gly Gly Asn Gly Val Asp Tyr
1               5                   10                  15


<210> SEQ ID NO 35
<211> LENGTH: 16
<212> TYPE: PRT
<213> ORGANISM: Artificial Sequence
<220> FEATURE:
<223> OTHER INFORMATION: mAb11 CDRH3

<400> SEQUENCE: 35

Ala Thr Gly Gly Phe Trp Ser Met Ile Gly Gly Gln Gly Val Asp Tyr
1               5                   10                  15


<210> SEQ ID NO 36
<211> LENGTH: 16
<212> TYPE: PRT
<213> ORGANISM: Artificial Sequence
<220> FEATURE:
<223> OTHER INFORMATION: mAb12 CDRH3

<400> SEQUENCE: 36

Ala Thr Gly Gly Phe Trp Ser Met Ile Gly Gly Asn Ala Val Asp Tyr
1               5                   10                  15


<210> SEQ ID NO 37
<211> LENGTH: 452
<212> TYPE: PRT
<213> ORGANISM: Artificial Sequence
<220> FEATURE:
<223> OTHER INFORMATION: HC mAb2

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Gly Val Asp Tyr
            100                 105                 110
```

-continued

```
Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 38
<211> LENGTH: 214
<212> TYPE: PRT
<213> ORGANISM: Artificial Sequence
<220> FEATURE:
<223> OTHER INFORMATION: LC mAb2

<400> SEQUENCE: 38

Gln Ala Val Val Thr Gln Ser Pro Ser Ser Leu Pro Ala Ser Val Gly
1               5                   10                  15
```

-continued

```
Asp Arg Val Thr Ile Thr Cys Arg Ala Ser Gln Asp Ile Arg Asn Asn
            20                  25                  30

Leu Gly Trp Tyr Gln Gln Lys Pro Gly Lys Ala Pro Glu Arg Leu Ile
        35                  40                  45

Tyr Gly Thr Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Arg Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 39
<211> LENGTH: 1359
<212> TYPE: DNA
<213> ORGANISM: Artificial Sequence
<220> FEATURE:
<223> OTHER INFORMATION: HC mAb2 nucleic acid

<400> SEQUENCE: 39

```
caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240

atggaactga gcagcctgtc cagcgaggat accgccgtgt actactgtgc caccggcggc     300

ttttggagca tgatcggcgg aaacggcgtg gactattggg gccagggaac cctcgtgacc     360

gtgtctagcg cctctacaaa gggccccagc gtgttccctc tggcccctag cagcaagagc     420

acatctggcg gaacagccgc cctgggctgc ctcgtgaagg actactttcc cgagcccgtg     480

acagtgtcct ggaacagcgg agccctgacc agcggagtgc ataccttcc agccgtgctg      540

cagagcagcg gcctgtactc tctgagcagc gtcgtgactg tgcccagcag cagcctggga     600

acccagacct acatctgcaa cgtgaaccac aagcccagca acaccaaggt ggacaagaag     660

gtggaaccca agagctgcga caagacccac acctgtcccc cttgtcctgc ccctgaactg     720

ctgggaggcc cttccgtgtt cctgttcccc ccaaagccca aggacaccct gatgatcagc     780

cggacccccg aagtgacctg cgtggtggtg gatgtgtccc acgaggaccc tgaagtgaag     840

ttcaattggt acgtggacgg ggtggaagtg cataacgcca agaccaagcc cagagaggaa     900
```

-continued

```
cagtacaaca gcacctaccg ggtggtgtcc gtgctgacag tgctgcacca ggactggctg     960

aacggcaaag agtacaagtg caaagtgtcc aacaaggccc tgcctgcccc catcgagaaa    1020

accatcagca aggccaaggg ccagccccgc gaaccccagg tgtacacact gcccccaagc    1080

agggacgagc tgaccaagaa ccaggtgtcc ctgacctgtc tcgtgaaagg cttctacccc    1140

tccgatatcg ccgtggaatg ggagagcaac ggccagcccg agaacaacta caagaccacc    1200

ccccctgtgc tggacagcga cggctcattc ttcctgtact ccaagctgac cgtggacaag    1260

tcccggtggc agcagggcaa cgtgttcagc tgcagcgtga tgcacgaggc cctgcacaac    1320

cactacaccc agaagtccct gagcctgagc cccggctga                           1359
```

<210> SEQ ID NO 40
<211> LENGTH: 645
<212> TYPE: DNA
<213> ORGANISM: Artificial Sequence
<220> FEATURE:
<223> OTHER INFORMATION: LC mAb2 nucleic acid sequence

<400> SEQUENCE: 40

```
caggctgtcg tgacacagag cccctctagc ctgcctgcca gcgtgggcga cagagtgacc      60

atcacctgta gagccagcca ggacatccgg aacaacctgg gctggtatca gcagaagccc     120

ggcaaggccc ccgagagact gatctacggc accagcaatc tgcagtccgg cgtgcccagc     180

agattttccg gctctggcag cggcaccgag ttcaccctga caatcagcag cctgcagccc     240

gaggacttcg ccacctacta ctgcctgcag cacaacagct acccccccac ctttggcaga     300

ggcaccaagg tggaaatcaa gcggacagtg gccgctccca gcgtgttcat cttcccacct     360

agcgacgagc agctgaagtc cggcacagcc tctgtcgtgt gcctgctgaa caacttctac     420

ccccgcgagg ccaaggtgca gtggaaggtg gacaatgccc tgcagtctgg caacagccag     480

gaaagcgtga ccgagcagga cagcaaggac tccacctaca gcctgtccag caccctgacc     540

ctgagcaagg ccgactacga gaagcacaag gtgtacgcct gcgaagtgac ccaccagggc     600

ctgagcagcc ctgtgaccaa gagcttcaac cggggcgagt gctga                     645
```

<210> SEQ ID NO 41
<211> LENGTH: 452
<212> TYPE: PRT
<213> ORGANISM: Artificial Sequence
<220> FEATURE:
<223> OTHER INFORMATION: HC mAb8

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Gly Val Asp Tyr
            100                 105                 110
```

```
Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Tyr Ile Thr Arg Glu Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 42
<211> LENGTH: 1359
<212> TYPE: DNA
<213> ORGANISM: Artificial Sequence
<220> FEATURE:
<223> OTHER INFORMATION: HC mAb8 nucleic acid sequence

<400> SEQUENCE: 42

```
caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120
```

```
cctggaaaag gcctggaatg gatgggcggc agcgagcgcg aagatggcga gacagtgtac    180
gcccagaagt tccagggccg gatcagcctg accgaggaca cctctatcga gacagcctac    240
atggaactga gcagcctgtc cagcgaggat accgccgtgt actactgtgc caccggcggc    300
ttttggagca tgatcggcgg aaacggcgtg gactattggg gccagggaac cctcgtgacc    360
gtgtctagcg ccagcacaaa gggccccagc gtgttccctc tggcccctag cagcaagagc    420
acatctggcg gaacagccgc cctgggctgc ctcgtgaagg actactttcc cgagcccgtg    480
acagtgtcct ggaacagcgg agccctgacc agcggcgtgc acacatttcc agccgtgctg    540
cagagcagcg gcctgtactc tctgagcagc gtcgtgactg tgcccagcag cagcctggga    600
acccagacct acatctgcaa cgtgaaccac aagcccagca acaccaaggt ggacaagaag    660
gtggaaccca agagctgcga caagacccac acctgtcccc cttgtcctgc ccctgaactg    720
ctgggaggcc cttccgtgtt cctgttcccc ccaaagccca aggacaccct gtacatcacc    780
cgcgagcccg aagtgacctg cgtggtggtg gatgtgtccc acgaggaccc tgaagtgaag    840
ttcaattggt acgtggacgg ggtggaagtg cacaacgcca agaccaagcc cagagaggaa    900
cagtacaaca gcacctaccg ggtggtgtcc gtgctgacag tgctgcacca ggactggctg    960
aacggcaaag agtacaagtg caaagtgtcc aacaaggccc tgcctgcccc catcgagaaa   1020
accatcagca aggccaaggg ccagccccgc gaaccccagg tgtacacact gcccccaagc   1080
agggacgagc tgaccaagaa ccaggtgtcc ctgacctgtc tcgtgaaagg cttctacccc   1140
tccgatatcg ccgtggaatg ggagagcaac ggccagcccg agaacaacta caagaccacc   1200
ccccctgtgc tggacagcga cggctcattc ttcctgtact ccaagctgac cgtggacaag   1260
tcccggtggc agcagggcaa cgtgttcagc tgtagcgtga tgcacgaggc cctgcacaac   1320
cactacaccc agaagtccct gagcctgagc cccggctga                          1359
```

```
<210> SEQ ID NO 43
<211> LENGTH: 452
<212> TYPE: PRT
<213> ORGANISM: Artificial Sequence
<220> FEATURE:
<223> OTHER INFORMATION: HC mAb9

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Gly Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

-continued

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly
    450
```

<210> SEQ ID NO 44
<211> LENGTH: 1359
<212> TYPE: DNA
<213> ORGANISM: Artificial Sequence
<220> FEATURE:
<223> OTHER INFORMATION: HC mAb9 nucleic acid sequence

<400> SEQUENCE: 44

```
caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240
```

-continued atggaactga gcagcctgtc cagcgaggat accgccgtgt actactgtgc caccggcggc 300
ttttggagca tgatcggcgg aaacggcgtg gactattggg gccagggaac cctcgtgacc 360
gtgtctagcg ccagcacaaa gggccccagc gtgttccctc tggcccctag cagcaagagc 420
acatctggcg gaacagccgc cctgggctgc ctcgtgaagg actactttcc cgagcccgtg 480
acagtgtcct ggaacagcgg agccctgacc agcggcgtgc acacatttcc agccgtgctg 540
cagagcagcg gcctgtactc tctgagcagc gtcgtgactg tgcccagcag cagcctggga 600
acccagacct acatctgcaa cgtgaaccac aagcccagca acaccaaggt ggacaagaag 660
gtggaaccca agagctgcga caagacccac acctgtcccc cttgtcctgc ccctgaactg 720
ctgggaggcc cttccgtgtt cctgttcccc ccaaagccca aggacaccct gatgatcagc 780
cggacccccg aagtgacctg cgtggtggtg gatgtgtccc acgaggaccc tgaagtgaag 840
ttcaattggt acgtggacgg ggtggaagtg cacaacgcca agaccaagcc cagagaggaa 900
cagtacaaca gcacctaccg ggtggtgtcc gtgctgacag tgctgcacca ggactggctg 960
aacggcaaag agtacaagtg caaagtgtcc aacaaggccc tgcctgcccc catcgagaaa 1020
accatcagca aggccaaggg ccagccccgc gaaccccagg tgtacacact gcccccaagc 1080
agggacgagc tgaccaagaa ccaggtgtcc ctgacctgtc tcgtgaaagg cttctacccc 1140
tccgatatcg ccgtggaatg ggagagcaac ggccagcccg agaacaacta caagaccacc 1200
ccccctgtgc tggacagcga cggctcattc ttcctgtact ccaagctgac cgtggacaag 1260
tcccggtggc agcagggcaa cgtgttcagc tgtagcgtgc tgcacgaggc cctgcacagc 1320
cactacaccc agaagtccct gagcctgagc cccggctga 1359

<210> SEQ ID NO 45
<211> LENGTH: 452
<212> TYPE: PRT
<213> ORGANISM: Artificial Sequence
<220> FEATURE:
<223> OTHER INFORMATION: HC mAb10

<400> SEQUENCE: 45

Gln Val Gln Leu Val Gln Ser Gly Ala Glu Val Lys Lys Pro Gly Ala
1 5 10 15

Ser Val Lys Val Ser Cys Lys Val Ser Gly Tyr Ile Leu Ser Lys Leu
20 25 30

Ser Val His Trp Val Arg Gln Ala Pro Gly Lys Gly Leu Glu Trp Met
35 40 45

Gly Gly Ser Glu Arg Glu Asp Gly Glu Thr Val Tyr Ala Gln Lys Phe
50 55 60

Gln Gly Arg Ile Ser Leu Thr Glu Asp Thr Ser Ile Glu Thr Ala Tyr
65 70 75 80

Met Glu Leu Ser Ser Leu Ser Ser Glu Asp Thr Ala Val Tyr Tyr Cys
85 90 95

Ala Thr Gly Gly Phe Trp Ser Ile Ile Gly Gly Asn Gly Val Asp Tyr
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 46
<211> LENGTH: 1359
<212> TYPE: DNA
<213> ORGANISM: Artificial Sequence
<220> FEATURE:
<223> OTHER INFORMATION: HC mAb10 nucleic acid sequence

<400> SEQUENCE: 46

```
caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240

atggaactga gcagcctgtc cagcgaggat accgccgtgt actactgtgc caccggcggc     300

ttttggagca tcatcggcgg aaacggcgtg gactattggg gccagggaac cctcgtgacc     360
```

```
gtgtctagcg cctctacaaa gggccccagc gtgttccctc tggcccctag cagcaagagc    420

acatctggcg gaacagccgc cctgggctgc ctcgtgaagg actactttcc cgagcccgtg    480

acagtgtcct ggaacagcgg agccctgacc agcggagtgc ataccttttcc agccgtgctg   540

cagagcagcg gcctgtactc tctgagcagc gtcgtgactg tgcccagcag cagcctggga    600

acccagacct acatctgcaa cgtgaaccac aagcccagca acaccaaggt ggacaagaag    660

gtggaaccca agagctgcga caagacccac acctgtcccc cttgtcctgc ccctgaactg    720

ctgggaggcc cttccgtgtt cctgttcccc ccaaagccca aggacaccct gatgatcagc    780

cggacccccg aagtgacctg cgtggtggtg gatgtgtccc acgaggaccc tgaagtgaag    840

ttcaattggt acgtggacgg ggtggaagtg cataacgcca agaccaagcc cagagaggaa    900

cagtacaaca gcacctaccg ggtggtgtcc gtgctgacag tgctgcacca ggactggctg    960

aacggcaaag agtacaagtg caaagtgtcc aacaaggccc tgcctgcccc catcgagaaa   1020

accatcagca aggccaaggg ccagccccgc gaaccccagg tgtacacact gcccccaagc   1080

agggacgagc tgaccaagaa ccaggtgtcc ctgacctgtc tcgtgaaagg cttctacccc   1140

tccgatatcg ccgtggaatg ggagagcaac ggccagcccg agaacaacta caagaccacc   1200

ccccctgtgc tggacagcga cggctcattc ttcctgtact ccaagctgac cgtggacaag   1260

tcccggtggc agcagggcaa cgtgttcagc tgcagcgtga tgcacgaggc cctgcacaac   1320

cactacaccc agaagtccct gagcctgagc cccggctga                          1359
```

```
<210> SEQ ID NO 47
<211> LENGTH: 452
<212> TYPE: PRT
<213> ORGANISM: Artificial Sequence
<220> FEATURE:
<223> OTHER INFORMATION: HC mAb11

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Gln Gly Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

```
<210> SEQ ID NO 48
<211> LENGTH: 1359
<212> TYPE: DNA
<213> ORGANISM: Artificial Sequence
<220> FEATURE:
<223> OTHER INFORMATION: HC mAb11 nucleic acid sequence

<400> SEQUENCE: 48

caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240

atggaactga gcagcctgtc cagcgaggat accgccgtgt actactgtgc caccggcggc     300

ttttggagca tgatcggcgg acagggcgtg gactattggg gccagggaac cctcgtgacc     360

gtgtctagcg cctctacaaa gggccccagc gtgttccctc tggcccctag cagcaagagc     420
```

```
acatctggcg gaacagccgc cctgggctgc ctcgtgaagg actactttcc cgagcccgtg    480

acagtgtcct ggaacagcgg agccctgacc agcggagtgc ataccttcc agccgtgctg    540

cagagcagcg gcctgtactc tctgagcagc gtcgtgactg tgcccagcag cagcctggga    600

acccagacct acatctgcaa cgtgaaccac aagcccagca acaccaaggt ggacaagaag    660

gtggaaccca agagctgcga caagacccac acctgtcccc cttgtcctgc ccctgaactg    720

ctgggaggcc cttccgtgtt cctgttcccc ccaaagccca aggacaccct gatgatcagc    780

cggacccccg aagtgacctg cgtggtggtg gatgtgtccc acgaggaccc tgaagtgaag    840

ttcaattggt acgtggacgg ggtggaagtg cataacgcca agaccaagcc cagagaggaa    900

cagtacaaca gcacctaccg ggtggtgtcc gtgctgacag tgctgcacca ggactggctg    960

aacggcaaag agtacaagtg caaagtgtcc aacaaggccc tgcctgcccc catcgagaaa   1020

accatcagca aggccaaggg ccagccccgc gaaccccagg tgtacacact gcccccaagc   1080

agggacgagc tgaccaagaa ccaggtgtcc ctgacctgtc tcgtgaaagg cttctacccc   1140

tccgatatcg ccgtggaatg ggagagcaac ggccagcccg agaacaacta caagaccacc   1200

ccccctgtgc tggacagcga cggctcattc ttcctgtact ccaagctgac cgtggacaag   1260

tcccggtggc agcagggcaa cgtgttcagc tgcagcgtga tgcacgaggc cctgcacaac   1320

cactacaccc agaagtccct gagcctgagc cccggctga                          1359
```

<210> SEQ ID NO 49
<211> LENGTH: 452
<212> TYPE: PRT
<213> ORGANISM: Artificial Sequence
<220> FEATURE:
<223> OTHER INFORMATION: HC mAb12

<400> SEQUENCE: 49

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Ala Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

-continued

```
Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 50
<211> LENGTH: 1359
<212> TYPE: DNA
<213> ORGANISM: Artificial Sequence
<220> FEATURE:
<223> OTHER INFORMATION: HC mAb12 nucleic acid sequence

<400> SEQUENCE: 50

caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240

atggaactga gcagcctgtc cagcgaggat accgccgtgt actactgtgc caccggcggc     300

ttttggagca tgatcggcgg aaacgccgtg gactattggg gccagggaac cctcgtgacc     360

gtgtctagcg cctctacaaa gggccccagc gtgttccctc tggcccctag cagcaagagc     420

acatctggcg gaacagccgc cctgggctgc ctcgtgaagg actactttcc cgagcccgtg     480

acagtgtcct ggaacagcgg agccctgacc agcggagtgc atacctttcc agccgtgctg     540
```

```
cagagcagcg gcctgtactc tctgagcagc gtcgtgactg tgcccagcag cagcctggga    600

acccagacct acatctgcaa cgtgaaccac aagcccagca acaccaaggt ggacaagaag    660

gtggaaccca agagctgcga caagacccac acctgtcccc cttgtcctgc ccctgaactg    720

ctgggaggcc cttccgtgtt cctgttcccc ccaaagccca aggacaccct gatgatcagc    780

cggacccccg aagtgacctg cgtggtggtg gatgtgtccc acgaggaccc tgaagtgaag    840

ttcaattggt acgtggacgg ggtggaagtg cataacgcca agaccaagcc cagagaggaa    900

cagtacaaca gcacctaccg ggtggtgtcc gtgctgacag tgctgcacca ggactggctg    960

aacggcaaag agtacaagtg caaagtgtcc aacaaggccc tgcctgcccc catcgagaaa   1020

accatcagca aggccaaggg ccagccccgc gaaccccagg tgtacacact gcccccaagc   1080

agggacgagc tgaccaagaa ccaggtgtcc ctgacctgtc tcgtgaaagg cttctacccc   1140

tccgatatcg ccgtggaatg ggagagcaac ggccagcccg agaacaacta caagaccacc   1200

ccccctgtgc tggacagcga cggctcattc ttcctgtact ccaagctgac cgtggacaag   1260

tcccggtggc agcagggcaa cgtgttcagc tgcagcgtga tgcacgaggc cctgcacaac   1320

cactacaccc agaagtccct gagcctgagc cccggctga                          1359

<210> SEQ ID NO 51
<211> LENGTH: 452
<212> TYPE: PRT
<213> ORGANISM: Artificial Sequence
<220> FEATURE:
<223> OTHER INFORMATION: HC mAb13

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Gln Gly Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Tyr Ile Thr Arg Glu Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 52
<211> LENGTH: 1359
<212> TYPE: DNA
<213> ORGANISM: Artificial Sequence
<220> FEATURE:
<223> OTHER INFORMATION: HC mAb13 nucleic acid sequence

<400> SEQUENCE: 52

```
caggtgcagc tggtgcagtc tggcgccgaa gtgaagaaac caggcgccag cgtgaaggtg     60

tcctgcaagg tgtccggcta catcctgagc aagctgagcg tgcactgggt gcgccaggcc    120

cctggaaaag gcctggaatg gatgggcggc agcgagcgcg aagatggcga gacagtgtac    180

gcccagaagt tccagggccg gatcagcctg accgaggaca cctctatcga gacagcctac    240

atggaactga gcagcctgtc cagcgaggat accgccgtgt actactgtgc caccggcggc    300

ttttggagca tgatcggcgg acagggcgtg gactattggg gccagggaac cctcgtgacc    360

gtgtctagcg ccagcacaaa gggccccagc gtgttccctc tggcccctag cagcaagagc    420

acatctggcg gaacagccgc cctgggctgc ctcgtgaagg actactttcc cgagcccgtg    480

acagtgtcct ggaacagcgg agccctgacc agcggcgtgc acacatttcc agccgtgctg    540

cagagcagcg gcctgtactc tctgagcagc gtcgtgactg tgcccagcag cagcctggga    600
```

```
acccagacct acatctgcaa cgtgaaccac aagcccagca acaccaaggt ggacaagaag    660

gtggaaccca agagctgcga caagacccac acctgtcccc cttgtcctgc ccctgaactg    720

ctgggaggcc cttccgtgtt cctgttcccc ccaaagccca aggacaccct gtacatcacc    780

cgcgagcccg aagtgacctg cgtggtggtg gatgtgtccc acgaggaccc tgaagtgaag    840

ttcaattggt acgtggacgg ggtggaagtg cacaacgcca agaccaagcc cagagaggaa    900

cagtacaaca gcacctaccg ggtggtgtcc gtgctgacag tgctgcacca ggactggctg    960

aacggcaaag agtacaagtg caaagtgtcc aacaaggccc tgcctgcccc catcgagaaa   1020

accatcagca aggccaaggg ccagccccgc gaaccccagg tgtacacact gcccccaagc   1080

agggacgagc tgaccaagaa ccaggtgtcc ctgacctgtc tcgtgaaagg cttctacccc   1140

tccgatatcg ccgtggaatg ggagagcaac ggccagcccg agaacaacta caagaccacc   1200

ccccctgtgc tggacagcga cggctcattc ttcctgtact ccaagctgac cgtggacaag   1260

tcccggtggc agcagggcaa cgtgttcagc tgtagcgtga tgcacgaggc cctgcacaac   1320

cactacaccc agaagtccct gagcctgagc cccggctga                          1359


<210> SEQ ID NO 53
<211> LENGTH: 452
<212> TYPE: PRT
<213> ORGANISM: Artificial Sequence
<220> FEATURE:
<223> OTHER INFORMATION: HC mAb14

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Gln Gly Val Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

-continued

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ser His Tyr Thr Gln Lys Ser Leu Ser
        435                 440                 445

Leu Ser Pro Gly
    450
```

<210> SEQ ID NO 54
<211> LENGTH: 1359
<212> TYPE: DNA
<213> ORGANISM: Artificial Sequence
<220> FEATURE:
<223> OTHER INFORMATION: HC mAb14 nucleic acid sequence

<400> SEQUENCE: 54

```
caggtgcagc tggtgcagtc tggcgccgaa gtgaagaaac caggcgccag cgtgaaggtg      60

tcctgcaagg tgtccggcta catcctgagc aagctgagcg tgcactgggt gcgccaggcc     120

cctggaaaag gcctggaatg gatgggcggc agcgagcgcg aagatggcga gacagtgtac     180

gcccagaagt tccagggccg gatcagcctg accgaggaca cctctatcga gacagcctac     240

atggaactga gcagcctgtc cagcgaggat accgccgtgt actactgtgc caccggcggc     300

ttttggagca tgatcggcgg acagggcgtg gactattggg gccagggaac cctcgtgacc     360

gtgtctagcg ccagcacaaa gggccccagc gtgttccctc tggcccctag cagcaagagc     420

acatctggcg gaacagccgc cctgggctgc ctcgtgaagg actactttcc cgagcccgtg     480

acagtgtcct ggaacagcgg agccctgacc agcggcgtgc acacatttcc agccgtgctg     540

cagagcagcg gcctgtactc tctgagcagc gtcgtgactg tgcccagcag cagcctggga     600

acccagacct acatctgcaa cgtgaaccac aagcccagca acaccaaggt ggacaagaag     660

gtggaaccca agagctgcga caagacccac acctgtcccc cttgtcctgc ccctgaactg     720
```

-continued

```
ctgggaggcc cttccgtgtt cctgttcccc ccaaagccca aggacaccct gatgatcagc    780

cggacccccg aagtgacctg cgtggtggtg gatgtgtccc acgaggaccc tgaagtgaag    840

ttcaattggt acgtggacgg ggtggaagtg cacaacgcca agaccaagcc cagagaggaa    900

cagtacaaca gcacctaccg ggtggtgtcc gtgctgacag tgctgcacca ggactggctg    960

aacggcaaag agtacaagtg caaagtgtcc aacaaggccc tgcctgcccc catcgagaaa   1020

accatcagca aggccaaggg ccagccccgc gaaccccagg tgtacacact gcccccaagc   1080

agggacgagc tgaccaagaa ccaggtgtcc ctgacctgtc tcgtgaaagg cttctacccc   1140

tccgatatcg ccgtggaatg ggagagcaac ggccagcccg agaacaacta caagaccacc   1200

ccccctgtgc tggacagcga cggctcattc ttcctgtact ccaagctgac cgtggacaag   1260

tcccggtggc agcagggcaa cgtgttcagc tgtagcgtgc tgcacgaggc cctgcacagc   1320

cactacaccc agaagtccct gagcctgagc cccggctga                          1359
```

<210> SEQ ID NO 55
<211> LENGTH: 329
<212> TYPE: PRT
<213> ORGANISM: Artificial Sequence
<220> FEATURE:
<223> OTHER INFORMATION: IgG1 constant region

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 56
<211> LENGTH: 123
<212> TYPE: PRT
<213> ORGANISM: Artificial Sequence
<220> FEATURE:
<223> OTHER INFORMATION: VH mAb10

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Ile Ile Gly Gly Asn Gly Val Asp Tyr
            100                 105                 110

Trp Gly Gln Gly Thr Leu Val Thr Val Ser Ser
        115                 120


<210> SEQ ID NO 57
<211> LENGTH: 123
<212> TYPE: PRT
<213> ORGANISM: Artificial Sequence
<220> FEATURE:
<223> OTHER INFORMATION: VH mAb11

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80
```

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Gln Gly Val Asp Tyr
            100                 105                 110

Trp Gly Gln Gly Thr Leu Val Thr Val Ser Ser
        115                 120

<210> SEQ ID NO 58
<211> LENGTH: 123
<212> TYPE: PRT
<213> ORGANISM: Artificial Sequence
<220> FEATURE:
<223> OTHER INFORMATION: VH mAb12

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ile Leu Ser Lys Leu
            20                  25                  30

Ser Val His Trp Val Arg Gln Ala Pro Gly Lys Gly Leu Glu Trp Met
        35                  40                  45

Gly Gly Ser Glu Arg Glu Asp Gly Glu Thr Val Tyr Ala Gln Lys Phe
    50                  55                  60

Gln Gly Arg Ile Ser Leu Thr Glu Asp Thr Ser Ile Glu Thr Ala Tyr
65                  70                  75                  80

Met Glu Leu Ser Ser Leu Ser Ser Glu Asp Thr Ala Val Tyr Tyr Cys
                85                  90                  95

Ala Thr Gly Gly Phe Trp Ser Met Ile Gly Gly Asn Ala Val Asp Tyr
            100                 105                 110

Trp Gly Gln Gly Thr Leu Val Thr Val Ser Ser
        115                 120

<210> SEQ ID NO 59
<211> LENGTH: 221
<212> TYPE: PRT
<213> ORGANISM: Artificial Sequence
<220> FEATURE:
<223> OTHER INFORMATION: IgG1 FC region A

<400> SEQUENCE: 59

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

```
Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Ala His Tyr Thr Gln Lys Ser Leu Ser Leu Ser Pro Gly
    210                 215                 220


<210> SEQ ID NO 60
<211> LENGTH: 221
<212> TYPE: PRT
<213> ORGANISM: Artificial Sequence
<220> FEATURE:
<223> OTHER INFORMATION: IgG1 FC region AAA

<400> SEQUENCE: 60

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Ala Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Ala Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Ala His Tyr Thr Gln Lys Ser Leu Ser Leu Ser Pro Gly
    210                 215                 220


<210> SEQ ID NO 61
<211> LENGTH: 221
<212> TYPE: PRT
<213> ORGANISM: Artificial Sequence
<220> FEATURE:
<223> OTHER INFORMATION: IgG1 FC region QL
```

<400> SEQUENCE: 61

```
Cys Pro Pro Cys Pro Ala Pro Glu Leu Leu Gly Gly Pro Ser Val Phe
1               5                   10                  15

Leu Phe Pro Pro Lys Pro Lys Asp Gln Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Leu His Glu Ala Leu His
        195                 200                 205

Asn His Tyr Thr Gln Lys Ser Leu Ser Leu Ser Pro Gly
    210                 215                 220
```

<210> SEQ ID NO 62
<211> LENGTH: 221
<212> TYPE: PRT
<213> ORGANISM: Artificial Sequence
<220> FEATURE:
<223> OTHER INFORMATION: IgG1 FC region YTE

<400> SEQUENCE: 62

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Tyr Ile Thr Arg Glu Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125
```

-continued

```
Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly
    210                 215                 220


<210> SEQ ID NO 63
<211> LENGTH: 221
<212> TYPE: PRT
<213> ORGANISM: Artificial Sequence
<220> FEATURE:
<223> OTHER INFORMATION: IgG1 FC region LS

<400> SEQUENCE: 63

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Leu His Glu Ala Leu His
        195                 200                 205

Ser His Tyr Thr Gln Lys Ser Leu Ser Leu Ser Pro Gly
    210                 215                 220
```